US008076294B2

(12) United States Patent
Kinney et al.

(10) Patent No.: US 8,076,294 B2
(45) Date of Patent: Dec. 13, 2011

(54) COLLAGEN-RELATED PEPTIDES AND USES THEREOF

(75) Inventors: William A. Kinney, Newtown, PA (US); Mabel Alarnino Cejas, Oreland, PA (US); Bruce E. Maryanoff, Forest Grove, PA (US); Thomas Matalenas, Bound Brook, NJ (US); Chunlin Yang, Belle Mead, NJ (US)

(73) Assignee: Advanced Technologies and Regenerative Medicine, LLC., Rayham, MA (US)

( * ) Notice: Subject to any disclaimer, the term of this patent is extended or adjusted under 35 U.S.C. 154(b) by 368 days.

(21) Appl. No.: 12/179,778

(22) Filed: Jul. 25, 2008

(65) Prior Publication Data

US 2009/0068246 A1    Mar. 12, 2009

Related U.S. Application Data

(60) Provisional application No. 60/953,354, filed on Aug. 1, 2007.

(51) Int. Cl.
*A61K 38/39* (2006.01)
*C07K 14/78* (2006.01)

(52) U.S. Cl. .................. 514/17.2; 514/21.3; 530/356

(58) Field of Classification Search .................. None
See application file for complete search history.

(56) References Cited

U.S. PATENT DOCUMENTS

| | | | |
|---|---|---|---|
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,205,399 A | 6/1980 | Shalaby et al. |
| 4,208,511 A | 6/1980 | Shalaby et al. |
| 4,960,594 A | 10/1990 | Honeycutt |
| 5,117,009 A | 5/1992 | Barany |
| 5,196,566 A | 3/1993 | Barany et al. |
| 5,412,068 A | 5/1995 | Tang et al. |
| 5,464,929 A | 11/1995 | Bezwada et al. |
| 5,571,529 A | 11/1996 | Cheong |
| 5,595,751 A | 1/1997 | Bezwada et al. |
| 5,597,579 A | 1/1997 | Bezwada et al. |
| 5,607,687 A | 3/1997 | Bezwada et al. |
| 5,618,552 A | 4/1997 | Bezwada et al. |
| 5,620,698 A | 4/1997 | Bezwada et al. |
| 5,645,850 A | 7/1997 | Bezwada et al. |
| 5,648,088 A | 7/1997 | Bezwada et al. |
| 5,698,213 A | 12/1997 | Jamiolkowski et al. |
| 5,700,583 A | 12/1997 | Jamiolkowski et al. |
| 5,859,150 A | 1/1999 | Jamiolkowski et al. |
| 5,919,893 A | 7/1999 | Roby et al. |
| 5,973,112 A | 10/1999 | Raines |
| 6,019,996 A | 2/2000 | Cheong |
| 6,096,710 A | 8/2000 | Goodman et al. |
| 6,096,863 A | 8/2000 | Fields et al. |
| 6,326,410 B1 | 12/2001 | Cheong |
| 6,329,506 B1 | 12/2001 | Goodman et al. |
| 6,669,980 B2 | 12/2003 | Hansen |
| 2003/0162941 A1 | 8/2003 | Tanihara et al. |
| 2005/0147690 A1 | 7/2005 | Masters et al. |
| 2006/0073207 A1 | 4/2006 | Masters et al. |
| 2006/0188547 A1 | 8/2006 | Bezwada |
| 2009/0004253 A1 | 1/2009 | Brown |
| 2009/0005881 A1 | 1/2009 | Kamitakahara |

FOREIGN PATENT DOCUMENTS

| | | |
|---|---|---|
| JP | 2005053878 A | 3/2005 |
| JP | 2005058106 A | 3/2005 |
| JP | 2005058499 A | 3/2005 |
| JP | 2005060314 A | 3/2005 |
| JP | 2005060315 A | 3/2005 |
| JP | 2005060550 A | 3/2005 |
| JP | 2005126360 A | 5/2005 |
| JP | 2005206542 A | 8/2005 |
| WO | WO 91/09079 A1 | 6/1991 |
| WO | WO 98/07752 A1 | 2/1998 |
| WO | WO 98/52620 A2 | 11/1998 |
| WO | WO 99/10381 A | 3/1999 |
| WO | WO 99/050281 A2 | 10/1999 |
| WO | WO 00/009018 A1 | 2/2000 |
| WO | WO 2006/098326 A1 | 9/2006 |
| WO | WO 2007/017671 A1 | 2/2007 |
| WO | WO 2007/44026 A1 | 4/2007 |
| WO | WO 2007/052067 A2 | 5/2007 |
| WO | WO 2007/075807 A2 | 7/2007 |
| WO | WO 2009/018126 A2 | 2/2009 |

OTHER PUBLICATIONS

J.M. Stewart et al., Solid Phase Peptide Synthesis, 2nd edition, Pierce Chemical Company, Rockford, Illinois (1984).
M. Bodanzsky and A. Eodanzsky, The Practice of Peptide Synthesis, Springer Verlag, New York (1984).
J. H. Jones, The Chemical Synthesis of Peptides. Oxford University Press, Oxford 1991.
Applied Biosystems 430A Users Manual, ABI Inc., Foster City, California.
G. A. Grant, (Ed.) Synthetic Peptides, A User's Guide. W. H. Freeman & Co., New York 1992.
E. Atherton and R.C. Sheppard,Solid Phase PeptideSynthesis, A Practical Approach. IRL Press 1989.
G.E. Fields, (Ed.) Solid-Phase Peptide Synthesis (Methods in Enzymology vol. 289). Academic Press, New York and London 1997).
Rowe RC et al., *Handbook of Pharmaceutical Excipients*, (Fifth Edition, Oct. 2005, Pharmaceutical Press, Eds.
Bagrodia S et al., "Effects of Solvent Casting Copolymer Materials as Related to Mechanical Properties," J Biomed Mater Res., Jan. 1976, 10(1), 101-11.
Kemnitzer et al., in the *Handbook of Biodegradable Polymers*,edited by Domb, et. al., Hardwood Academic Press, pp. 251-272 (1997).
Allcock in *The Encyclopedia of Polymer Science*, vol. 13, pp. 31-41, Wiley Intersciences, John Wiley & Sons, 1988.
Vandorpe et al., in the *Handbook of Biodegradable Polymers*, edited by Domb, et al, Hardwood Academic Press, pp. 161-182 (1997).
Heller in *Handbook of Biodegradable Polymers*,edited by Domb, et al, Hardwood Academic Press, pp. 99-119 (1997).

(Continued)

*Primary Examiner* — Christina Bradley

(57) ABSTRACT

The present invention relates to a collagen-related polypeptide (CRP) having hydrophobic amino acid groups at the N- and C-termini capable of non-covalent self-assembly into collagen mimetic triple helices and fibrils thereof and the synthesis, methods of use and compositions thereof.

37 Claims, 1 Drawing Sheet

OTHER PUBLICATIONS

Melancini,G. et al, Acetyl-Terminated and Template-Assembled Collagen-Based Polypeptides Composed of Gly-Pro-Hyp Sequences. 3. Conformational Analysis by 1H-NMR and Molecular Modeling Studies. J. Am. Chem. Soc 1996, vol. 118, No. 43, pp. 10359-10364, especially abstract.

Long, C. G. et al. Characterization of collagen-like peptides containing interruptions in the repeating Gly-X-Y sequence. Biochemistry. 1993, vol. 32, No. 43, pp. 11688-11695, especially abstract.

Wang, A. Y., Facile Modification of Collagen Directed by Collagen Mimetic Peptides, J. Am. Chem. Soc. 2005, vol. 127, No. 12, pp. 4130-4131, especially abstract.

Jiravanichanun et al., Unexpected puckering of ydroxyproline in the guest triplets, Hyp-Pro-Gly and Pro-alloHyp-Gly sandwiched between Pro-Pro-gly sequence. ChemBioChem. 2005, vol. 6, pp. 1184-1187, especially abstract.

Kar, K. et al. Self-association of Collagen Triple Helix Peptides into Higher Order Structures. Journal of Biological Chemistry. 2006, vol. 281, No. 44, p. 33283-33290, especially abstract.

Bansal, M. et al., Triple-helical model for (Gly-Pro-Hp)n with cis peptide units. Biopolymers. 1975, vol. 14, No. 12, pp. 2457-2466, especially abstract.

Cejas et al., Collagen-Related Peptides: Self-Assembly of Short, Single Strands into a Functional biomaterial of Micrometer Scale, J. Am. Chem. Soc., 129, pp. 2202-2203 2007.

Shoulders et al., Synthesis of superbly hyperstable collagen triple helices via integration of steric and stereoelectronic effects, Dept. of Chemistry, University of Wisconsin-Madison, Madison, WI, Abstracts of Papers, 233rd ACS National Meeting, Chicago, IL, US, Mar. 25-29, 2007.

Rich A et al.,"The Molecular Structure of Collagen",*J. Mol. Biol.*,1961, 3, 483-506.

Feng Y et al., "Acetyl-Terminated and Template-Assembled Collagen-Based PolypeptidesComposed of Gly-Pro-Hyp Sequences. 2. Synthesis and Conformational Analysis by Circular Dichroism, Ultraviolet Absorbance, and Optical Rotation", *J. Am. Chem. Soc.*, 1996, 118, 10351-10358.

Fields GB et al.,"Perspectives on the Synthesis and Application of Triple-Helical, Collagen-Model Peptides", *Biopolymers* 1996, 40, 345-357.

Holmgren SK et al.,"Code for collagenÕs stability deciphered Nature" 1998, 392, 666-667.

Jenkins CL et al.,"Insights on the conformational stability of collagen", *Nat. Prod. Rep.* 2002, 19, 49-59.

Shah NK et al. "A Host-Guest Set of Triple-Helical Peptides: Stability of Gly-X-Y TripletsContaining Common Nonpolar Residuest", *Biochemistry* 1996, 35, 10262-10268.

Rao Ghr et al., "Promotion of Human Platelet Adhesion and Aggregation by a Synthetic, Triple-helical Mini-collage",*J. Biol. Chem.* 1994, 269, 13899-13903.

Morton LF et al.,"Integrin a2b1—Independent activation of platelets by simp~a coUagen-llke peptldes: collagen tertiary (triple-helical) and quaternary (polymeric) structures are sufficient alone for a2b1-Independent platelet reactivity" *Biochem. J.* 1995, 306, 337-344.

Knight CG et al., "Collagen-platelet interaction: Gly-Pro-Hyp is uniquely specific for platelet Gp VI and mediates platelet activation by collagen", *Cardiovasc. Res.* 1999, 41, 450-457.

Koide T et al.,"Self-complementary peptides for the formation of collagen-like triple helical supramolecules", *Bioorg. Med. Chem. Lett.* 2005, 15, 5230-5233.

Kotch F et al., "Self-assembly of synthetic collagen triple helices",*Proc. Natl. Acad. Sci USA* 2006, 103, 3028-3033.

Blay G et al.,"A Hydrogen-Bonded Supramolecular meso-Helix", *Eur. J. Org. Chem.* 2003, 1627-1630.

Hunter CA et al,"The nature of .pi.-.pi. Interactions", *J. Am. Chem. Soc.* 1990, 112, 5525-5534.

Gdaniec M et al., "Supramolecular Assemblies of Hydrogen-Bonded Carboxylic Acid Dimers Mediated by Phenyl-Pentafluorophenyl Stacking Interactions", *Angew. Chem. Int. Ed.* 2003, 42, 3903-3906.

Lozman et al.,"Complementary polytopic interactions (CPI) as revealed by molecular modelling using the XED force field", *J. Chem. Soc., Perkin Trans.* 2 2001, 1446-1453.

Helseth DL, Jr. and Veis A,"Collagen Self-assembly in Vitro" *J. Biol. Chem.*, 1981, 256, 7118-7128.

Prockop DJ et al., "Inhibition of the Self-assembly of Collagen I into Fibrils with Synthetic Peptides",*J. Biol. Chem.* 1998, 273, 15598-15604.

Traub W, "Molecular Assembly in Collagen" *FEBS Letters*, Aug. 1978, vol. 92, No. 1 114-120.

Smith CS, et al., "Tritiated D-ala1-Peptide T Binding:A Pharmacologic Basis for the Design of Drugs Which Inhibit HIV Receptor Binding",Drug Development Res., 1988, 15, pp. 371-379.

S. Matsuda,"Thermodynamics of Formation of Porous PolymericMembrane from Solutions", 1991,vol. 23 No. 5, Polymer Journal,435-444.

Cohn et al.,"Biodegradable PEO/PLA block copolymers", Journal of Biomaterials Research, 1998, vol. 22, pp. 993-1009.

Cohn,"New Tailor-Hade Biodegradable Polymeric Biomaterials", Polymer Preprints (ACS Division of Polymer Chemistry), 1989, vol. 30(1), p. 498.

Pulapura et al., "Tyrosine-Derived Polycarbonates: Backbone-Modified "Pseudo"-Poly(Amino Acids} Designed for Biomedical Applications", Biopolymers, 1992, vol. 32, Issue 4, pp. 411-417.

Ertel et al.,"Evaluation of a series of tyrosine-derived polycarbonates as degradable biomaterials",1994, vol. 28, J. Biomed. Mater. Res.,919-930.

Yun JH, et al.,"A Disposable, Coated Wire Heparin Sensor",40(3) Asaio J.M, 401-5 (Jul.-Sep. 1994).

Krogars K, et al,"Tablet film-coating with amylose-rich maize starch", *Eur J Pharm Sci.*, Oct. 2002, 17 (1-2), 23-30.

Maa YF, et al.,"Biopharmaceutical Powders: Particle Formation and Formulation Considerations", *SJ Curr Pharm Biotechnol.*, Nov. 2000, 1(3), 283-302.

Albericio et al., "Preparation and application of the 5-(4-(9-fluorenylmethyloxycarbonyl)aminomethy1-3,5-dimethoxyphenoxy)-valeric acid (PAL) handle for the solid-phase synthesis of C-terminal peptide amides under mild conditions",J. Org. Chem.,1990, 55, 3730-3743.

Bella J et al.,"Crystal and Molecular Structure of a Collagen-Like Peptide at o 1.9 A Resolution", *Science* 1994, 266, 75-81.

Jorgensen WL et al.,"The OPLS [optimized potentials for liquid simulations]potential functions for proteins, energy minimizations for crystals of cyclic peptides and crambin", *J. Am. Chem. Soc.* 1988, 110, 1657-1666.

Qui D et al.,"The GB/SA Continuum Model for Solvation. A Fast Analytical Method for the Calculation of Approximate Born Radii", *J. Phys. Chem. A.*, 1997, 101, 3005-3014.

Vinter JG,"Extended Electron Distributions Applied to the Molecular Mechanics of Some Intermolecular Interactions", J. Comp.-Aid. Mol. Design, 1994, 8, 653-668.

Vinter JG, "Extended Electron Distributions Applied to the Molecular Mechanics of Some Intermolecular Interactions. II. Organic Complexes", J. Comp.-Aid. Mol. Design, 1996, 10, 417-426.

Chessari G et al., "An Evaluation of Force-Field Treatments of Aromatic Interactions",Chem. Eur. J., 2002, 8, 2860-2867.

Hoekstra WJ, et al."Potent, Orally Active Gpiibliiia Antagonists Containing a Nipecotic Acid Subunit. Structure-Activity Studies Leading to the Discovery of RWJ-53308", 1999, vol. 42, J. Med. Chem., 5254-5265.

Cejas Ma et al.: "Nanoparticles That Display Short Collagen-Related Peptides. Potent Stimulation of Human Platelet Aggregation by Triple Helical Motifs" Bioconjugate Chemistry, vol. 18, Jun. 21, 2007, pp. 1025-1027, XP002502462 the whole document.

COLLAGEN-RELATED PEPTIDES AND USES THEREOF

This application claims priority to U.S. provisional Application No. 60/953,354, filed Aug. 1, 2007.

SEQUENCE LISTING

The instant application contains a Sequence Listing which has been submitted in ASCII format via EFS-Web and is hereby incorporated by reference in its entirety. Said ASCII copy, created on Apr. 15, 2011, is named ETH53USN.txt and is 81,443 bytes in size.

FIELD OF THE INVENTION

The present invention is directed to collagen-related peptides (CRPs) having hydrophobic amino acid groups at the N- and C-termini and to collagen mimetic trimers and fibrils thereof and the synthesis, methods of use and compositions thereof.

BACKGROUND OF THE INVENTION

Collagen, the most abundant protein in mammals, is widely distributed within the body and the rigidity of its rope-like triple helix and assembled fibrils enables it to perform an essential structural role, helping to provide mechanical strength to tissues. The most abundant fibrillar collagens, types I, II and III, occur in skin, bone, cartilage, tendons, ligaments, blood vessels and the vitreous humour of the eye. The more complex non-fibrillar collagens, such as types IV and VI, form two- and three-dimensional networks, supporting the interstitial tissues of the body and being the fundamental component of the basement membranes to which epithelial and endothelial cell layers can attach.

In general, fibrillar collagens contain three separate peptide strands wound around one another to form a triple-helix (Rich A and Crick F H C, *J. Mol. Biol.*, 1961, 3, 483-506). Geometric constraints and the stability of the collagen triple-helix require that every third amino acid be glycine (Gly or G), resulting in a repetitive -GXY- sequence, where X and Y each frequently represent proline (Pro or P) and hydroxyproline (Hyp or O). A collagen triple helix is typically over 300 nm in length and in excess of 1000 amino acids. The fibrils resulting from the assembly of such collagen triple helices exceed 1 µm in length.

In healthy, undamaged tissues, collagen supports the blood vessel wall and its surrounding tissues and is concealed by endothelial cell layers and cannot come in contact with platelets circulating within the bloodstream, which regulate the clotting process. However, damage to the vessel wall, occurring as a consequence of either mechanical trauma or rupture of atherosclerotic plaque in diseased blood vessel walls, may remove the endothelial cell layer and allow collagen to interact with the platelets and other blood plasma proteins, thus activating the platelets for aggregation and adhesion. These processes are essential to the clotting response, and are well understood in the field.

Triple Helical Configuration

Collagen has long fascinated scientists because of the extraordinary structural features and biological importance of these proteins. The study of the structure, stability and function of collagen triple helices has been facilitated by the use of synthetic collagen-related peptides (Feng Y, Melacini G, Taulane J P and Goodman M, *J. Am. Chem. Soc.*, 1996, 118, 10351-10358; Fields G B and Prockop D J, *Biopolymers* 1996, 40, 345-357 and references cited therein; Holmgren S K, Taylor K M, Bretscher L E and Raines R T, *Nature* 1998, 392, 666-667; Jenkins C L and Raines R T, *Nat. Prod. Rep.* 2002, 19, 49-59; and Shah N K, Ramshaw J A M, Kirkpatrick A, Shah C and Brodsky, B. *Biochemistry* 1996, 35, 10262-10268). For example, the use of synthetic triple-helical peptides comprising specific recognition motifs has allowed receptor-binding properties of the collagens to be investigated in detail. Additionally, the triple-helical conformation of the collagens may be a prerequisite for their recognition by platelet and other collagen receptors. Certain triple-helical sequences, moreover, may directly interact with platelet receptors such as GpVI, including the repeating triplet glycine-proline-hydroxyproline (GPO) sequence. For simple collagen-related peptides, the $(GPO)_{10}$ (SEQ ID NO: 36) sequence forms thermally stable triple-helices, with a melting temperature of 58-70° C. The hydroxyproline amino acids stabilize the triple-helical structure by facilitating the formation of water mediated hydrogen bonds and by providing stereoelectronic effects.

Furthermore, International Publication Number WO07/052,067 describes a series of short triple-helical collagen peptides covering the type III collagen domain and having platelet adhesion activity based on affinity for the A3 domain of platelet's von Willebrand factor. International Publication WO07/017,671 describes trimer peptides containing GPO repeats which, without crosslinking between the peptides, are able to activate platelets. International Publication WO06/098326 describes a synthetic collagen film prepared from a POG polypeptide and a calcium phosphate compound. Japanese Patent Publication 2005206542 describes collagen tissue structures containing polypeptide sequences Pro-X-Gly and Y-Z-Gly (wherein X and Z represent proline (Pro) and hydroxyproline (Hyp) and Y represents an amino acid residue having a carboxyl group). Japanese Patent Publication 2005126360 describes cosmetic and food compositions containing polypeptide sequence Pro-Y-Gly-Z-Ala-Gly (SEQ ID NO: 37) (wherein Y represents Gln, Asn, Leu, Ile, Val or Ala; and, Z represents Ile or Leu) prepared by solid-phase synthesis for inhibiting collagenase. United States Patent Publication 2003/162941 (equivalent to JP 2003321500) describes collagenous polypeptides with a sequence Pro-Y-Gly (wherein Y represents Pro or Hyp), having a triple helical structure. U.S. Pat. No. 5,973,112 (equivalent to WO99/10381) describes tripeptide collagen mimics of the sequence Xaa-Xbb-Gly (wherein Xaa represents an amino acid residue; and, Xbb represents 4(R)-fluoro-L-proline (Flp), 4(S)-fluoro-L-proline, 4,4-difluoroproline, or an acetyl, mesyl or trifluoromethyl modified hydroxyproline. Collagen mimic $(Pro-Flp-Gly)_{10}$ (SEQ ID NO: 38) showed increased stability relative to the collagen-related triple helixes Pro-Pro-Gly and Pro-Hyp-Gly.

Self Assembly

Several strategies have been employed in order to induce triple-helical structure formation in isolated collagen ligand sequences (as discussed in U.S. Pat. No. 6,096,863, equivalent of International Publication WO98/007752, and references therein). Triple-helix structure formation in isolated collagen sequences may be induced by adding a number of Gly-Pro-Hyp repeats to both ends of a collagenous sequence. However, even with more than 50% of the peptide sequence consisting of Gly-Pro-Hyp repeats, the resulting triple-helices may not have sufficient thermal stability to survive at physiological conditions. Although substantial stabilization of the triple-helical structure may be achieved with the introduction of covalent links between the C-terminal regions of the three peptide chains, the large size (90-125 amino acid residues) of the resulting "branched" triple-helical peptide compounds make them difficult to synthesize and purify (as discussed in U.S. Pat. No. 6,096,863 and references therein). While oligomerized CRPs, via dendrimer assembly or covalent crosslinking, may effectively induce platelet aggregation without being immobilized, less organized CRPs such as those having a (POG)$_{10}$ (SEQ ID NO: 34) sequence, lack this property (Rao G H R, Fields C G, White J G and Fields G B, *J. Biol. Chem.* 1994, 269, 13899-13903; Morton L F, Hargreaves P G, Farndale R W, Young R D and Barnes M J, *Biochem. J.* 1995, 306, 337-344; Knight C G, Morton L F, Onley D J, Peachey A R, Ichinohe T, Okuma M, Farndale R W and Barnes M J. *Cardiovasc. Res.* 1999, 41, 450-457). The availability and usefulness of CRPs capable of self-assembly has been dependent on the ease of their preparation, the simplicity and stability of the CRP structure and the potential for aggregation activity. Although the synthesis may be challenging and relatively complex, micrometer-scale CRP-based materials were obtained from the self-assembly of covalently attached triple-stranded entities by employing a cysteine knot (Koide T, Homma D L, Asada S and Kitagawa K, *Bioorg. Med. Chem. Lett.* 2005, 15, 5230-5233; and, Kotch F and Raines R T, *Proc. Natl. Acad. Sci. USA* 2006, 103, 3028-3033).

Thus, what is still needed are simplified approaches to building a collagen-like structural motif that facilitates peptide alignment and fibril initiation and propagation. Specifically, what is needed are relatively short, single-strand CRPs that are easily synthesized and are capable of non-covalent self-assembly into trimers having collagen-mimetic properties.

SUMMARY OF THE INVENTION

The present invention broadly relates to a collagen related polypeptide (CRP) capable of non-covalent self-assembly into a trimer having collagen-mimetic properties.

The CRP has an N-terminal and a C-terminal synthetic or natural hydrophobic amino acid at each end, wherein said amino acids are capable of initiating fibril propagation to form collagen-like fibrils.

The present invention also relates to a CRP of Formula (I):

$$B\text{-}(Z)_m\text{-}X$$

wherein

Z is a triplet selected from the group consisting of Gly-Pro-J, Pro-J-Gly and J-Gly-Pro;

J is independently selected from the group consisting of Hyp, fPro, mPro and Pro for each triplet Z;

m is an integer selected from 8, 9, 10, 11, 12, 13, 14 or 15;

for example, if Z is Gly-Pro-J and m is 8, then each of the eight J substituents is independently selected from the group consisting of Hyp, fPro, mPro and Pro; and, B and X are independently selected from the group consisting of F$_5$-Phe, Phe (optionally mono or disubstituted on phenyl with fluoro, chloro, bromo, hydroxy, methyl or CF$_3$), Tyr, 3,4-(OH)$_2$-Phe, MeO-Tyr, phenylglycine, 2-naphthyl-Ala, 1-naphthyl-Ala, Trp, Cha, Chg, Met, Leu, Ile and Val.

The CRPs described herein are useful in the construction of synthetic collagens which may be used to initiate platelet aggregation and for the treatment and diagnosis of bleeding disorders. The CRPs of the present invention are further useful in compositions as a hemostat.

DETAILED DESCRIPTION OF THE INVENTION

Figure 1:
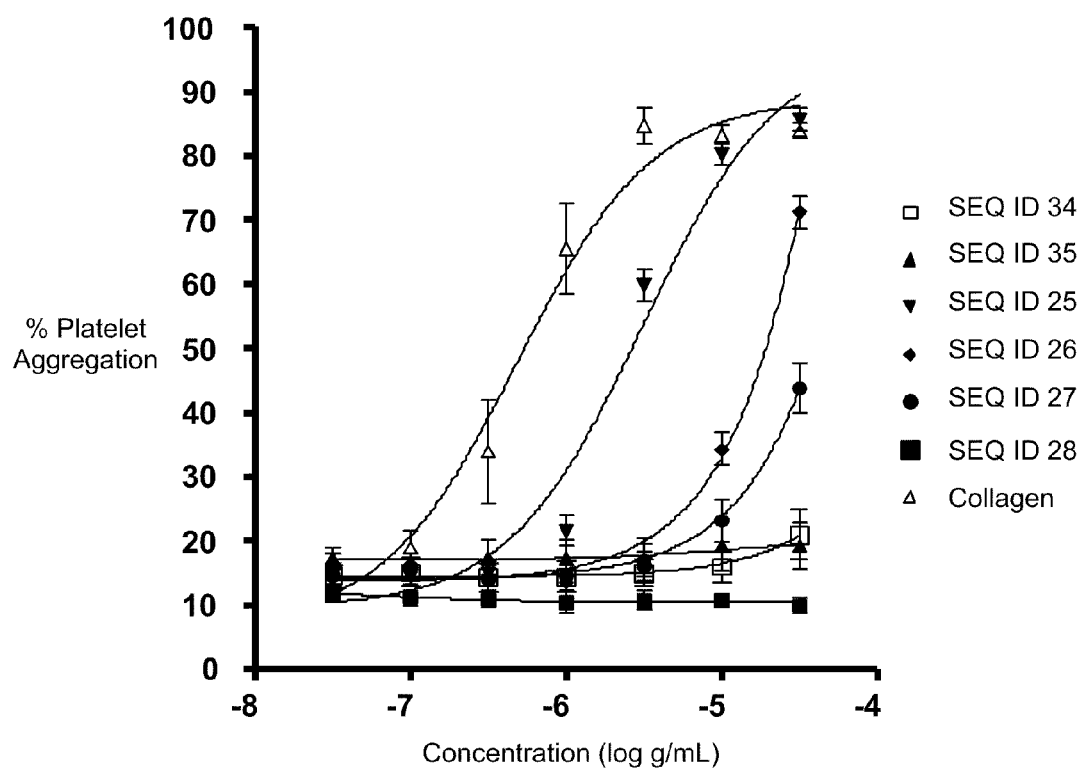
FIG. 1 is a dose response curve illustrating the activity of CRPs having SEQ ID 25, SEQ ID 26, SEQ ID 27, SEQ ID 28, SEQ ID 34 and SEQ ID 35 compared to collagen for stimulating platelet aggregation.

The present invention broadly relates to a CRP capable of non-covalent self-assembly into a trimer having collagen-mimetic properties.

The CRP has an N-terminal and a C-terminal synthetic or natural hydrophobic amino acid at each end, wherein said amino acids are capable of initiating fibril propagation to form collagen-like fibrils.

The present invention also relates to a CRP of Formula (I):

$$B\text{-}(Z)_m\text{-}X$$

wherein

Z is a triplet selected from the group consisting of Gly-Pro-J, Pro-J-Gly and J-Gly-Pro;

J is independently selected from the group consisting of Hyp, fPro, mPro and Pro for each triplet Z;

m is an integer selected from 8, 9, 10, 11, 12, 13, 14 or 15;

for example, if Z is Gly-Pro-J and m is 8, then each of the eight J substituents is independently selected from the group consisting of Hyp, fPro, mPro and Pro; and, B and X are independently selected from the group consisting of F$_5$-Phe, Phe (optionally mono or disubstituted on phenyl with fluoro, chloro, bromo, hydroxy, methyl or CF$_3$), Tyr, 3,4-(OH)$_2$-Phe, MeO-Tyr, phenyl-Gly, 2-naphthyl-Ala, 1-naphthyl-Ala, Trp, Cha, Chg, Met, Leu, Ile and Val.

The CRPs of the present invention are capable of non-covalent self-assembly into a trimer. The resulting CRP trimer is further capable of higher order self-assembly by non-covalent, aromatic-stacking and ordered hydrophobic interactions into collagen-like fibrils.

An embodiment of the present invention includes a collagen-like fibrillar substance comprising a plurality of CRPs of the present invention.

Embodiments of the present invention include a collagen-like fibrillar substance comprising a plurality of CRPs of the present invention, wherein the CRPs are present in the collagen-like fibrillar substance in the form of a plurality of CRP trimers.

In an embodiment of the invention, the CRP trimer is a homotrimer, wherein the three CRPs are homologous.

In an embodiment of the invention, the CRP trimer is a heterotrimer, wherein the three CRPs are heterologous.

An embodiment of the invention is a CRP of Formula (I), wherein Z is a triplet selected from the group consisting of Gly-Pro-J, Pro-J-Gly and J-Gly-Pro, wherein J is Hyp in at least four consecutive triplets Z.

An embodiment of the invention is a CRP of Formula (I), wherein J is independently selected from the group consisting of Hyp, fPro and Pro for each triplet Z.

An embodiment of the invention is a CRP of Formula (I), wherein J is independently selected from the group consisting of Hyp and Pro for each triplet Z.

An embodiment of the invention is a CRP of Formula (I), wherein m is 10.

An embodiment of the invention is a CRP of Formula (I), wherein B and X are independently selected from the group consisting of F$_5$-Phe, Phe (optionally mono or disubstituted on phenyl with fluoro, chloro, bromo, hydroxy, methyl or $CF_3$), Tyr, 3,4-$(OH)_2$-Phe, MeO-Tyr, phenylglycine, 2-naphthyl-Ala, 1-naphthyl-Ala, Trp, Cha, Chg, Met, Leu, Ile and Val.

An embodiment of the invention is a CRP of Formula (I), wherein B and X are independently selected from the group consisting of $F_5$-Phe, Phe and Leu.

An embodiment of the invention is a CRP of Formula (I), wherein B is selected from the group consisting of $F_5$-Phe, Phe (optionally mono or disubstituted on phenyl with fluoro, hydroxy, methyl or $CF_3$), Tyr, 3,4-$(OH)_2$-Phe, MeO-Tyr, phenylglycine, 2-naphthyl-Ala, 1-naphthyl-Ala, Trp, Cha, Chg and Leu.

An embodiment of the invention is a CRP of Formula (I), wherein B is selected from the group consisting of $F_5$-Phe, Phe (optionally mono or disubstituted on phenyl with fluoro, hydroxy, methyl or $CF_3$) and Leu.

An embodiment of the invention is a CRP of Formula (I), wherein B is selected from the group consisting of $F_5$-Phe, Phe and Leu.

An embodiment of the invention is a CRP of Formula (I), wherein X is selected from the group consisting of Phe (optionally mono or disubstituted on phenyl with fluoro, chloro, bromo, hydroxy, methyl or $CF_3$), Tyr, 3,4-$(OH)_2$-Phe, MeO-Tyr, phenylglycine, 2-naphthyl-Ala, 1-naphthyl-Ala, Tip, Cha, Chg, Met, Leu, Ile and Val.

An embodiment of the invention is a CRP of Formula (I), wherein X is Phe.

An embodiment of the invention is a CRP of Formula (I) selected from:

SEQ ID 1: B-(Gly-Pro-Hyp)$_4$-(Gly-Pro-J)$_n$-X, wherein n is an integer selected from 4, 5, 6, 7, 8, 9, 10 or 11;

SEQ ID 2: B-(Gly-Pro-Hyp)$_8$-(Gly-Pro-J)$_p$-X, wherein p is an integer selected from 0, 1, 2, 3, 4, 5, 6 or 7;

SEQ ID 3: B-(Gly-Pro-Hyp)$_{12}$-(Gly-Pro-J)$_q$-X, wherein q is an integer selected from 0, 1, 2 or 3;

SEQ ID 4: B-(Pro-Hyp-Gly)$_4$-(Pro-J-Gly)$_n$-X, wherein n is an integer selected from 4, 5, 6, 7, 8, 9, 10 or 11;

SEQ ID 5: B-(Pro-Hyp-Gly)$_8$-(Pro-J-Gly)$_p$-X, wherein p is an integer selected from 0, 1, 2, 3, 4, 5, 6 or 7;

SEQ ID 6: B-(Pro-Hyp-Gly)$_{12}$-(Pro-J-Gly)$_q$-X, wherein q is an integer selected from 0, 1, 2 or 3;

SEQ ID 7: B-(Hyp-Gly-Pro)$_4$-(J-Gly-Pro)$_n$-X, wherein n is an integer selected from 4, 5, 6, 7, 8, 9, 10 or 11;

SEQ ID 8: B-(Hyp-Gly-Pro)$_8$-(J-Gly-Pro)$_p$-X, wherein p is an integer selected from 0, 1, 2, 3, 4, 5, 6 or 7; or SEQ ID 9: B-(Hyp-Gly-Pro)$_{12}$-(J-Gly-Pro)$_q$-X, wherein q is an integer selected from 0, 1, 2 or 3.

In alternative embodiments, the CRP of Formula (I) is selected from:

SEQ ID 10: B-(Gly-Pro-J)$_n$-(Gly-Pro-Hyp)$_4$-X, wherein n is an integer selected from 4, 5, 6, 7, 8, 9, 10 or 11;

SEQ ID 11: B-(Gly-Pro-J)$_p$-(Gly-Pro-Hyp)$_8$-X, wherein p is an integer selected from 0, 1, 2, 3, 4, 5, 6 or 7;

SEQ ID 12: B-(Gly-Pro-J)$_q$-(Gly-Pro-Hyp)$_{12}$-X, wherein q is an integer selected from 0, 1, 2 or 3;

SEQ ID 13: B-(Pro-J-Gly)$_n$-(Pro-Hyp-Gly)$_4$-X, wherein n is an integer selected from 4, 5, 6, 7, 8, 9, 10 or 11;

SEQ ID 14: B-(Pro-J-Gly)$_p$-(Pro-Hyp-Gly)$_8$-X, wherein p is an integer selected from 0, 1, 2, 3, 4, 5, 6 or 7;

SEQ ID 15: B-(Pro-J-Gly)$_q$-(Pro-Hyp-Gly)$_{12}$-X, wherein q is an integer selected from 0, 1, 2 or 3;

SEQ ID 16: B-(J-Gly-Pro)$_n$-(Hyp-Gly-Pro)$_4$-X, wherein n is an integer selected from 4, 5, 6, 7, 8, 9, 10 or 11;

SEQ ID 17: B-(J-Gly-Pro)$_p$-(Hyp-Gly-Pro)$_8$-X, wherein p is an integer selected from 0, 1, 2, 3, 4, 5, 6 or 7; or SEQ ID 18: B-(J-Gly-Pro)$_q$-(Hyp-Gly-Pro)$_{12}$-X, wherein q is an integer selected from 0, 1, 2 or 3.

In still other embodiments, the CRP of Formula (I) is selected from:

SEQ ID 19: B-(Gly-Pro-J)r-(Gly-Pro-Hyp)4-(Gly-Pro-J)s-X, wherein r and s are each an integer selected from 1, 2, 3, 4, 5, 6, 7, 8, 9 or 10 and, wherein the combination of (Gly-Pro-J)r (SEQ ID NO: 39), (Gly-Pro-J)s (SEQ ID NO: 39) and (Gly-Pro-Hyp)4 (SEQ ID NO: 40) does not exceed (Z)15;

SEQ ID 20: B-(Gly-Pro-J)t-(Gly-Pro-Hyp)8-(Gly-Pro-J)u-X, wherein t and u are each an integer selected from 1, 2, 3, 4, 5 or 6 and, wherein the combination of (Gly-Pro-J)t (SEQ ID NO: 41), (Gly-Pro-J)u (SEQ ID NO: 41) and (Gly-Pro-Hyp)8 (SEQ ID NO: 42) does not exceed (Z)15;

SEQ ID 21: B-(Pro-J-Gly)r-(Pro-Hyp-Gly)4-(Pro-J-Gly)s-X, wherein r and s are each an integer selected from 1, 2, 3, 4, 5, 6, 7, 8, 9 or 10 and, wherein the combination of (Pro-J-Gly)r (SEQ ID NO: 43), (Pro-J-Gly)s (SEQ ID NO: 43) and (Gly-Pro-Hyp)4 (SEQ ID NO: 40) does not exceed (Z)15;

SEQ ID 22: B-(Pro-J-Gly)t-(Pro-Hyp-Gly)8-(Pro-J-Gly)u-X, wherein t and u are each an integer selected from 1, 2, 3, 4, 5 or 6 and, wherein the combination of (Pro-J-Gly)t (SEQ ID NO: 44), (Pro-J-Gly)u (SEQ ID NO: 44) and (Gly-Pro-Hyp)8 (SEQ ID NO: 42) does not exceed (Z)15;

SEQ ID 23: B-(J-Gly-Pro)r-(Hyp-Gly-Pro)4-(J-Gly-Pro)s-X, wherein r and s are each an integer selected from 1, 2, 3, 4, 5, 6, 7, 8, 9 or 10 and, wherein the combination of (J-Gly-Pro)r (SEQ ID NO: 45), (J-Gly-Pro)s (SEQ ID NO: 45) and (Gly-Pro-Hyp)4 (SEQ ID NO: 40) does not exceed (Z)15; or SEQ ID 24: B-(J-Gly-Pro)t-(Hyp-Gly-Pro)8-(J-Gly-Pro)u-X, wherein t and u are each an integer selected from 1, 2, 3, 4, 5, or 6 and, wherein the combination of (J-Gly-Pro)t (SEQ ID NO: 46), (J-Gly-Pro)u (SEQ ID NO: 46) and (Gly-Pro-Hyp)8 (SEQ ID NO: 42) does not exceed (Z)15.

In certain embodiments, the CRP of Formula (I) is selected from:

```
SEQ ID 25:    F5Phe-(Gly-Pro-Hyp)10-Phe;

SEQ ID 26:    Phe-(Gly-Pro-Hyp)10-Phe;

SEQ ID 27:    Leu-(Gly-Pro-Hyp)10-Phe;

SEQ ID 31:    F5Phe-(Gly-Pro-Hyp)9-Phe;

SEQ ID 32:    Phe-(Gly-Pro-Hyp)9-Phe;
and

SEQ ID 33:    Leu-(Gly-Pro-Hyp)9-Phe.
```

In the discussion of the present invention, certain other polypeptide sequences include:

```
Comparator SEQ ID 28:
Gly-(Gly-Pro-Hyp)10-Gly;

Comparator SEQ ID 29:
Ac-(Gly-Pro-Hyp)10-Gly;

Reference SEQ ID 30:
(Pro-Hyp-Gly)4-(Pro-Hyp-Ala)-(Pro-Hyp-Gly)5;

Reference SEQ ID 34:
(Pro-Hyp-Gly)10;
and

Comparator SEQ ID 35:
F5Phe-(Gly-Pro-Hyp)5-Phe.
```

By way of example, a CRP of Formula (I) having a SEQ ID 25 has the following structure:

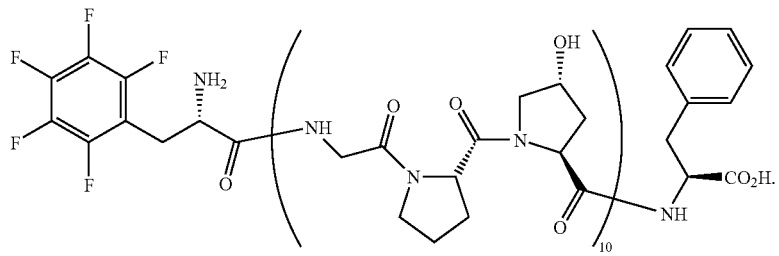

The present invention further relates to a method of forming a collagen-like fibrillar substance comprising the steps of selecting a plurality of CRPs of Formula (I) and, mixing the plurality of CRPs under aqueous conditions favorable for initiating and propagating the formation of a plurality of trimers, supramolecular composites and collagen-like fibrils.

In an embodiment of the method, the plurality of CRP trimers is selected from a plurality of homotrimers, heterotrimers or mixtures thereof.

In an embodiment of the method, the collagen-like fibrillar substance is selected from a plurality of supramolecular composites or collagen-like fibrils.

In an embodiment of the method, the favorable aqueous conditions further comprise mixing the plurality of collagen-related peptides in water or in an aqueous salt solution at a temperature of less than about 50° C.

In an embodiment of the method, the aqueous salt solution is selected from buffered saline, phosphate buffer solution, Hank's balanced salts solution, phosphate buffered saline, Tris buffered saline, Hepes buffered saline and mixtures thereof.

In an embodiment of the method, the aqueous salt solution is PBS.

DEFINITIONS

In regard to embodiments of the present invention, the following definitions and others provided throughout this specification are not to be construed, within the knowledge of one skilled in the art, as limiting the scope of the present invention.

The term "triplet" refers to a set of three amino acids as defined by the set Gly-Pro-J having the three amino acids Gly, Pro and J, the set Pro-J-Gly having the three amino acids Pro, J and Gly and, the set J-Gly-Pro having the three amino acids J, Gly and Pro.

The term "homotrimer" refers to a triple helix formed by three identical CRPs of Formula (I).

The term "heterotrimer" refers to a triple helix formed by CRPs of Formula (I).

The term "trimer" refers to a triple helix formed by three CRPs of Formula (I).

The term "supramolecular composite" refers to assembled CRP trimers of various forms, including collagen-like fibrils and fibrillar structures.

The terms "Ala" or "A" refer to the amino acid alanine; "Cha" refers to a mimetic amino acid cyclohexyl-alanine; "Chg" refers to a mimetic amino acid cyclohexyl-glycine; "$F_5$-Phe" refers to a mimetic amino acid 1,2,3,4,5-$F_5$-phenyl-alanine; "fPro" refers to a mimetic amino acid (4R)-fluoro-proline; "Gly" or "G" refer to the amino acid glycine; "Hyp" or "O" refer to a mimetic amino acid (4R)-hydroxyproline; "Met" refers to the amino acid methionine; "mPro" refers to a mimetic amino acid (4S)-methylproline; "Phe" or "F" refer to the amino acid phenylalanine; "Pro" or "P" refer to the amino acid proline; and, "Tyr" refers to the amino acid tyrosine.

DISCUSSION OF THE INVENTION

Certain self-assembling monomers have been described, where meta-substituted phenylene dioxamic acid diethyl ester monomers have been shown by solid state x-ray to self-assemble into a helical chain via H-bonding (end-to-end), with adjacent helices aligned side-to-side by -stacking (Blay G, Fernandez I, Pedro J R, Ruiz-Garcia R, Munoz M C, Cano J and Carrasco R, *Eur. J. Org. Chem.* 2003, 1627-1630). The initial design by the inventors of the present invention for a self-assembling CRP trimer involved the attachment of a phenyl oxamic ester amide group on both the N- and C-termini of a (GPO)$_{10}$ (SEQ ID NO: 36) sequence to facilitate end-to-end assembly by hydrogen bonding.

However, due to the strong noncovalent aromatic-stacking interaction between benzene and hexafluorobenzene (Hunter C A and Sanders J K M, *J. Am. Chem. Soc.* 1990, 112, 5525-5534; Gdaniec M, Jankowski W, Milewska M J and Polonski T, *Angew. Chem. Int. Ed.* 2003, 42, 3903-3906 (also, Ref 9 and 10 cited therein); and, Lozman O R, Bushby R J and Vinter J G, *J. Chem. Soc., Perkin Trans.* 2 2001, 1446-1453), the inventors of the present invention hypothesized that aromatic-stacking (end-to-end and side-to-side) and ordered hydrophobic interactions would make the CRP trimers of the present invention further capable of higher order self-assembly into collagen-like fibrils and fibers.

As a result, the hydrogen bonding self-assembly design evolved into the design of the present invention in which interactions between the aromatic and hydrophobic groups were utilized for end-to-end self-assembly by r-stacking and ordered hydrophobic interactions. The sequences of the linear CRPs of the present invention are capable of self-assembly into trimers and, subsequently, into supramolecular composites and fibrils by noncovalent means. Others have noted that the collagen sequence includes telopeptide regions specifically containing aromatic and hydrophobic amino acid residues such as Tyr, Phe and Leu. The importance of such aromatic and hydrophobic residues for triple helical self-assembly has been indicated (Helseth D L, Jr. and Veis A, *J. Biol. Chem.*, 1981, 256, 7118-7128; Prockop D J and Fertala A, *J. Biol. Chem.* 1998, 273, 15598-15604; and, Traub W, *FEBS Letters* 1978, 92, 114-120).

Accordingly, the potential for initiating fibril propagation by a CRP trimer of the present invention, for example, by a CRP trimer having a sequence SEQ ID 25: $F_5$Phe-(Gly-Pro-Hyp)$_{10}$-Phe, was investigated. As shown below in Example 3, computational molecular modeling was used to assess the interface between two head-to-tail CRP trimers having SEQ ID 25. An XED (extended electron distribution) force field was used to draw the two triple helices toward one another. As the triple helices approached each other, the phenyl/pentafluorophenyl pairs adopted a face-to-face (FTF) orientation, resulting in a total interface binding energy of –55.2 kcal/mol. When the aromatic rings were placed in an edge-to-face orientation, the re-minimized assembly reverted to the face-to-face orientation.

The interfaces of analogous CRP trimers having sequences SEQ ID 26: Phe-(Gly-Pro-Hyp)$_{10}$-Phe and SEQ ID 27: Leu-(Gly-Pro-Hyp)$_{10}$-Phe, were also examined. Comparatively, in the case of SEQ ID 26, a lower interface energy was observed (total energy of –49.2 kcal/mol) without symmetrical FTF interactions observed. An additional drop-off in binding energy occurred for SEQ ID 27 (total energy of –32.5 kcal/mol). The strong interactions between opposite ends of the CRP trimers having SEQ ID 25 and the interactions between opposite ends of the CRP trimers having SEQ ID 26 and SEQ ID 27 support the inventor's hypothesis for the potential of the CRP trimers of the present invention to initiate fibril propagation due to aromatic-stacking and ordered hydrophobic interactions between the CRP trimers.

Although the modeling work examined the end-to-end interface of CRP trimers for initiating fibril propagation, the scope of the present invention is intended to include other possible interfaces such as staggered interfaces in which the hydrophobic interactions occur in an end-to-end orientation between CRPs at different locations within a CRP trimer and side-to-side interactions with adjacent CRP trimers where allowed by hydrophobic interactions, as is the case for collagen telopeptides.

CRP Configurations

In addition to the foregoing, non-limiting embodiments, the present invention also encompasses CRPs and homotrimers and heterotrimers thereof that consist of sequences in any combination representative of Formula (I).

The overall length of a CRP as described herein may be in a range of from 26 amino acids up to 47 amino acids. In an embodiment of the present invention, the overall length of a CRP may be up to 32 amino acids.

A CRP as described herein may be polymerized or linked to a peptidyl or non-peptidyl coupling partner such as, but not limited to, an effector molecule, a label, a marker, a drug, a toxin, a carrier or transport molecule or a targeting molecule such as an antibody or binding fragment thereof or other ligand. Techniques for coupling a CRP polypeptide to both peptidyl and non-peptidyl coupling partners are well-known in the art.

In some embodiments, a CRP as described herein may be coated onto a solid surface or insoluble support. The support may be in particulate or solid form, including for example a plate, a test tube, beads, a ball, a filter, fabric, polymer or a membrane. Methods for fixing a CRP polypeptide to solid surfaces or insoluble supports are known to those skilled in the art.

In some embodiments, the support may be a protein, for example a plasma protein or a tissue protein, such as an immunoglobulin or fibronectin. In other embodiments, the support may be synthetic and may be, for example a biocompatible, biodegradable polymer. Suitable polymers include polyethylene glycols, polyglycolides, polylactides, polyorthoesters, polyanhydrides, polyphosphazenes, and polyurethanes. Another aspect of the invention provides a conjugate comprising a polypeptide as described herein attached to an inert polymer.

The inclusion of reactive groups at one end of the CRP allows chemical coupling to inert carriers such that resulting product may be delivered to pathological lesions such as chronic wounds or sites of acute traumatic injury without entry into the bloodstream.

The CRPs of the present invention may be generated wholly or partly by chemical synthesis, for example, according to well-established, standard liquid or, preferably, solid-phase peptide synthesis methods, general descriptions of which are broadly available (see, for example, in J. M. Stewart and J. D. Young, Solid Phase Peptide Synthesis, 2nd edition, Pierce Chemical Company, Rockford, Ill. (1984), in M. Bodanzsky and A. Eodanzsky, The Practice of Peptide Synthesis, Springer Verlag, New York (1984); in J. H. Jones, The Chemical Synthesis of Peptides. Oxford University Press, Oxford 1991; in Applied Biosystems 430A Users Manual, ABI Inc., Foster City, Calif., in G. A. Grant, (Ed.) Synthetic Peptides, A User's Guide. W.H. Freeman & Co., New York 1992, E. Atherton and R. C. Sheppard, Solid Phase Peptide Synthesis, A Practical Approach. IRL Press 1989 and in G. E. Fields, (Ed.) Solid-Phase Peptide Synthesis (Methods in Enzymology Vol. 289). Academic Press, New York and London 1997), or they may be prepared in solution, by the liquid phase method or by any combination of solid-phase, liquid phase and solution chemistry.

CRP Structural Modifications

A CRP as described herein may be chemically modified, for example, by addition of one or more polyethylene glycol molecules, sugars, phosphates, and/or other such molecules, where the molecule or molecules are not naturally attached to wild-type collagen proteins. Suitable chemical modifications of CRPs and methods of making CRPs by chemical synthesis are well known to those of skill in the art and are also encompassed by the present invention. The same type of modification may be present in the same or varying degree at several sites on the CRP. Furthermore, modifications can occur anywhere in the CRP sequence, including on the CRP backbone, on any amino acid side-chains and at the amino or carboxyl termini. Accordingly, a given CRP may contain many types of modifications.

As indicated above, CRP as described herein may be structurally modified. A structurally modified CRP is substantially similar in both three-dimensional shape and biological activity to a CRP described herein and preferably comprises a spatial arrangement of reactive chemical moieties that closely resembles the three-dimensional arrangement of active groups in the CRP sequence. Further modifications also can be made by replacing chemical groups of the amino acids with other chemical groups of similar structure.

Additionally, CRPs as described herein may be structurally modified to comprise one or more D-amino acids. For example, a CRP may be an enantiomer in which one or more L-amino acid residues in the amino acid sequence of the CRP is replaced with the corresponding D-amino acid residue or a reverse-D polypeptide, which is a polypeptide consisting of D-amino acids arranged in a reverse order as compared to the L-amino acid sequence described above (Smith C S, et al., Drug Development Res., 1988, 15, pp. 371-379). Methods of producing suitable structurally modified polypeptides are well known in the art.

CRP Compositions

The CRPs of the present invention may be isolated and/or purified and subsequently used as desired. In an embodiment of the present invention, the CRPs may be used in a composition, such as a pharmaceutical composition or a composition suitable for use as a medical device, that may include one or more optional components including, but not limited to one or more excipients known in the art. In addition to such non-limiting embodiments, the present invention also encompasses CRPs, as well as homotrimers and heterotrimers thereof that consist of sequences in any combination representative of Formula (I) in such compositions.

Certain polypeptides have been described for use in various pharmaceutical compositions, medical devices, and combination products. For example, International Publication WO07/044,026 describes a collagen mimetic peptide-polyethylene glycol diacrylate hydrogel scaffold for repair of damaged cartilage. United States Patent Publication US2006/073207 describes a bovine collagen/elastin/sodium heparinate amorphous coacervate composition for various medical applications. United States Patent Publication US2005/147690 describes a modified polyurethane film having a collagen/elastin/heparin embedded surface for use as a vascular graft. Japanese Patent Publication 2005060550 describes compositions for adhesion to substrates containing polypeptide sequence Pro-Y-Gly (wherein Y represents Pro or Hyp), having a triple-helical structure with a 100,000-600,000 molecular weight. Japanese Patent Publication 2005060315 describes pharmaceutical compositions containing polypeptide sequence Pro-Y-Gly (wherein Y represents Pro or Hyp) having a triple-helical structure with a 100,000-600,000 molecular weight and vitamin C. Japanese Patent Publication 2005060314 describes cosmetic compositions containing polypeptide sequence Pro-Y-Gly (wherein Y represents Pro or Hyp) having a triple-helical structure with a 100,000-600,000 molecular weight. Japanese Patent Publication 2005058499 describes a nonwoven fabric composition impregnated with a polypeptide of the sequence Pro-Y-Gly (wherein Y represents Pro or Hyp), having a triple-helical structure with a 100,000-600,000 molecular weight, which may be degraded by collagenase. Japanese Patent Publication 2005058106 describes edible compositions containing polypeptide sequence Pro-Y-Gly (wherein Y represents Pro or Hyp), having a triple-helical structure with a 100,000-600,000 molecular weight, which may be degraded by collagenase. Japanese Patent Publication 2005053878 describes polypeptides having sequences Pro-X-Gly and Pro-Y-Gly-Z-Ala-Gly (SEQ ID NO: 37) (wherein X represents Pro or Hyp; Y represents Gln, Asn, Leu, Ile, Val or Ala; and, Z represents Ile or Leu), having a triple-helical structure with a 70,000-600,000 molecular weight, which may be degraded by collagenase. International Publication WO98/52620 describes biopolymer compounds with a sequence Gly-Pro-Nleu covalently bound to a surface or surfaces of a biocompatible bulk material for use as an implant prosthesis. U.S. Pat. No. 6,096,863 describes peptide-amphiphile complexes having a lipophilic portion and a peptide portion having a collagen-like sequence $R_2O_2C(CH_2)_2CH(CO_2R_1)NHCO(CH_2)_2CO(Gly-Pro-Hyp)_{0-4}$-[peptide]-$(Gly-Pro-Hyp)_{0-4}$, "$Gly-Pro-Hyp)_{0-4}$" disclosed as SEQ ID NO: 47) where $R_1$ and $R_2$ are each independently one to twenty hydrocarbyl groups, prepared via solid-phase synthesis. U.S. Pat. Nos. 6,096,710 and 6,329,506 describe triple helical synthetic collagen derivatives having repeating amino acid triplets Gly-Xp-Pro, Gly-Pro-Yp, Gly-Pro-Hyp and Gly-Pro-Pro, wherein Xp and Yp are peptoid residues selected from N-substituted amino acids.

The present invention extends in various aspects not only to CRPs as described herein, optionally coupled to other molecules, peptides, polypeptides and specific binding members, but also includes a pharmaceutical composition, medicament, drug, medical device or component thereof, or other compositions comprising such CRPs. Such a pharmaceutical composition, medicament, drug, medical device or component thereof, or other composition may be used for various purposes, including but not limited to diagnostic, therapeutic and/or preventative purposes.

The present invention also extends to the use of such CRPs in the manufacture of such compositions and a method of making such compositions comprising admixing such CRPs with the desired optional excipients and other optional ingredients. Examples of suitable excipients include, but are not limited to any of the vehicles, carriers, buffers, stabilizers and the like that are well known in the art.

In embodiments wherein the composition is a pharmaceutical composition, the composition may contain, in addition to such CRPs, a secondary pharmaceutically active agent, wherein the resulting combination product may be further admixed with an excipient such as those well-known as pharmaceutically-acceptable in the art. Examples of such suitable excipients are disclosed in, for example, *Handbook of Pharmaceutical Excipients*, (Fifth Edition, October 2005, Pharmaceutical Press, Eds. Rowe R C, Sheskey P J and Weller P). Such materials should be non-toxic and should not interfere with the efficacy of such CRPs or the secondary pharmaceutically active agent. Such compositions of the present invention may be administered in a localized manner to a desired site or may be delivered in a manner in which the CRP or secondary pharmaceutically active agent targets particular cells or tissues. Suitable secondary pharmaceutically active agents include, but are not limited to, hemostatics (such as thrombin, fibrinogen, ADP, ATP, calcium, magnesium, $TXA_2$, serotonin, epinephrine, platelet factor 4, factor V, factor XI, PAI-1, thrombospondin and the like and combinations thereof), antiinfectives (such as antibodies, antigens, antibiotics, antiviral agents and the like and combinations thereof), analgesics and analgesic combinations or, antiinflammatory agents (such as antihistamines and the like).

In a broad use of such compositions, the composition may be applied topically to a wound site as a hemostat, such as, for example as a pharmaceutical formulation or as a component of a wound dressing. The composition may be administered alone or in combination with other treatments, either substantially simultaneously or sequentially dependent upon the condition to be treated. Such CRPs, either alone or in an article or device comprising such CRPs, including a wound dressing, may be provided in a kit, e.g. sealed in a suitable container that protects the contents from the external environment. Such a kit may include instructions for use.

In one embodiment, the CRP as described herein may be useful in stimulating hemostasis in acute trauma, e.g. after road traffic accident or battlefield injury, by being applied topically to wounds that would otherwise cause fatal blood loss. A method of stimulating hemostasis at such wound sites may comprise contacting the site with a composition comprised of the CRP as described herein, wherein the composition may optionally comprise a substrate such that the CRP is present at the substrate surface in an amount sufficient to induce and maintain hemostasis.

In another embodiment, the CRP as described herein may be useful in stimulating hemostasis in chronic wounds such as ulcers. Without wishing to be bound by theory regarding the proposed mechanism, we believe that the CRP may act to first enhance cell attachment, then the release of activated platelet granule contents may stimulate the migration of cells from the bloodstream and from nearby damaged tissues that contribute to the healing process. A method of stimulating hemostasis at such chronic wound sites in an individual may comprise contacting the site with a composition comprised of the CRP as described herein, wherein the composition may optionally comprise a substrate such that the CRP is present at the substrate surface in an amount sufficient to induce hemostasis.

Such CRPs of the present invention as described herein may be broadly useful as valuable reagents in a number of laboratory and clinical settings, including for diagnosing bleeding disorders. For example, such CRPs as described herein may be useful in the construction of synthetic collagens which may then be used to initiate platelet aggregation. In another example, such CRPs may be useful in the investigation or screening of test compounds that inhibit platelet aggregation and activation and/or blood coagulation. In a further example, such CRPs may be useful as a reagent for research into the activation and/or aggregation of platelets. A method of activating and/or aggregating platelets may comprise treating platelets with such CRPs as described herein.

In one embodiment, the platelets may be treated in vitro in the presence of blood plasma. Activity of treated platelets, i.e. platelets following contact with such CRPs as described herein, may be measured or determined, for example in the presence or absence of a factor or agent, test composition or substance of interest, employing suitable control experiments as expected in the art. The effect of a factor on platelet activation and/or aggregation may be determined by a method comprising treating platelets with such CRPs as described herein and determining the effect of the factor on the platelet activation and/or aggregation. Platelet activation and/or aggregation may be determined in the presence or absence of the factor or with the factor at different concentrations.

In another embodiment of the present invention, such CRPs of the present invention may also be useful in the diagnosis of platelet disorders, such as in diagnostics that routinely use collagen fibrils extracted from animal tissues as a reagent in platelet aggregometry, or immobilized collagen preparations as in the Platelet Function Analyzer and other instruments. For example, such CRPs may be used to investigate platelet activity or function or to diagnose a dysfunction in platelet activity by determining activation and/or aggregation of platelets in a sample treated with such CRPs as described herein. For example, such CRPs as described herein may be contacted with a blood sample obtained from the individual, then the aggregation of platelets may be determined in accordance with methods well-known in the art.

In another embodiment of the present invention, such CRPs of the present invention may be useful as a bioactive surface coating which acts to secure cell adhesion directly as well as to aggregate and activate platelets locally, such as by contributing to the production and release of other bioactive molecules. One method may, for example, comprise contacting platelets with such CRPs as described herein, which may be immobilized on a solid or semi-solid support, in the presence of blood plasma, in order to aggregate and/or activate platelets at or in the vicinity of said support.

The CRPs of the present invention may also be broadly useful in the treatment of bleeding disorders.

In one embodiment, wherein such CRPs as described herein are adsorbed on or otherwise contained in or on a solid or semi-solid support, such as an inert polymer support, the resulting support may be useful in serving as an adjunct or alternative to platelet transfusion in cases of platelet insufficiency that may result from auto-immune thrombocytopenia or from therapeutic ablation of bone marrow as in cancer therapy, as well as from bleeding disorders from other causes, such as Glanzmann's disease. In this embodiment, such CRPs that are adsorbed on or otherwise contained in or on a solid or semi-solid support, may be administered to an individual in need thereof, such as, for example, individuals that may have platelet insufficiency and/or may have a medical condition as set out above.

Such CRPs as described herein, which are adsorbed on or otherwise contained in or on a solid or semi-solid support, may also be useful in inducing thrombus formation in aortic aneurism. For example, such CRPs may be coated onto the outside of an embolic coil to secure the tissue and/or prevent further dilation of a distended artery. In this embodiment, thrombus formation in damaged vascular tissue of an individual may be induced by contacting the vascular tissue with such CRPs as described herein, which is adsorbed on or otherwise contained in or on a solid or semi-solid support, such as an inert polymer support. Examples of suitable inert polymer supports include, but are not limited to stents, embolic coils, and the like. Such an individual may suffer from medical issues such as, for example, distended artery or other blood vessels and/or an aortic aneurism. In one embodiment, the support may be an inert polymeric support comprised of proteins, polyethylene glycol, or liposomes, which is coated with an instant CRP that adsorbs to the support.

Such CRPs of the present invention as described herein may be further useful in a composition comprising a chemically defined three-dimensional polymer matrix supplemented with said collagen-related peptides for the directed differentiation of embryonic stem cells. International Publication WO07/075,807, herein incorporated by reference in its entirety and for all purposes, describes a composition comprising a chemically defined three-dimensional polymer matrix supplemented with a collagen IV polypeptide which supports directed differentiation of embryonic stem cells.

Yet another embodiment of the present invention is directed to a method for treating a hemostatic condition in a subject in need thereof comprising administration of a composition comprising a CRP of the present invention, which composition may include but not be limited to such CRPs as described herein. The polypeptide composition may optionally include a substrate during administration. Such a composition may typically be administered according to a regimen sufficient to show benefit to the subject. The actual amount administered, and rate and time-course of administration, will depend on several factors such as, for example, the nature and severity of the disease or condition being treated. The composition may be administered alone or in combination with adjunctive therapies of other treatments, either simultaneously or sequentially, dependent upon the disease or condition treated.

According to this method for treating a hemostatic condition, the CRP composition as described herein may be used alone or in combination with an excipient and other optional ingredients to provide hemostasis. In another embodiment, such CRPs may be combined with a suitable substrate for use as a hemostat. The hemostat CRP composition may be in a variety of forms, which include but are not limited to a powder, a fiber, a film or a foam.

CRP-containing foams may be prepared by processes such as, for example, lyophilization or supercritical solvent foaming. Details of these processes are well known in the art and disclosed in, for example, S. Matsuda, Polymer J., 1991, 23(5), 435-444 (lyophilization) and European Patent Application EP 464,163 B1 (supercritical solvent foaming). In general, a lyophilized foam containing the CRP of the present invention may prepared by first dissolving the CRP, and any optional ingredient known in the art such as, for example, plasticizers, in a suitable solvent under temperatures sufficient for such dissolution, then pouring the CRP-containing solution into a mold. The CRP may be present in the CRP-containing solution in an amount, based upon the total weight of the CRP-containing solution, in a range of from about 0.1 mg/mL to about 10 mg/mL, or in a range of from about 0.1 mg/mL to about 1 mg/mL, or about 0.3 mg/mL. Suitable plasticizers include, but are not limited to glycerol; polyethylene glycol; glycerin; propylene glycol; monoacetate of glycerol; diacetate of glycerol; triacetate of glycerol and mixtures thereof, and may be used in an amount, based upon the final dried weight of the CRP-containing foam, in a range of from about 0.5 percent to about 15 percent, or in a range of from about 1 percent to about 5 percent. In order to minimize possible deleterious affects to the CRP, the dissolution temperature should not exceed about 50° C. The dissolution may be performed under favorable aqueous conditions which include, but are not limited to, in water or in aqueous salt solutions such as buffered saline, phosphate buffer solution, Hank's balanced salts solution, phosphate buffered saline (PBS), Tris buffered saline, Hepes buffered saline, and mixtures thereof.

In one embodiment, the solvents may be buffered to a pH range of from about 6 to about 8. After the mold is filled with the desired amount of solution, the mold is then transferred to a lyophilizer, which will freeze, then vacuum dry the solution in order to remove the solvent from the resulting foam. Although the thickness of the resulting foam may vary depending upon, for example, the amount of solution in the mold, the concentration of CRPs in the solution, and the like, typically the resulting foam may have a thickness in a range of about 0.5 mm to about 10 mm, or in a range of from about 1 mm to about 5 mm, and a pore size in a range of from about 1 micron to about 500 microns. The foams may be made in a variety of sizes that may be suitable for use in addressing the hemostatic challenges of hemorrhage sites.

CRP-containing films may be prepared by processes such as, for example, casting the film from a suitable solvent. Details of this process is well known in the art and has been disclosed in, for example, Bagrodia S and Wilkes G L, "Effects of Solvent Casting Copolymer Materials As Related to Mechanical Properties," J Biomed Mater Res., 1976 (January), 10(1), 101-11. According to this embodiment, the CRP of the present invention, along with any optional ingredient known in the art such as, for example, plasticizers, may be dissolved in a sufficient amount of aqueous solvent. The CRP may be present in the solution in an amount, based upon the total weight of the solution, in a range of from about 0.1 mg/mL to about 10 mg/mL, or in a range of from about 0.1 mg/mL to about 1 mg/mL, or about 0.3 mg/mL. Suitable plasticizers include, but are not limited to glycerol, polyethylene glycol, glycerin, propylene glycol, monoacetate of glycerol, diacetate of glycerol, triacetate of glycerol and mixtures thereof, and may be used in an amount, based upon the final dried weight of the CRP-containing film, in a range of from about 0.5 percent to about 15 percent, or in a range of from about 1 percent to about 5 percent.

Examples of suitable aqueous solvents include, but are not limited to water, miscible organic solvents, alcohols or mixtures thereof. Examples of suitable miscible organic solvents and alcohols include, but are not limited to acetone, ethanol, isopropanol, propanol, methanol and the like and mixtures thereof. In order to minimize possible deleterious affects to the CRP, the dissolution temperature should not exceed about 50° C. The CRP-containing solution may then be added, for example, dropwise or by otherwise pouring a suitable amount to cover a desired surface area on a casting substrate.

Examples of suitable casting substrates include those comprising a material that will easily release the CRP-containing film, and may include but not be limited to those made of glass, metal, Teflon-coated containers and the like. The size and shape of such substrates may be varied according to the needs of the composition. The solvent may then be removed from the CRP-containing solution by evaporation or by air drying, then optionally the resulting film may dried by various methods, such as via vacuum drying, to remove any residual solvent. If a thicker film is desired, the process may be repeated by casting one or more layers of CRP-containing solution on top of the upper surface of the previously cast film. Although the thickness of the resulting film may vary depending upon, for example, the amount of solution poured onto the casting substrate, the concentration of CRPs in the solution and the like, typically the thickness of each film layer may be in a range of from about 50 microns to about 150 microns. As set forth above with respect to the foam, the films also may also be prepared in a variety of sizes.

CRP-containing powders may be obtained by manually or mechanically grinding or pulverizing the fibers, films, or foams comprised of the CRP of the present invention using processes well-known in the art. Exemplary techniques for grinding or pulverizing CRP fibers, films or foams into powders include, but are not limited to, those which use a mortar and pestle, a rotary blade, or an impact grinder such as a ball mill. These and other means for grinding the CRP into a powder may be accomplished at room temperature, or for cryogenically grinding processes, at temperatures below the freezing point of the CRP. The resulting CRP-containing powder may optionally be sieved to obtain a powder having a particle size in a range of from about 1 micron to about 2000 microns, or in a range of from about 10 microns to about 500 microns.

The CRP-containing powders, films, and/or foams may be applied directly to the bleeding site as a hemostat to enhance or cause hemostasis. Alternatively, the CRP described herein may be applied in combination with a substrate component, and in such embodiments, the CRP is hereinafter referred to as the CRP-hemostat component. The substrate may either be a substrate suitable for implantation into an individual, or it may be a non-implantable substrate.

Examples of suitable implantable substrates include, but are non limited to, medical devices, such as suture anchors, sutures, staples, surgical tacks, clips, plates, screws, and films; tissue engineering scaffolds, such as non-woven felts, woven meshes or fabrics; foams; and powders. These implantable substrates may be comprised of any material suitable for implantation in the body and include, but are not limited to biocompatible, bioabsorbable polymers such as aliphatic polyesters, poly(amino acids) such as poly(L-lysine and poly(glutamic acid), copoly(ether-esters), polyalkylenes oxalates such as those having an alkyl group length from one to ten carbon atoms, polyoxaamides, tyrosine derived polycarbonates, poly(iminocarbonates), polyorthoesters, polyoxaesters, polyesteramides, polyoxaesters containing amine groups, poly(anhydrides), polyphosphazenes, biomolecules (including biopolymers such as collagen, elastin, and gelatin, and polysaccharides, such as starches, alginate, pectin, carboxymethyl cellulose, salts of carboxymethyl cellulose, oxidized regenerated cellulose, and the like), and copolymers and blends thereof, as well as non-absorbable materials including, but not limited to cotton, linen, silk, nylon, such as nylon 6-6 and aromatic polyamides, such as those commercially available from E.I. du Pont de Nemours and Company under the tradenames "KEVLAR" or NOMEX, polyesters, such as poly(ethylene terephthalate), fluoropolymers, such as polytetrafluoroethylene, fluorinated poly(ethylene-propylene) (FEP) and polyvinylidene fluoride (PFA), polyolefins, such as polyethylene and polypropylene, polyurethanes and combinations thereof.

As used herein, "bioabsorbable" shall refer to materials which readily degrade via enzymatic or hydrolytic reactions upon exposure to bodily tissue within a relatively short period of time. "Degrade" shall mean that the material breaks down into small segments that can substantially be metabolized or eliminated by the body. Complete bioabsorption should take place within about twelve months, although bioabsorption may be complete for example, within about nine months, within about six months or within about three months or less.

Poly(iminocarbonates), for the purpose of this invention, are understood to include those polymers as described by Kemnitzer and Kohn, in the *Handbook of Biodegradable Polymers*, edited by Domb, et. al., Hardwood Academic Press, pp. 251-272 (1997). Copoly(ether-esters), for the purpose of this invention, are understood to include those copolyester-ethers as described in the Journal of Biomaterials Research, Vol. 22, pages 993-1009, 1988 by Cohn and Younes, and in Polymer Preprints (ACS Division of Polymer Chemistry), Vol. 30(1), page 498, 1989 by Cohn (e.g. PEO/PLA). Polyalkylene oxalates, for the purpose of this invention, include those described in U.S. Pat. Nos. 4,208,511; 4,141,087; 4,130,639; 4,140,678; 4,105,034; and, 4,205,399. Tyrosine derived polycarbonates, for the purpose of this invention, are understood to include those polymers as described by Pulapura et al., Biopolymers, Vol. 32, Issue 4, pgs 411-417, and Ertel et al., J. Biomed. Mater. Res., 1994, 28, 919-930. For the purpose of this invention, polyphosphazenes, co-, ter- and higher order mixed monomer based polymers made from L-lactide, D, L-lactide, lactic acid, glycolide, glycolic acid, para-dioxanone, trimethylene carbonate and epsilon-caprolactone are understood to include those described by Allcock in *The Encyclopedia of Polymer Science*, Vol. 13, pages 31-41, Wiley Intersciences, John Wiley & Sons, 1988 and by Vandorpe, et al in the *Handbook of Biodegradable Polymers*, edited by Domb, et al, Hardwood Academic Press, pp. 161-182 (1997). Polyesteramides, for the purpose of this invention, are understood to include those polymers as described in United States Patent Application Number 20060188547, and U.S. Pat. No. 5,919,893. Polyanhydrides include those derived from diacids of the form HOOC—$C_6H_4$—O—$(CH_2)_m$—O—$C_6H_4$—COOH, where m is an integer in the range of from 2 to 8, and copolymers thereof with aliphatic alpha-omega diacids of up to 12 carbon atoms. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and, 5,859,150. Polyorthoesters for the purpose of this invention, are understood to include those polymers as described by Heller in *Handbook of Biodegradable Polymers*, edited by Domb, et al, Hardwood Academic Press, pp. 99-118 (1997). Polyurethanes, for the purpose of this invention, are understood to include those polymers as described in U.S. Pat. Nos. 6,326,410; 6,019,996; 5,571,529; and, 4,960,594.

Aliphatic polyesters, for the purpose of this invention, are understood to include, but not be limited to homopolymers and copolymers of lactide (which includes lactic acid D-, L- and meso lactide), glycolide (including glycolic acid), epsilon-caprolactone, p-dioxanone (1,4-dioxan-2-one), trimethylene carbonate (1,3-dioxan-2-one), alkyl derivatives of trimethylene carbonate, such as are described in U.S. Pat. No. 5,412,068, delta-valerolactone, beta-butyrolactone, gamma-butyrolactone, epsilon-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one and combinations thereof.

In one embodiment, the aliphatic polyester is an elastomeric copolymer. "Elastomeric copolymers" are defined as a material that at room temperature can be stretched repeatedly to at least about twice its original length and upon immediate release of stress, will return to approximately its original length. Suitable bioabsorbable, biocompatible elastomers include but are not limited to those selected from the group consisting of elastomeric copolymers of epsilon-caprolactone and glycolide (such as those having a molar ratio of epsilon-caprolactone to glycolide in a range of from about 30:70 to about 70:30, or in a range of from about 35:65 to about 65:35, or in a range of from about 45:55 to 35:65); elastomeric copolymers of epsilon-caprolactone and lactide, including L-lactide, D-lactide blends thereof or lactic acid copolymers (such as those having a molar ratio of epsilon-caprolactone to lactide in a range of from about 35:65 to about 65:35, or in a range of from about 45:55 to 30:70) elastomeric copolymers of p-dioxanone (1,4-dioxan-2-one) and lactide including L-lactide, D-lactide and lactic acid (such as those having a molar ratio of p-dioxanone to lactide in a range of from about 40:60 to about 60:40); elastomeric copolymers of epsilon-caprolactone and p-dioxanone (such as those having a molar ratio of epsilon-caprolactone to p-dioxanone in a range of from about 30:70 to about 70:30); elastomeric copolymers of p-dioxanone and trimethylene carbonate (such as those having a molar ratio of p-dioxanone to trimethylene carbonate in a range of from about 30:70 to about 70:30); elastomeric copolymers of trimethylene carbonate and glycolide (such as those having a molar ratio of trimethylene carbonate to glycolide in a range of from about 30:70 to about 70:30); elastomeric copolymer of trimethylene carbonate and lactide including L-lactide, D-lactide, blends thereof or lactic acid copolymers (such as those having a molar ratio of trimethylene carbonate to lactide in a range of from about 30:70 to about 70:30) and blends thereof. In another embodiment, the elastomeric copolymer is epsilon-caprolactone and glycolide having a molar ratio of epsilon-caprolactone to glycolide in a range of from about 35:65 to about 65:35. In yet another embodiment, the elastomeric copolymer is epsilon-caprolactone and glycolide having a molar ratio of about 35:65.

Examples of suitable non-implantable substrates include, but are not limited to, bandages and wound dressings. As used herein, a "bandage" shall mean a piece of cloth or other material used to bind or wrap a diseased or injured part of the body. Bandages are either placed directly against the wound or used to bind a wound dressing to the wound. As used herein, a "wound dressing" shall mean a piece of cloth or material that is placed directly against the wound and serves the purpose of protecting the wound; promoting healing; and/or providing, retaining, or removing moisture, and is optionally held in place using a bandage.

Non-implantable substrates may be in various forms including but not limited to fabrics, foams, gauze, films, adhesive bandages, hydrocolloids, gels and combinations thereof. These non-implantable substrates may be comprised of any material suitable for application (without implantation) to the body and include, but are not limited to biocompatible, bioabsorbable polymers such as aliphatic polyesters, poly(amino acids), such as poly(L-lysine) and poly(glutamic acid), copoly(ether-esters), polyalkylenes oxalates such as those with alkyl groups having one to ten carbon atoms, polyoxaamides, tyrosine derived polycarbonates, poly(iminocarbonates), polyorthoesters, polyoxaesters, polyesteramides, polyoxaesters containing amine groups, poly(anhydrides), polyphosphazenes, biomolecules (including biopolymers such as collagen, elastin, and gelatin, and polysaccharides, such as starches, alginate, pectin, carboxymethyl cellulose, salts of carboxymethyl cellulose, oxidized regenerated cellulose, and the like) and copolymers and blends thereof, as well as non-bioabsorbable materials include cotton, linen, silk, nylon, such as nylon 6-6 and aromatic polyamides, such as those commercially available from E.I. du Pont de Nemours and Company under the tradenames "KEVLAR" or "NOMEX," polyesters, such as poly(ethylene terephthalate), fluoropolymers such as polyterafluoroethylene, fluorinated poly(ethylene-propylene (FEP) and polyvinylidine fluoride (PFA), polyolefins such as polyethylene and polypropylene, polyurethanes and combinations thereof. These materials are defined as described above.

The CRP-hemostat component may be applied to the surface of such substrates via conventional coating techniques, such as dip coating, spray coating, lyophilization coating, and electrostatic coating techniques. Details of these coating methods are well-known in the art and disclosed in, for example, U.S. Pat. No. 6,669,980; Yun J H, et al., 40(3) ASAIO J. M, 401-5 (July-September 1994); and, Krogars K, et al, *Eur J Pharm Sci.*, 2002 (Oct.), 17 (1-2), 23-30. In general, a solution containing the desired amount of the CRP-hemostat component may be prepared and applied to the surface of the desired substrate via the selected coating technique. The substrate may then be dried via a conventional drying processes including, but not limited to air drying, vacuum drying in a vacuum oven, or lyophilization drying. The CRP should be used in an amount necessary to achieve the desired hemostatic properties, such as blood clotting, platelet aggregation, and the like, but generally the CRP is present for purposes of coating substrates in an amount in a range of from about 0.01 mg/cm$^2$ to about 1 mg/cm$^2$ of substrate, or in a range of from about 0.1 mg/cm$^2$ to about 0.5 mg/cm$^2$, or in a range of about 0.4 mg/cm$^2$.

In another embodiment wherein the substrate is an injectable or sprayable gel or gel-forming liquid, the CRP-hemostat component, which may be in the form of a powder or collagen-like fibrillar substance, may be combined with the injectable or sprayable gel or liquid via conventional mixing techniques known in the art. The injectable or sprayable gel or gel-forming liquid may be comprised of an aqueous salt solution and a gelling material.

Examples of suitable aqueous salt solution include, but are not limited to physiological buffer solution, saline, water, buffered saline, phosphate buffer solution, Hank's balanced salts solution, PBS, Tris buffered saline, Hepes buffered saline, and mixtures thereof. In one embodiment, the aqueous salt solution may be a phosphate buffer solution or PBS.

Examples of suitable gelling materials include, but are not limited to proteins such as, collagen, elastin, thrombin, fibronectin, gelatin, fibrin, tropoelastin, polypeptides, laminin, proteoglycans, fibrin glue, fibrin clot, platelet rich plasma (PRP) clot, platelet poor plasma (PPP) clot, self-assembling peptide hydrogels, and atelocollagen; polysaccharides such as, starch, pectin, cellulose, alkyl cellulose (e.g. methylcellulose), alkylhydroxyalkyl cellulose (e.g. ethylhydroxyethyl cellulose), hydroxyalkyl cellulose (e.g. hydroxylethyl cellulose), cellulose sulfate, salts of carboxymethyl cellulose, carboxymethyl cellulose, carboxyethyl cellulose, chitin, carboxymethyl chitin, hyaluronic acid, salts of hyaluronic acid, alginate, cross-linked alginate alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenans, chitosan, starch, amylose, amylopectin, poly-N-glucosamine, polymannuronic acid, polyglucuronic acid polyglucuronic acid), and derivatives; polynucleotides such as, ribonucleic acids, deoxyribonucleic acids, and others such as, poly(N-isopropylacrylamide), poly(oxyalkylene), copolymers of poly(ethylene oxide)-poly(propylene oxide), poly(vinyl alcohol), polyacrylate, monostearoyl glycerol co-succinate/polyethylene glycol (MGSA/PEG) copolymers and copolymers and combinations thereof.

In defining the cellulose materials described herein, the term "alkyl" refers to a hydrocarbon chain that may be a straight or branched chain containing from about 1 to about 7 carbon atoms, unless indicated otherwise for a particular embodiment, for example methyl, ethyl, propyl, isopropyl, butyl, isobutyl, tert-butyl, pentyl, isopentyl, neopentyl, hexyl, 2,3-dimethylbutyl, neohexyl, or heptyl.

In one embodiment, the gelling material is comprised of polysaccharides. In another embodiment, the gelling material is comprised of sodium carboxymethylcellulose.

The injectable or sprayable gel or liquid may be prepared by dissolving an effective amount of gelling material in the aqueous salt solution to form an initial gel.

An "effective amount" of gelling material is defined as the amount of gelling material sufficiently necessary to allow the injectable or sprayable gel or liquid to be either injected into or sprayed onto the affected area and substantially remain in place after application. Although the effective amount of gelling material will vary depending upon, for example, the gelling material selected, the amount of CRP desired, and the like, one skilled in the art may easily determine an effective amount of gelling material without undue experimentation. In one embodiment, wherein the gelling material is sodium carboxymethylcellulose, the gelling material may be present in an amount, based upon the total weight of the solution, in a range of from about 0.1 percent to about 5 percent, or in a range of from about 0.5 percent to about 3 percent.

The CRP-hemostat component may then be combined with the initial gel by any conventional mixing techniques known in the art including, but not limited to, manual mixing with a spatula, magnetic stirring, or mechanical mixing using a motor and a rotating paddle or blade. In order to minimize possible deleterious affects to the CRP, the mixing temperature should not exceed about 50° C. The CRP-hemostat is present in the resulting gel in an amount effective for inducing hemostasis when applied to a bleeding site, and typically is in a range of, based upon the total weight of the final gel, from about 0.1 mg/mL to about 10 mg/mL, or in a range of from about 0.1 mg/mL to about 1 mg/mL, or about 0.3 mg/mL. In one embodiment, the injectable or sprayable gel or liquid may be in a gel form prior to injection, while in an alternative embodiment, the injectable or sprayable gel or liquid may be in a liquid form prior to injection, but in a gel form and capable of remaining substantially in place upon administration to the desired location.

In embodiments wherein the CRP-hemostat component is in the form of a powder, the CRP may be combined with any suitable powder carrier known in the art. In one embodiment, the carrier may be spray coated onto the powder particles using methods disclosed in, for example, Maa Y F, et al., *SJ Curr Pharm Biotechnol.*, 2000 (Nov.), 1(3), 283-302. The CRP-hemostat component may be present in the powder in an amount, based upon the total powder weight, in a range of from about 0.5 percent to about 100 percent, or in a range of from about 2 percent to about 10 percent.

Examples of suitable powder carriers include, but are not limited to, polysaccharides, such as starch, pectin, cellulose, alkyl cellulose (e.g. methylcellulose), alkylhydroxyalkyl cellulose (e.g. ethylhydroxyethyl cellulose), hydroxyalkyl cellulose (e.g. hydroxylethyl cellulose), cellulose sulfate, salts of carboxymethyl cellulose, carboxymethyl cellulose, carboxyethyl cellulose, chitin, carboxymethyl chitin, hyaluronic acid, salts of hyaluronic acid, alginate, cross-linked alginate alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenans, chitosan, starch, amylose, amylopectin, poly-N-glucosamine, polymannuronic acid, polyglucuronic acid, mannitol, porous lava, polyesters, and copolymers and mixtures thereof.

General CRP Synthesis

The CRPs of the present invention can be made by a variety of solid-phase or solution techniques. For example, although the CRPs can be prepared by other methods (e.g., solution methods) and then attached to a support material for subsequent coupling, it is preferred that standard solid-phase organic synthesis techniques, such as solid-phase polypeptide synthesis (SPPS) techniques be used. That is, a CRP of the present invention can be synthesized, subsequently attached to a support material, coupled with various reagents, and then removed from the support material using a variety of techniques. Preferably, however, the CRP is synthesized on a support material, coupled with reagents, and then removed from a support material using a variety of techniques.

For the preparation of CRPs (oligopeptides, polypeptides, or proteins), solid-phase peptide synthesis involves a covalent attachment step (i.e., anchoring) that links the nascent CRP chain to a support material (typically, an insoluble polymeric support) containing appropriate functional groups for attachment. Subsequently, the anchored CRP is extended by a series of addition (deprotection/coupling) cycles that involve adding N-protected and side-chain-protected amino acids stepwise in the C to N direction. Once chain assembly has been accomplished, protecting groups are removed and the CRP is cleaved from the support. In some cases, other groups are added to the CRP before the protecting groups are removed.

Typically, SPPS begins by using a handle to attach the initial amino acid residue to a functionalized support material. A handle (i.e., linker) is a bifunctional spacer that, on one end, incorporates features of a smoothly cleavable protecting group, and on the other end, a functional group, often a carboxyl group, that can be activated to allow coupling to the functionalized support material. Known handles include acid-labile p-alkoxybenzyl (PAB) handles, photolabile o-nitrobenzyl ester handles, and handles such as those described by Albericio et al., J. Org. Chem., 55, 3730-3743 (1990) and references cited therein, and in U.S. Pat. No. 5,117,009 (Barany) and U.S. Pat. No. 5,196,566 (Barany et al.).

For example, if the support material is prepared with amino-functional monomers, typically, the appropriate handles are coupled quantitatively in a single step onto the amino-functionalized supports to provide a general starting point of well-defined structures for polypeptide chain assembly. The handle protecting group is removed and the C-terminal residue of the N'-protected first amino acid is coupled quantitatively to the handle. Once the handle is coupled to the support material and the initial amino acid is attached to the handle, the general synthesis cycle proceeds. The synthesis cycle generally consists of deprotection of the N-protected amino group of the amino acid on the support material, washing, and, if necessary, a neutralization step, followed by reaction with a carboxyl-activated form of the next N-protected amino acid. The cycle is repeated to form the CRP of interest. Solid-phase peptide synthesis methods using functionalized insoluble support materials are well known.

When SPPS techniques are used to synthesize CRPs on the support material, Fmoc methodologies involve the use of mild orthogonal techniques using the base-labile 9-fluorenylmethyloxycarbonyl (Fmoc) protecting group. Fmoc amino acids can be prepared using fluorenylmethyl succinimidyl carbonate (Fmoc-OSu), Fmoc chloride, or [4-(9-fluorenylmethyloxycarbonyloxy)phenyl]dimethylsulfonium methyl sulfate (Fmoc-ODSP). The Fmoc group can be removed using piperidine in dimethylformamide (DMF) or N-methylpyrrolidone, or using 1,8-diazabicyclo[5.4.0]undec-7-ene (DBU) in DMF. After Fmoc removal, the liberated $N^1$-amine of the supported resin is free and ready for immediate attachment of the lipid without an intervening neutralization step. The immobilized hydrophobic analog of the desired CRP can then be removed, for example, using trifluoroacetic acid (TFA) at room temperature. Such Fmoc solid-phase polypeptide synthesis methodologies are well known to one of skill in the art.

A variety of support materials for preparation of the complexes of the present invention can be used. They can be of inorganic or organic materials and can be in a variety of forms (such as membranes, particles, spherical beads, fibers, gels, glasses, etc.). Examples include, porous glass, silica, polystyrene, polyethylene terephthalate, polydimethylacrylamides, cotton, paper, and the like. Functionalized polystyrenes, such as aminofunctionalized polystyrene, aminomethyl polystyrene, aminoacyl polystyrene, p-methylbenzhydrylamine polystyrene or polyethylene glycol-polystyrene resins may also be used for this purpose.

Specific CRP Synthesis

It is believed that one skilled in the art can, based upon the description herein, utilize the present invention to its fullest extent. The following specific embodiments are to be construed as merely illustrative, and not limitative of the remainder of the disclosure in any way whatsoever.

Materials and Methods: Fmoc-amino acids, HBTU/HOBT, DIEA, NMP and DCM were purchased from Applied Biosystems, Inc. Piperidine was purchased from Sigma-Aldrich. Fmoc-Gly-Wang resin was from Bachem and Fmoc-Phe-Wang resin from Novabiochem. MALDI-TOF mass spectrometry was performed at M-Scan Inc. using an Applied Biosystems Voyager-DE PRO Biospectrometry workstation coupled with a Delayed Extraction laser-desorption mass spectrometer with α-cyano-4-hydroxycinnamic acid as the matrix. Amino acid analysis was performed at the Molecular Structural Facility of U.C. Davis using a Beckman 6300 Li-based amino acid analyzer. The CRPs obtained were >90% pure and the polypeptide content was considered to prepare the solutions for each experiment. Additionally, CRP concentration was confirmed measuring the absorption at 214 ($\epsilon=6.0\times10^4$ $M^{-1}$ $cm^{-1}$ in PBS) or 215 nm ($\epsilon=6.5\times10^4$ $M^{-1}$ $cm^{-1}$ in water). All polypeptide filtrations for electron microscopy experiments were performed using Nuclepore filters (0.4-μm; polycarbonate membrane) from Whatman, the rest of the filtrations were done using Acrodisc syringe filters (0.45-μm; polytetrafluoroethylene membrane) from Pall.

Unless defined otherwise, all technical and scientific terms used herein have the same meaning as commonly understood by one of ordinary skill in the art to which the invention belongs. Abbreviations used in the instant specification are as follows:

| Abbreviation | Meaning |
| --- | --- |
| DCM | dichloromethane |
| Ac | acetyl |
| DIEA | N,N-diisopropylethylamine |
| DBU | 1,8-diazabicyclo[5.4.0]undec-7-ene |
| DMF | dimethylformamide |
| Fmoc | 9-fluorenylmethyloxycarbonyl |
| Fmoc-Osu | fluorenylmethyl succinimidyl carbonate |
| Fmoc-ODSP | [4-(9-fluorenyl-methyloxycarbonyloxy)phenyl]-dimethylsulfonium methyl sulfate |
| HBTU | 2-[(1H-benzotriazol-1-yl)-1,1,3,3-tetramethyluronium hexafluorophosphate |
| HOBT | hydroxybenzotriazole |
| NMP | N-methyl-pyrrolidone |
| PBS | phosphate buffered saline |
| TFA | trifluoroacetic acid |
| $T_m$ | melt temperature |

Example 1

SEQ ID 25: $(F_5)$-Phe-(Gly-Pro-Hyp)$_{10}$-Phe

Comparator SEQ ID 29: Ac-(Gly-Pro-Hyp)$_{10}$-Gly

Comparator SEQ ID 35: $F_5$Phe-(Gly-Pro-Hyp)$_5$-Phe

The CRP having SEQ ID 25 and comparator polypeptides having SEQ ID 29 and SEQ ID 35 were synthesized by standard FastMoc chemistry, purified by reversed-phase HPLC and characterized.

The CRP having SEQ ID 25 was synthesized on an ABI 431 synthesizer using FastMoc chemistry (0.1 mmol scale) and Fmoc-Phe-Wang resin (0.74 mmol/g, 100-200 mesh). The CRP was cleaved from the resin with TFA/triisopropylsilane/water (95:2.5:2.5) for 2 h. HPLC purification was performed in a Phenomenex C-18 reverse-phase column (25×5 cm), using a linear gradient of 10-95% B (A: 0.2% TFA/$H_2O$; B: 0.16% TFA/MeCN) over 60 min at a flow rate of 50 mL/min. The CRP was obtained as a white powder in 32% overall yield. For SEQ ID 25: $(F_5)$-Phe-(Gly-Pro-Hyp)$_{10}$-Phe: MALDI-TOF-MS (M+Na)$^+$ calcd for $C_{138}H_{185}F_5N_{32}O_{43}$, 3096.3; found, 3096.8. The comparator polypeptide having SEQ ID 35: $F_5$Phe-(Gly-Pro-Hyp)$_5$-Phe was synthesized similarly to the CRP having SEQ ID 25: $(F_5)$-Phe-(Gly-Pro-Hyp)$_{10}$-Phe.

The comparator polypeptide having SEQ ID 29: Ac-(Gly-Pro-Hyp)$_{10}$-Gly was synthesized on an ABI 433A synthesizer using FastMoc chemistry (0.1 mmol scale) and Fmoc-Gly-Wang (0.7 mmol/g, 100-200 mesh). The comparator polypeptide was cleaved from the resin with 95% TFA for 2 h. HPLC purification was performed in two Vydac C-18 reverse-phase columns (25×2.5 cm), using a step gradient of 0-100% B over 90 min (A: 0.1% TFA/$H_2O$; B: 80% MeCN/$H_2O$ containing 0.1% TFA) at a flow rate of 6 mL/min. The comparator polypeptide was obtained as a white powder in 34% overall yield. For SEQ ID 29: Ac-(Gly-Pro-Hyp)$_{10}$-Gly: MALDI-TOF-MS (M+Na)$^+$ calcd for $C_{124}H_{177}N_{31}O_{43}$, 2811.3; found, 2812.2.

Circular Dichroism (CD) Spectroscopy

Solutions of the CRP having SEQ ID 25, and comparator polypeptides having SEQ ID 29 and SEQ ID 35 (0.25 mM and 0.013 mM in water) were stored at 4° C. for 24 h and monitored for trimer formation. CD spectra were measured at 25° C. on a Jasco J-710 instrument using 0.1 cm path length cells by signal averaging 10 or 20 scans at a scan speed of 100 nm/min. The CRP having SEQ ID 25 and comparator polypeptide having SEQ ID 29 were found to adopt triple-helical structures by CD spectroscopy (θmax=225 nm). CD melting curves were obtained on an Aviv 215 spectrometer equipped with a Peltier temperature control system. The ellipticity at 225 nm was monitored from 20 to 100° C., at a rate of 1° C./min, with increments of 3° C., equilibration time of 5 min and 0.1-cm path length.

The CRP homotrimer having SEQ ID 25 was determined to have a $T_m$ of about 57° C. The result for the CRP trimer having SEQ ID 25 was confirmed by a temperature-dependent $^1$H NMR study, in which a characteristic downfield shift for the 6-H of proline (originally δ 3.0-3.5 ppm) occurred from about 55° C. to about 65° C. (with equilibration). Thus, the CRP trimer having SEQ ID 25 was stable above room temperature. Comparatively, the thermal stability for the CRP trimer having SEQ ID 25 was slightly higher than that for a recently described collagen-mimetic compound ($T_m$=47° C.) with three peptide strands covalently linked by a pair of disulfide bonds (Kotch F and Raines R T, *Proc. Natl. Acad. Sci. USA* 2006, 103, 3028-3033). The lower melting temperature of the CRP trimer having SEQ ID 25 compared to the reference polypeptide trimer having SEQ ID 29 ($T_m$ 70° C.) may be attributable to some structural disruptions ("fraying") at the ends of the CRP trimer having SEQ ID 25 by the phenyl and pentafluorophenyl groups.

Dynamic Light Scattering (DLS)

DLS measurements were made on a Malvern Zetasizer Zen 1600 instrument equipped with a 633-nm laser (He—Ne, 4.0 mW) and backscatter detection at 173°. Solutions of the CRP having SEQ ID 25 and the reference polypeptide having SEQ ID 29 (0.5 mg/mL in water) were heated at 70° C. for 10 min, filtered hot through a 0.45-μm filter and measured in plastic cuvettes (1.0 cm) when the solutions reached room temperature (at time=0) and after 24 hrs.

DLS measurements were taken to determine the size of the supramolecular composites formed by the CRP having SEQ ID 25 and comparator polypeptide having SEQ ID 29 in water at 25° C. A fresh solution of the CRP having SEQ ID 25 contained two species, sized at 3 nm and 190 nm, which after 24 hrs, converged into an aggregate material with an approximate size of 1000 nm. In contrast, the comparator polypeptide having SEQ ID 29 showed two species with sizes around 4 and 100 nm, which did not increase over the same time period. These results suggest that the hypothesized phenyl-pentafluorophenyl aromatic-stacking mechanism was facilitating the formation of the CRP having SEQ ID 25 into a supramolecular composite.

Transmission Electron Microscopy (TEM)

The size and morphology of the supramolecular composite of the CRP having SEQ ID 25 was also assessed by TEM images taken with a TEM Philips EM 300. Aqueous solutions of the CRP having SEQ ID 25 (0.05 mg/mL) were filtered through 0.4-μm filters and deposited on copper grids coated with carbon films. The solutions were dried at 40° C. and images were recorded at 80 kV. Murine arteries were stained with 2% glutaraldehyde and placed inside epoxy blocks for TEM. Thin sections of the arteries inside the epoxy blocks (around 200-500 nm in size) were cut using a diamond section tool. The sections were mounted on the copper grids and images were recorded at 60 kV. In each experiment, μm-long, composite fibrils (average diameter: 0.26 μm), resembling the collagen fibrils found in murine aortic tissue (average diameter: 0.05 μm), were observed. The fibril dimensions for the CRP having SEQ ID 25 required a combination of end-to-end (linear) and side-to-side (lateral) assembly of at least 100 CRP trimers having SEQ ID 25 in each direction.

Proton NMR Spectroscopy

Proton NMR spectra of the CRP having SEQ ID 25 (1 mM in D$_2$O incubated at 4° C. for 24 h) were collected on a DMX-600 NMR spectrometer (Bruker Biospin, Inc., Billerica, Mass. 01821-3991) equipped with a triple resonance (1H, $^{13}$C, $^{15}$N), triple axis, gradient probe. A one-dimensional NOESY, with presaturation during the recycle delay and the mixing time, was used to collect the data. The temperature was raised in increments of 10° C. and the spectra were measured after 15 min equilibration.

Example 2

SEQ ID 25:   F$_5$Phe-(Gly-Pro-Hyp)$_{10}$-Phe

SEQ ID 26:   Phe-(Gly-Pro-Hyp)$_{10}$-Phe

SEQ ID 27:   Leu-(Gly-Pro-Hyp)$_{10}$-Phe

SEQ ID 28:   Gly-(Gly-Pro-Hyp)$_{10}$-Gly.

The CRPs having SEQ ID 25, SEQ ID 26, and SEQ ID 27 and the comparator polypeptide having SEQ ID 28 were synthesized by standard FastMoc chemistry, purified by reversed-phase HPLC, and characterized.

Peptide Synthesis

The CRPs having SEQ ID 25, SEQ ID 26 and SEQ ID 27 and the comparator polypeptide having SEQ ID 28 were synthesized on an ABI 431 synthesizer using FastMoc chemistry (0.1 mmol scale) and Fmoc-Phe-Wang resin (0.74 mmol/g, 100-200 mesh) or Fmoc-Gly-Wang resin (0.66 mmol/g, 100-200 mesh). The CRPs and polypeptide were cleaved from the resin with TFA/triisopropylsilane/water (95:2.5:2.5) for 2 h. Purification was performed by RP-HPLC (Zorbax 300 SB-C18, 21.2×150 mm, at 60° C.) using a linear gradient of 5-95% B (A: 0.05% TFA/water; B: 0.05% TFA/MeCN) over 15 min at a flow rate of 20 mL/min. The fractions were analyzed by LC/MS on an Agilent 1100 coupled to Finnigan LCQ detector using a Zorbax 300 SB-C18 column (3.5 μm 4.6×150 mm) at 60° C. and a linear gradient of 5-95% B (A: 0.02% formic acid/water; B: 0.02% formic/MeCN) over 20 min at a flow rate of 1 mL/min.

As shown in Table 1, the fractions containing pure (>90%) material were combined and lyophilized to yield the peptides as white powders. Peptide content was determined by measuring the absorption at 215 nm and using the extinction coefficient ($\epsilon$=6.5×10$^4$ M$^{-1}$ cm$^{-1}$) determined for reference peptide SEQ ID 34: (Pro-Hyp-Gly)$_{10}$ (vendor: Peptides International). Calculated and Found MS values were determined using MALDI-TOF-MS (M+Na)$^+$.

TABLE 1

| SEQ ID | Formula | MS Calc'd | MS Found | % Yield | Peptide Content |
|---|---|---|---|---|---|
| 25 | C$_{138}$H$_{185}$F$_5$N$_{32}$O$_{43}$ | 3096.3 | 3096.7 | 31 | 95 |
| 26 | C$_{138}$H$_{190}$N$_{32}$O$_{43}$ | 3006.4 | 3007.0 | 26 | 95 |
| 27 | C$_{135}$H$_{192}$N$_{32}$O$_{43}$ | 2972.4 | 2973.0 | 35 | 96 |
| 28 | C$_{124}$H$_{178}$N$_{32}$O$_{43}$ | 2826.3 | 2826.9 | 32 | 90 |

CRP Analysis

CD Spectroscopy: Solutions of the CRPs having SEQ ID 25, SEQ ID 26 and SEQ ID 27 and the comparator polypeptide having SEQ ID 28 (0.25 mM and 0.013 mM in water) were stored at 4° C. for 24 h and monitored for triple helix formation. CD spectra were measured at 25° C. on a Jasco J-710 instrument using 0.1 cm path length cells by signal averaging 10 or 20 scans at a scan speed of 100 nm/min. CD melting curves were obtained on an Aviv 215 spectrometer equipped with a Peltier temperature control system. The ellipticity at 225 nm was monitored from 20 to 100° C., at a rate of 1° C./min, with increments of 3° C., equilibration time of 5 min and 0.1-cm path length.

The CD spectra of the three CRPs (0.25 mM in water) at 25° C. showed a 225 nm ($\theta_{max}$) band characteristic of a collagen triple helix. The thermal stability of the triple helices formed by the CRPs having SEQ ID 25, SEQ ID 26 and SEQ ID 27 was also comparatively studied by monitoring the ellipticity at 225 nm from 20-100° C., with increments of 3° C. and equilibration time of 5 min. The melting temperatures of the three CRPs were very similar (in the range of 56-59° C.) indicating that, independently of the structural differences at their N-terminuses, they all formed stable trimers.

Example 3

SEQ ID 31:   F$_5$Phe-(Gly-Pro-Hyp)$_9$-Phe

SEQ ID 32:   Phe-(Gly-Pro-Hyp)$_9$-Phe

SEQ ID 33:   Leu-(Gly-Pro-Hyp)$_9$-Phe

As more fully described below, the model structure for a CRP trimer of the present invention was constructed from the X-ray structure of the collagen-like polypeptide trimer having SEQ ID 30: (Pro-Hyp-Gly)$_4$-(Pro-Hyp-Ala)-(Pro-Hyp-Gly)$_5$ (Bella J, Eaton M, Brodsky B and Berman H M, *Science* 1994, 266, 75-81). The collagen-like polypeptide trimer having SEQ ID 30 was mutated to incorporate F$_5$Phe at the N-terminus (Pro-position) and Phe at the C-terminus (Gly-position) to provide a CRP having SEQ ID 31 (similar to SEQ ID 25, but lacking one GPO repeat). Polypeptides having SEQ ID 32 and SEQ ID 33 were similarly prepared using Phe and Leu, respectively.

Computational Chemistry

The crystal structure of the collagen-like polypeptide having SEQ ID 30 was used as the starting point for modeling. Since this structure contained a central alanine residue, the residue was first mutated to glycine. One each of the B and X units of the CRP of Formula (I) were then added to the N-terminus and C-terminus of each strand of the triple helix having SEQ ID 30. On the C-terminus, the Gly residue of SEQ ID 30 was replaced by Phe (for SEQ ID 31, SEQ ID 32 and SEQ ID 33). On the N-terminus, the Pro-Hyp segments were replaced with a single F$_5$Phe (SEQ ID 31), Phe (SEQ ID 32) and Leu (SEQ ID 33).

Due to the nature of the sequence, each of the CRPs having SEQ ID 31, SEQ ID 32 and SEQ ID 33 contained one less repeat of the GPO motif (compared to SEQ ID 25, SEQ ID 26 and SEQ ID 27), but were suitable for molecular modeling of SEQ ID 25, SEQ ID 26 and SEQ ID 27. Each CRP trimer was minimized using a constrained backbone, OPLS-AA force field (Jorgensen W L and Tirado-Rives J, *J. Am. Chem. Soc.* 1988, 110, 1657-1666), GB/SA water (Qui D, Shenkin P S, Hollinger F P and Still C W, *J. Phys. Chem. A.,* 1997, 101, 3005-3014) using Macromodel 9.0 (MacroModel 9.0, 2005, Schrödinger, Inc., 1500 SW First Ave., Suite 1180, Portland, Oreg. 97201) to relax any strain caused by the modifications. Each CRP trimer was then paired with a CRP trimer of the same sequence by aligning two of the trimer units along the trimer central axis. In this step, care was taken to provide a rough alignment of the hydrophobic recognition units.

Each of the aligned CRP trimer pairs having SEQ ID 31, SEQ ID 32 or SEQ ID 33 were evaluated for self-assembly and fibrillar propagation using the XED force field in which each aligned trimer pair was minimized to <0.01 rms (conjugate gradient with no constraints; Hunter C A, Sanders J K M, J. Am. Chem. Soc., 1990, 112, 5525-5534; Vinter J G, J. Comp.-Aid. Mol. Design, 1994, 8, 653-668; Vinter J G, J. Comp.-Aid. Mol. Design, 1996, 10, 417-426; and, Chessari G, Hunter C A, Low C M R, Packer M J, Vinter J G and Zonta C, Chem. Eur. J., 2002, 8, 2860-2867). All carboxylate and ammonium ions were charged at $\frac{1}{8}^{th}$ full charge to account for partial salvation effects. After minimization, the interaction energy (IE) between the two triple helix units was calculated and consisted of both Coulombic and van der Waals components. This energy included all intermolecular terms between each triple helix unit. Intramolecular terms and energies between strands in the same triple-helix bundle were not included. The results for several combinations of recognition elements are summarized in Table 2.

The modelled interface energy for the aligned CRP trimer pair having SEQ ID 31 is shown in (Table 2, entry 1). Three aromatic ring pairs adopted face-to-face orientations and one hydrogen bond was observed at the interface. The structure was tested by reorienting the aromatics in an edge-to-face arrangement and then re-minimizing (Table 2, entry 2). The resulting interface structure reverted back to face-to-face interactions with similar interface energy. The interface of the CRP trimer pair having SEQ ID 32 exhibited either edge-to-face (Table 2, entry 3) or displaced angled face-to-face interactions. The overall interface energies of the CRP trimer pair having SEQ ID 33 was lower (Table 2, entry 4).

TABLE 2

Calculated Interaction Energies for Trimer Pairs (kcal/mol)

| Entry | SEQ ID | Total IE | Coulombic | van der Waals |
|---|---|---|---|---|
| 1 | [1]SEQ ID 31 | −55.2 | −15.0 | −40.2 |
| 2 | [2]SEQ ID 31 | −56.4 | −15.2 | −41.2 |
| 3 | [3]SEQ ID 32 | −49.2 | −7.0 | −42.2 |
| 4 | SEQ ID 33 | −32.5 | −5.6 | −36.9 |

[1]Phe-pentafluorophenylalanine (starting with face to face orientation) model of SEQ ID 31;
[2]Phe-pentafluorophenylalanine (starting T-shaped orientation) model of SEQ ID 31, Minimizes back to face-to-face orientations;
[3]Minimizes towards edge-to-face orientations.

As shown in Table 2, the polypeptides having SEQ ID 31, SEQ ID 32 and SEQ ID 33 have the structural requirements to assemble end-to-end to varying degrees. Analogously, the polypeptides having SEQ ID 25, SEQ ID 26 and SEQ ID 27 would also have the structural requirements to assemble end-to-end similarly.

Example 4

Platelet Aggregation Studies

The ability of the CRP having SEQ ID 25 to mimic collagen's biological function was evaluated in a human platelet aggregation assay. Human platelet-rich plasma (PRP) concentrate from healthy volunteers was purchased from Biological Specialties, Inc. (Colmar, Pa.). The PRP was not older than 5 h, since PRP that was 24 hrs old gave considerably attenuated responses to collagen and a CRP having SEQ ID 25. The PRP was centrifuged at 730 g for 15 min. The resulting platelet pellet was washed twice in CGS buffer (13 mM sodium citrate, 30 mM glucose, 120 mM NaCl, pH 6.5) containing 1 U/mL apyrase (grade V, Sigma-Aldrich) and resuspended in Tyrode's buffer (140 mM NaCl, 2.7 mM KCl, 12 mM $NaHCO_3$, 0.76 mM $Na_2HPO_4$, 5.5 mM dextrose, 5.0 mM Hepes, 0.2% BSA, pH 7.4). The "washed" platelets were diluted to $3 \times 10^8$ platelets/mL and kept >45 min at 37° C. before use.

For the assay, 105 µL of washed platelets, 2 mM $CaCl_2$ and 2.5 mM of fibrinogen were added to a 96-well microtiter plate. Platelet aggregation was initiated by the addition of serial concentrations of native collagen fibrils (equine type I; 92% identity with human collagen sequence; Chrono-log Corp., Havertown, Pa.) or test peptides. Buffer was added to one set of control wells. The assay plate was stirred constantly and intermittently placed in a microplate reader (Softmax, Molecular Devices, Menlo Park, Calif.) to read optical density (650 nm) at 0 and 5 min after the addition of the compound solutions. Aggregation was calculated as the decrease in optical density between the time-0 and 5-min measurements and expressed as percent of aggregation.

The conditions for peptide preparation for platelet aggregation studies are shown in Table 3. Peptides were dissolved in PBS (pH 7) or water (final pH 5) to a concentration of 2 mg/mL. Some samples were heated in a water bath (70° C.) for 10 min, filtered through a 0.45-µm filter and incubated for 24 h or 7 days at 4° C. UV measurements at 215 nm before and after filtration indicated no loss of peptide. Some test solutions of the CRP having SEQ ID 25 in PBS (pH 7) or water were incubated for 24 h or 7 days (4° C.), and other samples were denatured (H+F) and re-annealed at 4° C.

TABLE 3

Conditions for Peptide Preparation and Results for Platelet Aggregation Studies

| Peptide | Solvent | Conditions* | pH | Incubation time | $EC_{50}$ ± SEM (µg/mL) |
|---|---|---|---|---|---|
| Collagen | — | — | — | — | 0.25 ± 0.02 |
| SEQ ID 25 | PBS | — | 7 | 7 days | 0.37 ± 0.06 |
| SEQ ID 25 | PBS | H + F | 7 | 7 days | 2.7 ± 0.20 |
| SEQ ID 25 | PBS | H + F | 7 | 24 h | 9.2 ± 0.82 |
| SEQ ID 25 | Water | — | 5 | 24 h | 1.4 ± 0.27 |
| SEQ ID 34 | PBS | H + F | 7 | 24 h | Not Active |

*H + F represents heated at 70° C. for 10 min and filtered through a 0.45-µm filter The different solutions of the CRPs having SEQ ID 25 induced platelet aggregation, but shorter incubations and "H+F" samples showed decreased potency. The CRP having SEQ ID 25 (untreated, aged 7 days in PBS; $EC_{50}$=0.37 µg/mL) was nearly equipotent with equine type I collagen ($EC_{50}$=0.25 µg/mL), whereas a 30-mer reference polypeptide having SEQ ID 34 (Pro-Hyp-Gly)$_{10}$ failed to aggregate platelets. The peptide of SEQ ID 34 (Pro-Hyp-Gly)$_{10}$ was purchased from Peptides International, Inc.

These results indicate that the CRP trimer having SEQ ID 25 can self-assemble over time into aggregates of appropriate length and conformation to meet the structural requirements for platelet recognition (presumably at platelet collagen receptors). In addition, the self-assembly of a short (8-nm) CRP having SEQ ID 25 by noncovalent means into CRP trimers and then into collagen-like fibrils with collagen-mimetic properties was observed. Notably, micrometer-length, triple-helix-containing, composite fibrils were formed, as determined by CD, DLS, and TEM data. Also, the CRP trimer having SEQ ID 25 acted as a functional protein-like material, with an ability to induce platelet aggregation analogously to collagen. The aromatic-aromatic and hydrophobic-hydrophobic recognition motifs for a CRP of Formula (I) offers a straightforward approach to self-assembly for collagen-mimetic peptides and provides CRP trimers capable of assembling into biologically functional fibrillar structures.

Example 5

Inhibition of platelet aggregation induced by collagen or the CRP trimer having SEQ ID 25 was obtained using integrin GPIIb/IIIa antagonist elarofiban (Hoekstra W J, et al. *J. Med. Chem.* 1999, 42, 5254-5265). Platelet aggregation induced by the CRP trimer having SEQ ID 25 and collagen was inhibited by elarofiban, a GPIIb/IIIa inhibitor.

Washed platelets were incubated with various elarofiban doses (10, 100 and 1000 nM) for 5 min prior to the addition of the CRP trimer having SEQ ID 25 and collagen. A dose-dependent inhibition of platelet aggregation was observed. These data suggest that collagen as well as the CRP trimer having SEQ ID 25 activated platelet aggregation by triggering GPIIb/IIIa signaling.

Example 6

Platelet aggregation induced by collagen or the CRP trimer having SEQ ID 25, SEQ ID 26, SEQ ID 27, SEQ ID 28 and SEQ ID 34 was performed by the methods described in Example 4. In accordance with embodiments of the present invention, FIG. 1 shows that the CRP trimers having SEQ ID 25, SEQ ID 26 and SEQ ID 27 stimulated the aggregation of platelets to varying degrees, with the CRP trimer having SEQ ID 25 and the CRP trimer having SEQ ID 26 being more potent. Reference polypeptides having SEQ ID 28, SEQ ID 34 and SEQ ID 35 were not effective in stimulating platelet aggregation. The FIG. 1 $EC_{50}$ values (±SEM) (μg/mL) obtained for collagen and the CRP trimers having SEQ ID 25, SEQ ID 26 and SEQ ID 27 are shown in Table 4.

TABLE 4

| $EC_{50}$ values (±SEM) (μg/mL) | |
|---|---|
| Peptide | $EC_{50}$ |
| Collagen | 0.56 ± 0.09 |
| SEQ ID 25 | 2.44 ± 0.20 |
| SEQ ID 26 | 13.06 ± 1.28 |
| SEQ ID 27 | >30 |

Example 7

CRP Coated and PBS Control Coated PCL/PGA Foam in a Spleen Injury Model

Step A. CRP Suspension

A test suspension was prepared by dissolving the CRP having SEQ ID 25 in phosphate buffered saline ("PBS") having pH 7.4 at a concentration of 0.33 mg of CRP/mL of PBS, and then incubating the suspension for 7 days at 4° C.

Step B. Preparation of PCL/PGA Substrate Foam

A 3 mm thick poly(epsilon-caprolactone-co-glycolide) ("PCL/PGA foam") was prepared by lyophilizing 50 grams of a 3 weight percent solution of 35/65 (mol/mol) PCL/PGA in 1,4-dioxane in a 4.5"×4.5" aluminum mold under temperature conditions of from about 5 to about −5° C. for about 3 hours in a freeze dryer (FTS Systems, Model TD3B2T5100). The resulting PCL/PGA foam was removed from the mold, then cut into several 2"×2" squares.

Step C. Preparation of Polypeptide Coated Foam

A PCL/PGA foam square prepared in accordance with the procedure set forth in Step B above was placed into 2"×2" aluminum mold. After mixing the CRP suspension prepared in accordance with the procedure set forth in Step A above until it appeared to be homogeneous, 7 mLs of the suspension was then poured into the mold in order to substantially cover the top surface of the foam. The mold was then placed into a freeze dryer (FTS Systems, Model TD3B2T5100), pre-cooled to −50° C., and lyophilized at −25° C. for about 44 hours.

Step D. Preparation of PBS Coated Control Foam

PBS coated foams were prepared by adding 7 mL of PBS to a 2"×2" mold containing a 3 mm thick PCL/PGA foam prepared in accordance with the procedure set forth in Step B above in order to substantially cover the top surface of the foam. The mold was placed into a freeze dryer (FTS Systems, Model TD3B2T5100), pre-cooled to −50° C., and lyophilized at −25° C. for about 44 hours.

The CRP coated foam and the PBS coated control foam was then cut into several 2 cm×3 cm pieces for subsequent testing.

Spleen Injury Model

Two linear lacerations (each of which were 1 cm long and 0.3 cm deep) were made on the spleen of a swine. After the wounds were allowed to bleed for about 3 to 5 seconds, a CRP coated foam piece produced in accordance with Step C was applied by hand to the surface of one wound (Test Group 1), and a PBS coated control foam piece prepared in accordance with Step D was applied by hand to the surface of the other wound (Test Group 2). Similar downward pressure was then applied to each of the test sites for 30 seconds. After removal of the coated foam piece, each respective wound was evaluated visually to determine if hemostasis was achieved. If necessary, pressure was reapplied on each wound, respectively, with a clean coated foam piece of a similar type for 30 second intervals. The time to achieve hemostasis, the stopping of bleeding, for each wound is shown in Table 5 below

TABLE 5

| | Time to Hemostasis (sec) | |
|---|---|---|
| | Test Group 1 | Test Group 2 |
| Pieces Applied | 2 | 2 |
| Time | 95 +/− 65 | 170 +/− 70 |

The results indicate that the CRP coated foam was useful in achieving hemostasis in less time than the control foam.

While the foregoing specification teaches the principles of the present invention, with examples provided for the purpose of illustration, it will be understood that the practice of the invention encompasses all of the usual variations, adaptations and/or modifications as come within the scope of the following claims and their equivalents. As well, all publications, patent applications, patents, and other references disclosed in the above specification are hereby incorporated by reference in their entirety and for all purposes.

We claim:

1. A composition comprised of a collagen-related peptide of Formula (I):

$$B\text{-}(Z)_m\text{-}X$$

wherein

Z is selected from the group consisting of Gly-Pro-J, Pro-J-Gly and J-Gly-Pro;

J is selected from the group consisting of Hyp, fPro, mPro and Pro;

m is an integer selected from 8, 9, 10, 11, 12, 13, 14 or 15; and,

B and X are independently selected from the group consisting of $F_5$-Phe, Phe wherein the phenyl ring is mono or disubstituted with fluoro, chloro, bromo, hydroxyl, methyl or $CF_3$, Tyr, 3,4-$(OH)_2$-Phe, MeO-Tyr, phenylglycine, 2-naphthyl-Ala, 1-naphthyl-Ala, Trp, Cha, Chg, Met, Leu, Ile and Val, wherein the composition is in the form of a foam, a powder, a fiber, or a film, wherein the composition comprises a plurality of said collagen-related peptides, wherein the collagen-related peptides are present in the form of a plurality of collagen-related peptide trimers, and wherein the collagen-related peptide trimers are homotrimers or heterotrimers.

2. The composition of claim 1, wherein the composition is in the form of a foam and further comprises, based upon the total dry weight of the foam, from about 0.1 percent to about 15 percent of a plasticizer.

3. The composition of claim 2, wherein the plasticizer is selected from the group consisting of glycerol; polyethylene glycol; glycerin; propylene glycol; monoacetate of glycerol; diacetate of glycerol; triacetate of glycerol; and mixtures thereof.

4. The composition of claim 1, wherein the composition is in the form of a foam having a thickness of about 0.5 mm to about 10 mm.

5. The composition of claim 1, wherein the composition is in the form of a foam having a pore size of from about 1 micron to about 500 microns.

6. The composition of claim 1, wherein the composition is in the form of a film having a thickness of about 50 microns to about 150 microns.

7. The composition of claim 1, wherein the composition is in the form of a powder and the powder has a particle size of about 1 micron to about 2000 microns.

8. The composition of claim 7 further comprising a carrier selected from polysaccharides; mannitol; porous lava; polyesters; and copolymers and mixtures thereof.

9. The composition of claim 8, wherein the polysaccharide is selected from the group consisting of starch; pectin; cellulose; alkyl cellulose wherein the alkyl group has from about 1 to about 7 carbon atoms; alkylhydroxyalkyl cellulose wherein the alkyl group has from about 1 to about 7 carbon atoms; hydroxyalkyl cellulose wherein the alkyl group has from about 1 to about 7 carbon atoms; cellulose sulfate; salts of carboxymethyl cellulose; carboxymethyl cellulose; carboxyethyl cellulose; chitin; carboxymethyl chitin; hyaluronic acid; salts of hyaluronic acid; alginate; cross-linked alginate; alginic acid; propylene glycol alginate; glycogen; dextran; dextran sulfate; curdlan; pectin; pullulan; xanthan; chondroitin; chondroitin sulfates; carboxymethyl dextran; carboxymethyl chitosan; chitosan; heparin; heparin sulfate; heparin; heparan sulfate; dermatan sulfate; keratan sulfate; carrageenans; chitosan; starch; amylose; amylopectin; poly-N-glucosamine; polymannuronic acid; polyglucuronic acid; and copolymers and mixtures thereof.

10. A method of enhancing hemostasis in an individual in need thereof comprised of applying the composition of claim 1 to at least one bleeding site on the individual.

11. A composition comprised of
(a) a collagen-related peptide of Formula (I):

$$B\text{-}(Z)m\text{-}X$$

wherein
Z is selected from the group consisting of Gly-Pro-J, Pro-J-Gly and J-Gly-Pro;
J is selected from the group consisting of Hyp, fPro, mPro and Pro;
m is an integer selected from 8, 9, 10, 11, 12, 13, 14 or 15; and,
B and X are independently selected from the group consisting of $F_5$-Phe, Phe wherein the phenyl ring is mono or disubstituted with fluoro, chloro, bromo, hydroxyl, methyl or $CF_3$, Tyr, 3,4-$(OH)_2$-Phe, MeO-Tyr, phenylglycine, 2-naphthyl-Ala, 1-naphthyl-Ala, Tip, Cha, Chg, Met, Leu, Ile and Val; and
(b) a substrate,
wherein the composition comprises a plurality of said collagen-related peptides, wherein the collagen-related peptides are present in the form of a plurality of collagen-related peptide trimers, and wherein the collagen-related peptide trimers are homotrimers or heterotrimers.

12. The composition of claim 11, wherein the substrate is suitable for implantation into a human body.

13. The composition of claim 12, wherein the substrate is a suture anchor, suture, staple, surgical tack, clip, plate, screw, film; tissue engineering scaffold; foam or powder.

14. The composition of claim 11, wherein the substrate is comprised of a polymer selected from the group consisting of aliphatic polyesters, poly(amino acids), copoly(ether-esters), polyalkylenes oxalates wherein the alkyl group has from about 1 to about 10 carbon atoms, polyamides, tyrosine derived polycarbonates, poly(iminocarbonates), polyorthoesters, polyoxaesters, polyamidoesters, polyoxyesters containing amine groups, poly(anhydrides), polyphosphazenes, collagen, elastin, gelatin, polysaccharides, and copolymers and blends thereof.

15. The composition of claim 11, wherein the substrate is comprised of a material selected from the group consisting of cotton, linen, silk, nylon, polyesters, fluoropolymers, polyolefins, polyurethanes and copolymers and combinations thereof.

16. The composition of claim 11, wherein the substrate is a substrate that is not to be implanted into a human body.

17. The composition of claim 16, wherein the substrate is a bandage, an adhesive bandage, or a wound dressing.

18. The composition of claim 11, wherein the collagen-related peptide is present in the composition in an amount, based upon the total surface area of the substrate, from about 0.01 mg/cm² to about 1 mg/cm².

19. The composition of claim 11, wherein the collagen-related peptide is present in the composition in an amount, based upon the total surface area of the substrate, from about 0.1 mg/cm² to about 0.5 mg/cm².

20. The composition of claim 11, wherein the substrate is a foam comprised of a copolymer of epsilon-caprolactone and glycolide.

21. A method of enhancing hemostasis in an individual in need thereof comprised of applying the composition of claim 11 to a bleeding site on the individual.

22. A method of enhancing hemostasis in an individual in need thereof comprised of applying the composition of claim 20 to a bleeding site on the individual.

23. A gel comprised of:
a) a collagen-related peptide of Formula (I):

$$B\text{-}(Z)m\text{-}X$$

wherein
Z is selected from the group consisting of Gly-Pro-J, Pro-J-Gly and J-Gly-Pro;
J is selected from the group consisting of Hyp, fPro, mPro and Pro;
m is an integer selected from 8, 9, 10, 11, 12, 13, 14 or 15; and,
B and X are independently selected from the group consisting of $F_5$-Phe, Phe wherein the phenyl ring is mono or disubstituted with fluoro, chloro, bromo, hydroxyl, methyl or $CF_3$, Tyr, 3,4-$(OH)2$-Phe, MeO-Tyr, phenylglycine, 2-naphthyl-Ala, 1-naphthyl-Ala, Trp, Cha, Chg, Met, Leu, Ile and Val; and
b) a gelling agent, wherein the collagen-related peptide is present in the gel in an amount, based upon the total weight of the gel, from about 0.1 mg/ml to about 10 mg/mL
wherein the composition comprises a plurality of said collagen-related peptides, wherein the collagen-related peptides are present in the form of a plurality of collagen-related peptide trimers, and wherein the collagen-related peptide trimers are homotrimers or heterotrimers.

24. A method of enhancing hemostasis in an individual in need thereof comprised of applying the gel of claim 23 to a bleeding site on the individual.

25. A composition comprised of:
a) a collagen-related peptide of Formula (I):

$$B\text{-}(Z)m\text{-}X$$

wherein
Z is selected from the group consisting of Gly-Pro-J, Pro-J-Gly and J-Gly-Pro;
J is selected from the group consisting of Hyp, fPro, mPro and Pro;
m is an integer selected from 8, 9, 10, 11, 12, 13, 14 or 15; and,
B and X are independently selected from the group consisting of $F_5$-Phe, Phe wherein the phenyl ring is mono or disubstituted with fluoro, chloro, bromo, hydroxyl, methyl or $CF_3$, Tyr, 3,4-$(OH)_2$-Phe, MeO-Tyr, phenylglycine, 2-naphthyl-Ala, 1-naphthyl-Ala, Trp, Cha, Chg, Met, Leu, Ile and Val; and
b) at least one excipient.

26. A medical device comprised of the composition of claim 1.

27. A medical device comprised of the composition of claim 11.

28. A medical device comprised of the composition of claim 23.

29. A medical device comprised of the composition of claim 25.

30. A method of treating bleeding disorders in an individual in need thereof comprising using a collagen-related peptide of Formula (I): B-(Z)mX wherein
Z is selected from the group consisting of Gly-Pro-J, Pro-J-Gly and J-Gly-Pro;
J is selected from the group consisting of Hyp, fPro, mPro and Pro;

m is an integer selected from 8, 9, 10, 11, 12, 13, 14 or 15; and,

B and X are independently selected from the group consisting of $F_5$-Phe, Phe wherein the phenyl ring is mono or disubstituted with fluoro, chloro, bromo, hydroxyl, methyl or $CF_3$, Tyr, 3,4-$(OH)_2$-Phe, MeO-Tyr, phenylglycine, 2-naphthyl-Ala, 1-naphthyl-Ala, Trp, Cha, Chg, Met, Leu, Ile and Val;

in an amount effective for initiating platelet aggregation on a desired site in said individual.

31. A method of diagnosing bleeding disorders in an individual in need thereof comprising (a) combining a collagen-related peptide of Formula (I):

B-(Z)m-X wherein

Z is selected from the group consisting of Gly-Pro-J, Pro-J-Gly and J-Gly-Pro;

J is selected from the group consisting of Hyp, fPro, mPro and Pro;

m is an integer selected from 8, 9, 10, 11, 12, 13, 14 or 15; and,

B and X are independently selected from the group consisting of $F_5$-Phe, Phe wherein the phenyl ring is mono or disubstituted with fluoro, chloro, bromo, hydroxyl, methyl or $CF_3$, Tyr, 3,4-$(OH)_2$-Phe, MeO-Tyr, phenylglycine, 2-naphthyl-Ala, 1-naphthyl-Ala, Trp, Cha, Chg, Met, Leu, Ile and Val;

with blood or plasma containing platelets from said individual to form a mixture; then (b) adding the mixture to a platelet aggregometer in order to evaluate platelet aggregation in said mixture.

32. A composition comprised of:

(a) a collagen-related peptide of Formula (I):

B-(Z)m-X wherein

Z is selected from the group consisting of Gly-Pro-J, Pro-J-Gly and J-Gly-Pro;

J is selected from the group consisting of Hyp, fPro, mPro and Pro;

m is an integer selected from 8, 9, 10, 11, 12, 13, 14 or 15; and,

B and X are independently selected from the group consisting of $F_5$-Phe, Phe wherein the phenyl ring is mono or disubstituted with fluoro, chloro, bromo, hydroxyl, methyl or $CF_3$, Tyr, 3,4-$(OH)_2$-Phe, MeO-Tyr, phenylglycine, 2-naphthyl-Ala, 1-naphthyl-Ala, Trp, Cha, Chg, Met, Leu, Ile and Val; and (b) a pharmaceutically active agent.

33. The composition of claim 32, wherein the pharmaceutically active agent is selected from the group consisting of hemostatics, antiinfectives, analgesics, antiinflammatory agents, and combinations thereof.

34. The composition of claim 33, wherein the hemostatics are selected from the group consisting of thrombin, fibrinogen, ADP, ATP, calcium, magnesium, $TXA_2$, serotonin, epinephrine, platelet factor 4, factor V, factor EI, PAI-1, thrombospondin and combinations thereof.

35. The composition of claim 33, wherein the antiinfectives are selected from the group consisting of antibodies, antigens, antibiotics, antiviral agents, and combinations thereof.

36. The composition of claim 33, wherein the anti-inflammatory agent is an antihistamine.

37. A composition comprising a chemically defined three-dimensional polymer matrix supplemented with a collagen-related peptide of Formula (I):

B-(Z)m-X wherein

Z is selected from the group consisting of Gly-Pro-J, Pro-J-Gly and J-Gly-Pro;

J is selected from the group consisting of Hyp, fPro, mPro and Pro;

m is an integer selected from 8, 9, 10, 11, 12, 13, 14 or 15; and,

B and X are independently selected from the group consisting of $F_5$-Phe, Phe wherein the phenyl ring is mono or disubstituted with fluoro, chloro, bromo, hydroxyl, methyl or $CF_3$, Tyr, 3,4-$(OH)_2$-Phe, MeO-Tyr, phenylglycine, 2-naphthyl-Ala, 1-naphthyl-Ala, Trp, Cha, Chg, Met, Leu, Ile and Val.

* * * * *

SEQUENCE LISTING

<160> NUMBER OF SEQ ID NOS: 47

<210> SEQ ID NO 1
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<221> NAME/KEY: MOD_RES
<222> LOCATION: (4)..(4)
<223> OTHER INFORMATION: Hyp
<220> FEATURE:
<221> NAME/KEY: MOD_RES
<222> LOCATION: (7)..(7)
<223> OTHER INFORMATION: Hyp
<220> FEATURE:
<221> NAME/KEY: MOD_RES
<222> LOCATION: (10)..(10)
<223> OTHER INFORMATION: Hyp
<220> FEATURE:
<221> NAME/KEY: MOD_RES
<222> LOCATION: (13)..(13)
<223> OTHER INFORMATION: Hyp
<220> FEATURE:
<221> NAME/KEY: MOD_RES
<222> LOCATION: (16)..(16)
<223> OTHER INFORMATION: Hyp, fPro, mPro or Pro
<220> FEATURE:
<221> NAME/KEY: MOD_RES
<222> LOCATION: (19)..(19)
<223> OTHER INFORMATION: Hyp, fPro, mPro or Pro
<220> FEATURE:
<221> NAME/KEY: MOD_RES
<222> LOCATION: (22)..(22)
<223> OTHER INFORMATION: Hyp, fPro, mPro or Pro
<220> FEATURE:
<221> NAME/KEY: MOD_RES
<222> LOCATION: (25)..(25)
<223> OTHER INFORMATION: Hyp, fPro, mPro or Pro
<220> FEATURE:
<221> NAME/KEY: MOD_RES
<222> LOCATION: (28)..(28)
<223> OTHER INFORMATION: Hyp, fPro, mPro or Pro
<220> FEATURE:
<221> NAME/KEY: MOD_RES
<222> LOCATION: (31)..(31)
<223> OTHER INFORMATION: Hyp, fPro, mPro or Pro
<220> FEATURE:
<221> NAME/KEY: MOD_RES
<222> LOCATION: (34)..(34)
<223> OTHER INFORMATION: Hyp, fPro, mPro or Pro
<220> FEATURE:
<221> NAME/KEY: MOD_RES
<222> LOCATION: (37)..(37)
<223> OTHER INFORMATION: Hyp, fPro, mPro or Pro
<220> FEATURE:
<221> NAME/KEY: MOD_RES
<222> LOCATION: (40)..(40)
<223> OTHER INFORMATION: Hyp, fPro, mPro or Pro
<220> FEATURE:
<221> NAME/KEY: MOD_RES
<222> LOCATION: (43)..(43)
<223> OTHER INFORMATION: Hyp, fPro, mPro or Pro
<220> FEATURE:
<221> NAME/KEY: MOD_RES
<222> LOCATION: (46)..(46)
<223> OTHER INFORMATION: Hyp, fPro, mPro or Pro
<220> FEATURE:

```
<221> NAME/KEY: misc_feature
<222> LOCATION: (14)..(46)
<223> OTHER INFORMATION: This region may encompass 4 to 11 "Gly Pro Xaa"
      repeating units
<220> FEATURE:
<221> NAME/KEY: MOD_RES
<222> LOCATION: (47)..(47)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<223> OTHER INFORMATION: see specification as filed for detailed
      description of substitutions and preferred embodiments

<400> SEQUENCE: 1

Xaa Gly Pro Xaa Gly Pro Xaa Gly Pro Xaa Gly Pro Xaa Gly Pro Xaa
1               5                   10                  15

Gly Pro Xaa Gly Pro Xaa Gly Pro Xaa Gly Pro Xaa Gly Pro Xaa Gly
            20                  25                  30

Pro Xaa Gly Pro Xaa Gly Pro Xaa Gly Pro Xaa Gly Pro Xaa Xaa
        35                  40                  45

<210> SEQ ID NO 2
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<221> NAME/KEY: MOD_RES
<222> LOCATION: (4)..(4)
<223> OTHER INFORMATION: Hyp
<220> FEATURE:
<221> NAME/KEY: MOD_RES
<222> LOCATION: (7)..(7)
<223> OTHER INFORMATION: Hyp
<220> FEATURE:
<221> NAME/KEY: MOD_RES
<222> LOCATION: (10)..(10)
<223> OTHER INFORMATION: Hyp
<220> FEATURE:
<221> NAME/KEY: MOD_RES
<222> LOCATION: (13)..(13)
<223> OTHER INFORMATION: Hyp
<220> FEATURE:
<221> NAME/KEY: MOD_RES
<222> LOCATION: (16)..(16)
<223> OTHER INFORMATION: Hyp
<220> FEATURE:
<221> NAME/KEY: MOD_RES
<222> LOCATION: (19)..(19)
<223> OTHER INFORMATION: Hyp
<220> FEATURE:
<221> NAME/KEY: MOD_RES
<222> LOCATION: (22)..(22)
<223> OTHER INFORMATION: Hyp
<220> FEATURE:
<221> NAME/KEY: MOD_RES
<222> LOCATION: (25)..(25)
<223> OTHER INFORMATION: Hyp
<220> FEATURE:
<221> NAME/KEY: MOD_RES
<222> LOCATION: (28)..(28)
<223> OTHER INFORMATION: Hyp, fPro, mPro or Pro
<220> FEATURE:
<221> NAME/KEY: MOD_RES
<222> LOCATION: (31)..(31)
```

```
<223> OTHER INFORMATION: Hyp, fPro, mPro or Pro
<220> FEATURE:
<221> NAME/KEY: MOD_RES
<222> LOCATION: (34)..(34)
<223> OTHER INFORMATION: Hyp, fPro, mPro or Pro
<220> FEATURE:
<221> NAME/KEY: MOD_RES
<222> LOCATION: (37)..(37)
<223> OTHER INFORMATION: Hyp, fPro, mPro or Pro
<220> FEATURE:
<221> NAME/KEY: MOD_RES
<222> LOCATION: (40)..(40)
<223> OTHER INFORMATION: Hyp, fPro, mPro or Pro
<220> FEATURE:
<221> NAME/KEY: MOD_RES
<222> LOCATION: (43)..(43)
<223> OTHER INFORMATION: Hyp, fPro, mPro or Pro
<220> FEATURE:
<221> NAME/KEY: MOD_RES
<222> LOCATION: (46)..(46)
<223> OTHER INFORMATION: Hyp, fPro, mPro or Pro
<220> FEATURE:
<221> NAME/KEY: misc_feature
<222> LOCATION: (26)..(46)
<223> OTHER INFORMATION: This region may encompass 0 to 7 "Gly Pro Xaa"
      repeating units
<220> FEATURE:
<221> NAME/KEY: MOD_RES
<222> LOCATION: (47)..(47)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<223> OTHER INFORMATION: see specification as filed for detailed
      description of substitutions and preferred embodiments

<400> SEQUENCE: 2

Xaa Gly Pro Xaa Gly Pro Xaa Gly Pro Xaa Gly Pro Xaa Gly Pro Xaa
1               5                   10                  15

Gly Pro Xaa Gly Pro Xaa Gly Pro Xaa Gly Pro Xaa Gly Pro Xaa Gly
            20                  25                  30

Pro Xaa Gly Pro Xaa Gly Pro Xaa Gly Pro Xaa Gly Pro Xaa Xaa
        35                  40                  45

<210> SEQ ID NO 3
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<221> NAME/KEY: MOD_RES
<222> LOCATION: (4)..(4)
<223> OTHER INFORMATION: Hyp
<220> FEATURE:
<221> NAME/KEY: MOD_RES
<222> LOCATION: (7)..(7)
<223> OTHER INFORMATION: Hyp
<220> FEATURE:
<221> NAME/KEY: MOD_RES
<222> LOCATION: (10)..(10)
<223> OTHER INFORMATION: Hyp
<220> FEATURE:
<221> NAME/KEY: MOD_RES
<222> LOCATION: (13)..(13)
<223> OTHER INFORMATION: Hyp
<220> FEATURE:
```

```
<221> NAME/KEY: MOD_RES
<222> LOCATION: (16)..(16)
<223> OTHER INFORMATION: Hyp
<220> FEATURE:
<221> NAME/KEY: MOD_RES
<222> LOCATION: (19)..(19)
<223> OTHER INFORMATION: Hyp
<220> FEATURE:
<221> NAME/KEY: MOD_RES
<222> LOCATION: (22)..(22)
<223> OTHER INFORMATION: Hyp
<220> FEATURE:
<221> NAME/KEY: MOD_RES
<222> LOCATION: (25)..(25)
<223> OTHER INFORMATION: Hyp
<220> FEATURE:
<221> NAME/KEY: MOD_RES
<222> LOCATION: (28)..(28)
<223> OTHER INFORMATION: Hyp
<220> FEATURE:
<221> NAME/KEY: MOD_RES
<222> LOCATION: (31)..(31)
<223> OTHER INFORMATION: Hyp
<220> FEATURE:
<221> NAME/KEY: MOD_RES
<222> LOCATION: (34)..(34)
<223> OTHER INFORMATION: Hyp
<220> FEATURE:
<221> NAME/KEY: MOD_RES
<222> LOCATION: (37)..(37)
<223> OTHER INFORMATION: Hyp
<220> FEATURE:
<221> NAME/KEY: MOD_RES
<222> LOCATION: (40)..(40)
<223> OTHER INFORMATION: Hyp, fPro, mPro or Pro
<220> FEATURE:
<221> NAME/KEY: MOD_RES
<222> LOCATION: (43)..(43)
<223> OTHER INFORMATION: Hyp, fPro, mPro or Pro
<220> FEATURE:
<221> NAME/KEY: MOD_RES
<222> LOCATION: (46)..(46)
<223> OTHER INFORMATION: Hyp, fPro, mPro or Pro
<220> FEATURE:
<221> NAME/KEY: misc_feature
<222> LOCATION: (38)..(46)
<223> OTHER INFORMATION: This region may encompass 0 to 3 "Gly Pro Xaa"
      repeating units
<220> FEATURE:
<221> NAME/KEY: MOD_RES
<222> LOCATION: (47)..(47)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<223> OTHER INFORMATION: see specification as filed for detailed
      description of substitutions and preferred embodiments

<400> SEQUENCE: 3

Xaa Gly Pro Xaa Gly Pro Xaa Gly Pro Xaa Gly Pro Xaa Gly Pro Xaa
1               5                   10                  15

Gly Pro Xaa Gly Pro Xaa Gly Pro Xaa Gly Pro Xaa Gly Pro Xaa Gly
            20                  25                  30

Pro Xaa Gly Pro Xaa Gly Pro Xaa Gly Pro Xaa Gly Pro Xaa Xaa
        35                  40                  45

<210> SEQ ID NO 4
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (1)..(1)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<221> NAME/KEY: MOD_RES
<222> LOCATION: (3)..(3)
<223> OTHER INFORMATION: Hyp
<220> FEATURE:
<221> NAME/KEY: MOD_RES
<222> LOCATION: (6)..(6)
<223> OTHER INFORMATION: Hyp
<220> FEATURE:
<221> NAME/KEY: MOD_RES
<222> LOCATION: (9)..(9)
<223> OTHER INFORMATION: Hyp
<220> FEATURE:
<221> NAME/KEY: MOD_RES
<222> LOCATION: (12)..(12)
<223> OTHER INFORMATION: Hyp
<220> FEATURE:
<221> NAME/KEY: MOD_RES
<222> LOCATION: (15)..(15)
<223> OTHER INFORMATION: Hyp, fPro, mPro or Pro
<220> FEATURE:
<221> NAME/KEY: MOD_RES
<222> LOCATION: (18)..(18)
<223> OTHER INFORMATION: Hyp, fPro, mPro or Pro
<220> FEATURE:
<221> NAME/KEY: MOD_RES
<222> LOCATION: (21)..(21)
<223> OTHER INFORMATION: Hyp, fPro, mPro or Pro
<220> FEATURE:
<221> NAME/KEY: MOD_RES
<222> LOCATION: (24)..(24)
<223> OTHER INFORMATION: Hyp, fPro, mPro or Pro
<220> FEATURE:
<221> NAME/KEY: MOD_RES
<222> LOCATION: (27)..(27)
<223> OTHER INFORMATION: Hyp, fPro, mPro or Pro
<220> FEATURE:
<221> NAME/KEY: MOD_RES
<222> LOCATION: (30)..(30)
<223> OTHER INFORMATION: Hyp, fPro, mPro or Pro
<220> FEATURE:
<221> NAME/KEY: MOD_RES
<222> LOCATION: (33)..(33)
<223> OTHER INFORMATION: Hyp, fPro, mPro or Pro
<220> FEATURE:
<221> NAME/KEY: MOD_RES
<222> LOCATION: (36)..(36)
<223> OTHER INFORMATION: Hyp, fPro, mPro or Pro
<220> FEATURE:
<221> NAME/KEY: MOD_RES
<222> LOCATION: (39)..(39)
<223> OTHER INFORMATION: Hyp, fPro, mPro or Pro
<220> FEATURE:
<221> NAME/KEY: MOD_RES
<222> LOCATION: (42)..(42)
<223> OTHER INFORMATION: Hyp, fPro, mPro or Pro
<220> FEATURE:
<221> NAME/KEY: MOD_RES
<222> LOCATION: (45)..(45)
<223> OTHER INFORMATION: Hyp, fPro, mPro or Pro
<220> FEATURE:
<221> NAME/KEY: misc_feature
<222> LOCATION: (14)..(46)
<223> OTHER INFORMATION: This region may encompass 4 to 11 "Pro Xaa Gly"
      repeating units
<220> FEATURE:
<221> NAME/KEY: MOD_RES
<222> LOCATION: (47)..(47)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<223> OTHER INFORMATION: see specification as filed for detailed
      description of substitutions and preferred embodiments
```

-continued

```
<400> SEQUENCE: 4

Xaa Pro Xaa Gly Pro Xaa Gly Pro Xaa Gly Pro Xaa Gly Pro Xaa Gly
1               5                   10                  15

Pro Xaa Gly Pro Xaa Gly Pro Xaa Gly Pro Xaa Gly Pro Xaa Gly Pro
            20                  25                  30

Xaa Gly Pro Xaa Gly Pro Xaa Gly Pro Xaa Gly Pro Xaa Gly Xaa
        35                  40                  45

<210> SEQ ID NO 5
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<221> NAME/KEY: MOD_RES
<222> LOCATION: (3)..(3)
<223> OTHER INFORMATION: Hyp
<220> FEATURE:
<221> NAME/KEY: MOD_RES
<222> LOCATION: (6)..(6)
<223> OTHER INFORMATION: Hyp
<220> FEATURE:
<221> NAME/KEY: MOD_RES
<222> LOCATION: (9)..(9)
<223> OTHER INFORMATION: Hyp
<220> FEATURE:
<221> NAME/KEY: MOD_RES
<222> LOCATION: (12)..(12)
<223> OTHER INFORMATION: Hyp
<220> FEATURE:
<221> NAME/KEY: MOD_RES
<222> LOCATION: (15)..(15)
<223> OTHER INFORMATION: Hyp
<220> FEATURE:
<221> NAME/KEY: MOD_RES
<222> LOCATION: (18)..(18)
<223> OTHER INFORMATION: Hyp
<220> FEATURE:
<221> NAME/KEY: MOD_RES
<222> LOCATION: (21)..(21)
<223> OTHER INFORMATION: Hyp
<220> FEATURE:
<221> NAME/KEY: MOD_RES
<222> LOCATION: (24)..(24)
<223> OTHER INFORMATION: Hyp
<220> FEATURE:
<221> NAME/KEY: MOD_RES
<222> LOCATION: (27)..(27)
<223> OTHER INFORMATION: Hyp, fPro, mPro or Pro
<220> FEATURE:
<221> NAME/KEY: MOD_RES
<222> LOCATION: (30)..(30)
<223> OTHER INFORMATION: Hyp, fPro, mPro or Pro
<220> FEATURE:
<221> NAME/KEY: MOD_RES
<222> LOCATION: (33)..(33)
<223> OTHER INFORMATION: Hyp, fPro, mPro or Pro
<220> FEATURE:
<221> NAME/KEY: MOD_RES
<222> LOCATION: (36)..(36)
<223> OTHER INFORMATION: Hyp, fPro, mPro or Pro
<220> FEATURE:
<221> NAME/KEY: MOD_RES
<222> LOCATION: (39)..(39)
<223> OTHER INFORMATION: Hyp, fPro, mPro or Pro
<220> FEATURE:
```

-continued

```
<221> NAME/KEY: MOD_RES
<222> LOCATION: (42)..(42)
<223> OTHER INFORMATION: Hyp, fPro, mPro or Pro
<220> FEATURE:
<221> NAME/KEY: MOD_RES
<222> LOCATION: (45)..(45)
<223> OTHER INFORMATION: Hyp, fPro, mPro or Pro
<220> FEATURE:
<221> NAME/KEY: misc_feature
<222> LOCATION: (26)..(46)
<223> OTHER INFORMATION: This region may encompass 0 to 7 "Pro Xaa Gly"
      repeating units
<220> FEATURE:
<221> NAME/KEY: MOD_RES
<222> LOCATION: (47)..(47)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<223> OTHER INFORMATION: see specification as filed for detailed
      description of substitutions and preferred embodiments

<400> SEQUENCE: 5

Xaa Pro Xaa Gly Pro Xaa Gly Pro Xaa Gly Pro Xaa Gly Pro Xaa Gly
1               5                   10                  15

Pro Xaa Gly Pro Xaa Gly Pro Xaa Gly Pro Xaa Gly Pro Xaa Gly Pro
            20                  25                  30

Xaa Gly Pro Xaa Gly Pro Xaa Gly Pro Xaa Gly Pro Xaa Gly Xaa
        35                  40                  45

<210> SEQ ID NO 6
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<221> NAME/KEY: MOD_RES
<222> LOCATION: (3)..(3)
<223> OTHER INFORMATION: Hyp
<220> FEATURE:
<221> NAME/KEY: MOD_RES
<222> LOCATION: (6)..(6)
<223> OTHER INFORMATION: Hyp
<220> FEATURE:
<221> NAME/KEY: MOD_RES
<222> LOCATION: (9)..(9)
<223> OTHER INFORMATION: Hyp
<220> FEATURE:
<221> NAME/KEY: MOD_RES
<222> LOCATION: (12)..(12)
<223> OTHER INFORMATION: Hyp
<220> FEATURE:
<221> NAME/KEY: MOD_RES
<222> LOCATION: (15)..(15)
<223> OTHER INFORMATION: Hyp
<220> FEATURE:
<221> NAME/KEY: MOD_RES
<222> LOCATION: (18)..(18)
<223> OTHER INFORMATION: Hyp
<220> FEATURE:
<221> NAME/KEY: MOD_RES
<222> LOCATION: (21)..(21)
<223> OTHER INFORMATION: Hyp
<220> FEATURE:
<221> NAME/KEY: MOD_RES
<222> LOCATION: (24)..(24)
```

-continued

```
<223> OTHER INFORMATION: Hyp
<220> FEATURE:
<221> NAME/KEY: MOD_RES
<222> LOCATION: (27)..(27)
<223> OTHER INFORMATION: Hyp
<220> FEATURE:
<221> NAME/KEY: MOD_RES
<222> LOCATION: (30)..(30)
<223> OTHER INFORMATION: Hyp
<220> FEATURE:
<221> NAME/KEY: MOD_RES
<222> LOCATION: (33)..(33)
<223> OTHER INFORMATION: Hyp
<220> FEATURE:
<221> NAME/KEY: MOD_RES
<222> LOCATION: (36)..(36)
<223> OTHER INFORMATION: Hyp
<220> FEATURE:
<221> NAME/KEY: MOD_RES
<222> LOCATION: (39)..(39)
<223> OTHER INFORMATION: Hyp, fPro, mPro or Pro
<220> FEATURE:
<221> NAME/KEY: MOD_RES
<222> LOCATION: (42)..(42)
<223> OTHER INFORMATION: Hyp, fPro, mPro or Pro
<220> FEATURE:
<221> NAME/KEY: MOD_RES
<222> LOCATION: (45)..(45)
<223> OTHER INFORMATION: Hyp, fPro, mPro or Pro
<220> FEATURE:
<221> NAME/KEY: misc_feature
<222> LOCATION: (38)..(46)
<223> OTHER INFORMATION: This region may encompass 0 to 3 "Pro Xaa Gly"
      repeating units
<220> FEATURE:
<221> NAME/KEY: MOD_RES
<222> LOCATION: (47)..(47)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<223> OTHER INFORMATION: see specification as filed for detailed
      description of substitutions and preferred embodiments

<400> SEQUENCE: 6

Xaa Pro Xaa Gly Pro Xaa Gly Pro Xaa Gly Pro Xaa Gly Pro Xaa Gly
1               5                   10                  15

Pro Xaa Gly Pro Xaa Gly Pro Xaa Gly Pro Xaa Gly Pro Xaa Gly Pro
            20                  25                  30

Xaa Gly Pro Xaa Gly Pro Xaa Gly Pro Xaa Gly Pro Xaa Gly Xaa
        35                  40                  45

<210> SEQ ID NO 7
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<221> NAME/KEY: MOD_RES
<222> LOCATION: (2)..(2)
<223> OTHER INFORMATION: Hyp
<220> FEATURE:
<221> NAME/KEY: MOD_RES
<222> LOCATION: (5)..(5)
<223> OTHER INFORMATION: Hyp
<220> FEATURE:
```

```
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp, fPro, mPro or Pro
<220> FEATURE:
<221> NAME/KEY: MOD_RES
<222> LOCATION: (17)..(17)
<223> OTHER INFORMATION: Hyp, fPro, mPro or Pro
<220> FEATURE:
<221> NAME/KEY: MOD_RES
<222> LOCATION: (20)..(20)
<223> OTHER INFORMATION: Hyp, fPro, mPro or Pro
<220> FEATURE:
<221> NAME/KEY: MOD_RES
<222> LOCATION: (23)..(23)
<223> OTHER INFORMATION: Hyp, fPro, mPro or Pro
<220> FEATURE:
<221> NAME/KEY: MOD_RES
<222> LOCATION: (26)..(26)
<223> OTHER INFORMATION: Hyp, fPro, mPro or Pro
<220> FEATURE:
<221> NAME/KEY: MOD_RES
<222> LOCATION: (29)..(29)
<223> OTHER INFORMATION: Hyp, fPro, mPro or Pro
<220> FEATURE:
<221> NAME/KEY: MOD_RES
<222> LOCATION: (32)..(32)
<223> OTHER INFORMATION: Hyp, fPro, mPro or Pro
<220> FEATURE:
<221> NAME/KEY: MOD_RES
<222> LOCATION: (35)..(35)
<223> OTHER INFORMATION: Hyp, fPro, mPro or Pro
<220> FEATURE:
<221> NAME/KEY: MOD_RES
<222> LOCATION: (38)..(38)
<223> OTHER INFORMATION: Hyp, fPro, mPro or Pro
<220> FEATURE:
<221> NAME/KEY: MOD_RES
<222> LOCATION: (41)..(41)
<223> OTHER INFORMATION: Hyp, fPro, mPro or Pro
<220> FEATURE:
<221> NAME/KEY: MOD_RES
<222> LOCATION: (44)..(44)
<223> OTHER INFORMATION: Hyp, fPro, mPro or Pro
<220> FEATURE:
<221> NAME/KEY: misc_feature
<222> LOCATION: (14)..(46)
<223> OTHER INFORMATION: This region may encompass 4 to 11 "Xaa Gly Pro"
      repeating units
<220> FEATURE:
<221> NAME/KEY: MOD_RES
<222> LOCATION: (47)..(47)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<223> OTHER INFORMATION: see specification as filed for detailed
      description of substitutions and preferred embodiments

<400> SEQUENCE: 7

Xaa Xaa Gly Pro Xaa Gly Pro Xaa Gly Pro Xaa Gly Pro Xaa Gly Pro
1               5                   10                  15

Xaa Gly Pro Xaa Gly Pro Xaa Gly Pro Xaa Gly Pro Xaa Gly Pro Xaa
            20                  25                  30

Gly Pro Xaa Gly Pro Xaa Gly Pro Xaa Gly Pro Xaa Gly Pro Xaa
        35                  40                  45

<210> SEQ ID NO 8
```

```
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<221> NAME/KEY: MOD_RES
<222> LOCATION: (2)..(2)
<223> OTHER INFORMATION: Hyp
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp
<220> FEATURE:
<221> NAME/KEY: MOD_RES
<222> LOCATION: (23)..(23)
<223> OTHER INFORMATION: Hyp
<220> FEATURE:
<221> NAME/KEY: MOD_RES
<222> LOCATION: (26)..(26)
<223> OTHER INFORMATION: Hyp, fPro, mPro or Pro
<220> FEATURE:
<221> NAME/KEY: MOD_RES
<222> LOCATION: (29)..(29)
<223> OTHER INFORMATION: Hyp, fPro, mPro or Pro
<220> FEATURE:
<221> NAME/KEY: MOD_RES
<222> LOCATION: (32)..(32)
<223> OTHER INFORMATION: Hyp, fPro, mPro or Pro
<220> FEATURE:
<221> NAME/KEY: MOD_RES
<222> LOCATION: (35)..(35)
<223> OTHER INFORMATION: Hyp, fPro, mPro or Pro
<220> FEATURE:
<221> NAME/KEY: MOD_RES
<222> LOCATION: (38)..(38)
<223> OTHER INFORMATION: Hyp, fPro, mPro or Pro
<220> FEATURE:
<221> NAME/KEY: MOD_RES
<222> LOCATION: (41)..(41)
<223> OTHER INFORMATION: Hyp, fPro, mPro or Pro
<220> FEATURE:
<221> NAME/KEY: MOD_RES
<222> LOCATION: (44)..(44)
<223> OTHER INFORMATION: Hyp, fPro, mPro or Pro
<220> FEATURE:
<221> NAME/KEY: misc_feature
<222> LOCATION: (26)..(46)
<223> OTHER INFORMATION: This region may encompass 0 to 7 "Xaa Gly Pro"
      repeating units
<220> FEATURE:
<221> NAME/KEY: MOD_RES
```

```
<222> LOCATION: (47)..(47)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<223> OTHER INFORMATION: see specification as filed for detailed
      description of substitutions and preferred embodiments

<400> SEQUENCE: 8

Xaa Xaa Gly Pro Xaa Gly Pro Xaa Gly Pro Xaa Gly Pro Xaa Gly Pro
1               5                   10                  15

Xaa Gly Pro Xaa Gly Pro Xaa Gly Pro Xaa Gly Pro Xaa Gly Pro Xaa
            20                  25                  30

Gly Pro Xaa Gly Pro Xaa Gly Pro Xaa Gly Pro Xaa Gly Pro Xaa
        35                  40                  45

<210> SEQ ID NO 9
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<221> NAME/KEY: MOD_RES
<222> LOCATION: (2)..(2)
<223> OTHER INFORMATION: Hyp
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp
<220> FEATURE:
<221> NAME/KEY: MOD_RES
<222> LOCATION: (23)..(23)
<223> OTHER INFORMATION: Hyp
<220> FEATURE:
<221> NAME/KEY: MOD_RES
<222> LOCATION: (26)..(26)
<223> OTHER INFORMATION: Hyp
<220> FEATURE:
<221> NAME/KEY: MOD_RES
<222> LOCATION: (29)..(29)
<223> OTHER INFORMATION: Hyp
<220> FEATURE:
<221> NAME/KEY: MOD_RES
<222> LOCATION: (32)..(32)
<223> OTHER INFORMATION: Hyp
<220> FEATURE:
```

```
<221> NAME/KEY: MOD_RES
<222> LOCATION: (35)..(35)
<223> OTHER INFORMATION: Hyp
<220> FEATURE:
<221> NAME/KEY: MOD_RES
<222> LOCATION: (38)..(38)
<223> OTHER INFORMATION: Hyp, fPro, mPro or Pro
<220> FEATURE:
<221> NAME/KEY: MOD_RES
<222> LOCATION: (41)..(41)
<223> OTHER INFORMATION: Hyp, fPro, mPro or Pro
<220> FEATURE:
<221> NAME/KEY: MOD_RES
<222> LOCATION: (44)..(44)
<223> OTHER INFORMATION: Hyp, fPro, mPro or Pro
<220> FEATURE:
<221> NAME/KEY: misc_feature
<222> LOCATION: (38)..(46)
<223> OTHER INFORMATION: This region may encompass 0 to 3 "Xaa Gly Pro"
      repeating units
<220> FEATURE:
<221> NAME/KEY: MOD_RES
<222> LOCATION: (47)..(47)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<223> OTHER INFORMATION: see specification as filed for detailed
      description of substitutions and preferred embodiments

<400> SEQUENCE: 9

Xaa Xaa Gly Pro Xaa Gly Pro Xaa Gly Pro Xaa Gly Pro Xaa Gly Pro
1               5                   10                  15

Xaa Gly Pro Xaa Gly Pro Xaa Gly Pro Xaa Gly Pro Xaa Gly Pro Xaa
            20                  25                  30

Gly Pro Xaa Gly Pro Xaa Gly Pro Xaa Gly Pro Xaa Gly Pro Xaa
        35                  40                  45

<210> SEQ ID NO 10
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<221> NAME/KEY: MOD_RES
<222> LOCATION: (4)..(4)
<223> OTHER INFORMATION: Hyp, fPro, mPro or Pro
<220> FEATURE:
<221> NAME/KEY: MOD_RES
<222> LOCATION: (7)..(7)
<223> OTHER INFORMATION: Hyp, fPro, mPro or Pro
<220> FEATURE:
<221> NAME/KEY: MOD_RES
<222> LOCATION: (10)..(10)
<223> OTHER INFORMATION: Hyp, fPro, mPro or Pro
<220> FEATURE:
<221> NAME/KEY: MOD_RES
<222> LOCATION: (13)..(13)
<223> OTHER INFORMATION: Hyp, fPro, mPro or Pro
<220> FEATURE:
<221> NAME/KEY: MOD_RES
<222> LOCATION: (16)..(16)
<223> OTHER INFORMATION: Hyp, fPro, mPro or Pro
<220> FEATURE:
<221> NAME/KEY: MOD_RES
<222> LOCATION: (19)..(19)
```

```
<223> OTHER INFORMATION: Hyp, fPro, mPro or Pro
<220> FEATURE:
<221> NAME/KEY: MOD_RES
<222> LOCATION: (22)..(22)
<223> OTHER INFORMATION: Hyp, fPro, mPro or Pro
<220> FEATURE:
<221> NAME/KEY: MOD_RES
<222> LOCATION: (25)..(25)
<223> OTHER INFORMATION: Hyp, fPro, mPro or Pro
<220> FEATURE:
<221> NAME/KEY: MOD_RES
<222> LOCATION: (28)..(28)
<223> OTHER INFORMATION: Hyp, fPro, mPro or Pro
<220> FEATURE:
<221> NAME/KEY: MOD_RES
<222> LOCATION: (31)..(31)
<223> OTHER INFORMATION: Hyp, fPro, mPro or Pro
<220> FEATURE:
<221> NAME/KEY: MOD_RES
<222> LOCATION: (34)..(34)
<223> OTHER INFORMATION: Hyp, fPro, mPro or Pro
<220> FEATURE:
<221> NAME/KEY: misc_feature
<222> LOCATION: (2)..(34)
<223> OTHER INFORMATION: This region may encompass 4 to 11 "Gly Pro Xaa"
      repeating units
<220> FEATURE:
<221> NAME/KEY: MOD_RES
<222> LOCATION: (37)..(37)
<223> OTHER INFORMATION: Hyp
<220> FEATURE:
<221> NAME/KEY: MOD_RES
<222> LOCATION: (40)..(40)
<223> OTHER INFORMATION: Hyp
<220> FEATURE:
<221> NAME/KEY: MOD_RES
<222> LOCATION: (43)..(43)
<223> OTHER INFORMATION: Hyp
<220> FEATURE:
<221> NAME/KEY: MOD_RES
<222> LOCATION: (46)..(46)
<223> OTHER INFORMATION: Hyp
<220> FEATURE:
<221> NAME/KEY: MOD_RES
<222> LOCATION: (47)..(47)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<223> OTHER INFORMATION: see specification as filed for detailed
      description of substitutions and preferred embodiments

<400> SEQUENCE: 10

Xaa Gly Pro Xaa Gly Pro Xaa Gly Pro Xaa Gly Pro Xaa Gly Pro Xaa
1               5                   10                  15

Gly Pro Xaa Gly Pro Xaa Gly Pro Xaa Gly Pro Xaa Gly Pro Xaa Gly
            20                  25                  30

Pro Xaa Gly Pro Xaa Gly Pro Xaa Gly Pro Xaa Gly Pro Xaa Xaa
        35                  40                  45

<210> SEQ ID NO 11
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
```

```
<221> NAME/KEY: MOD_RES
<222> LOCATION: (4)..(4)
<223> OTHER INFORMATION: Hyp, fPro, mPro or Pro
<220> FEATURE:
<221> NAME/KEY: MOD_RES
<222> LOCATION: (7)..(7)
<223> OTHER INFORMATION: Hyp, fPro, mPro or Pro
<220> FEATURE:
<221> NAME/KEY: MOD_RES
<222> LOCATION: (10)..(10)
<223> OTHER INFORMATION: Hyp, fPro, mPro or Pro
<220> FEATURE:
<221> NAME/KEY: MOD_RES
<222> LOCATION: (13)..(13)
<223> OTHER INFORMATION: Hyp, fPro, mPro or Pro
<220> FEATURE:
<221> NAME/KEY: MOD_RES
<222> LOCATION: (16)..(16)
<223> OTHER INFORMATION: Hyp, fPro, mPro or Pro
<220> FEATURE:
<221> NAME/KEY: MOD_RES
<222> LOCATION: (19)..(19)
<223> OTHER INFORMATION: Hyp, fPro, mPro or Pro
<220> FEATURE:
<221> NAME/KEY: MOD_RES
<222> LOCATION: (22)..(22)
<223> OTHER INFORMATION: Hyp, fPro, mPro or Pro
<220> FEATURE:
<221> NAME/KEY: misc_feature
<222> LOCATION: (2)..(22)
<223> OTHER INFORMATION: This region may encompass 0 to 7 "Gly Pro Xaa"
      repeating units
<220> FEATURE:
<221> NAME/KEY: MOD_RES
<222> LOCATION: (25)..(25)
<223> OTHER INFORMATION: Hyp
<220> FEATURE:
<221> NAME/KEY: MOD_RES
<222> LOCATION: (28)..(28)
<223> OTHER INFORMATION: Hyp
<220> FEATURE:
<221> NAME/KEY: MOD_RES
<222> LOCATION: (31)..(31)
<223> OTHER INFORMATION: Hyp
<220> FEATURE:
<221> NAME/KEY: MOD_RES
<222> LOCATION: (34)..(34)
<223> OTHER INFORMATION: Hyp
<220> FEATURE:
<221> NAME/KEY: MOD_RES
<222> LOCATION: (37)..(37)
<223> OTHER INFORMATION: Hyp
<220> FEATURE:
<221> NAME/KEY: MOD_RES
<222> LOCATION: (40)..(40)
<223> OTHER INFORMATION: Hyp
<220> FEATURE:
<221> NAME/KEY: MOD_RES
<222> LOCATION: (43)..(43)
<223> OTHER INFORMATION: Hyp
<220> FEATURE:
<221> NAME/KEY: MOD_RES
<222> LOCATION: (46)..(46)
<223> OTHER INFORMATION: Hyp
<220> FEATURE:
<221> NAME/KEY: MOD_RES
<222> LOCATION: (47)..(47)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<223> OTHER INFORMATION: see specification as filed for detailed
      description of substitutions and preferred embodiments

<400> SEQUENCE: 11

Xaa Gly Pro Xaa Gly Pro Xaa Gly Pro Xaa Gly Pro Xaa Gly Pro Xaa
1               5                   10                  15
```

```
Gly Pro Xaa Gly Pro Xaa Gly Pro Xaa Gly Pro Xaa Gly
            20                  25                  30

Pro Xaa Gly Pro Xaa Gly Pro Xaa Gly Pro Xaa Xaa
        35                  40                  45

<210> SEQ ID NO 12
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<221> NAME/KEY: MOD_RES
<222> LOCATION: (4)..(4)
<223> OTHER INFORMATION: Hyp, fPro, mPro or Pro
<220> FEATURE:
<221> NAME/KEY: MOD_RES
<222> LOCATION: (7)..(7)
<223> OTHER INFORMATION: Hyp, fPro, mPro or Pro
<220> FEATURE:
<221> NAME/KEY: MOD_RES
<222> LOCATION: (10)..(10)
<223> OTHER INFORMATION: Hyp, fPro, mPro or Pro
<220> FEATURE:
<221> NAME/KEY: misc_feature
<222> LOCATION: (2)..(10)
<223> OTHER INFORMATION: This region may encompass 0 to 3 "Gly Pro Xaa"
      repeating units
<220> FEATURE:
<221> NAME/KEY: MOD_RES
<222> LOCATION: (13)..(13)
<223> OTHER INFORMATION: Hyp
<220> FEATURE:
<221> NAME/KEY: MOD_RES
<222> LOCATION: (16)..(16)
<223> OTHER INFORMATION: Hyp
<220> FEATURE:
<221> NAME/KEY: MOD_RES
<222> LOCATION: (19)..(19)
<223> OTHER INFORMATION: Hyp
<220> FEATURE:
<221> NAME/KEY: MOD_RES
<222> LOCATION: (22)..(22)
<223> OTHER INFORMATION: Hyp
<220> FEATURE:
<221> NAME/KEY: MOD_RES
<222> LOCATION: (25)..(25)
<223> OTHER INFORMATION: Hyp
<220> FEATURE:
<221> NAME/KEY: MOD_RES
<222> LOCATION: (28)..(28)
<223> OTHER INFORMATION: Hyp
<220> FEATURE:
<221> NAME/KEY: MOD_RES
<222> LOCATION: (31)..(31)
<223> OTHER INFORMATION: Hyp
<220> FEATURE:
<221> NAME/KEY: MOD_RES
<222> LOCATION: (34)..(34)
<223> OTHER INFORMATION: Hyp
<220> FEATURE:
<221> NAME/KEY: MOD_RES
<222> LOCATION: (37)..(37)
<223> OTHER INFORMATION: Hyp
<220> FEATURE:
<221> NAME/KEY: MOD_RES
<222> LOCATION: (40)..(40)
<223> OTHER INFORMATION: Hyp
<220> FEATURE:
<221> NAME/KEY: MOD_RES
```

```
<222> LOCATION: (43)..(43)
<223> OTHER INFORMATION: Hyp
<220> FEATURE:
<221> NAME/KEY: MOD_RES
<222> LOCATION: (46)..(46)
<223> OTHER INFORMATION: Hyp
<220> FEATURE:
<221> NAME/KEY: MOD_RES
<222> LOCATION: (47)..(47)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<223> OTHER INFORMATION: see specification as filed for detailed
      description of substitutions and preferred embodiments

<400> SEQUENCE: 12

Xaa Gly Pro Xaa Gly Pro Xaa Gly Pro Xaa Gly Pro Xaa Gly Pro Xaa
1               5                   10                  15

Gly Pro Xaa Gly Pro Xaa Gly Pro Xaa Gly Pro Xaa Gly Pro Xaa Gly
            20                  25                  30

Pro Xaa Gly Pro Xaa Gly Pro Xaa Gly Pro Xaa Gly Pro Xaa Xaa
        35                  40                  45

<210> SEQ ID NO 13
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<221> NAME/KEY: MOD_RES
<222> LOCATION: (3)..(3)
<223> OTHER INFORMATION: Hyp, fPro, mPro or Pro
<220> FEATURE:
<221> NAME/KEY: MOD_RES
<222> LOCATION: (6)..(6)
<223> OTHER INFORMATION: Hyp, fPro, mPro or Pro
<220> FEATURE:
<221> NAME/KEY: MOD_RES
<222> LOCATION: (9)..(9)
<223> OTHER INFORMATION: Hyp, fPro, mPro or Pro
<220> FEATURE:
<221> NAME/KEY: MOD_RES
<222> LOCATION: (12)..(12)
<223> OTHER INFORMATION: Hyp, fPro, mPro or Pro
<220> FEATURE:
<221> NAME/KEY: MOD_RES
<222> LOCATION: (15)..(15)
<223> OTHER INFORMATION: Hyp, fPro, mPro or Pro
<220> FEATURE:
<221> NAME/KEY: MOD_RES
<222> LOCATION: (18)..(18)
<223> OTHER INFORMATION: Hyp, fPro, mPro or Pro
<220> FEATURE:
<221> NAME/KEY: MOD_RES
<222> LOCATION: (21)..(21)
<223> OTHER INFORMATION: Hyp, fPro, mPro or Pro
<220> FEATURE:
<221> NAME/KEY: MOD_RES
<222> LOCATION: (24)..(24)
<223> OTHER INFORMATION: Hyp, fPro, mPro or Pro
<220> FEATURE:
<221> NAME/KEY: MOD_RES
<222> LOCATION: (27)..(27)
<223> OTHER INFORMATION: Hyp, fPro, mPro or Pro
<220> FEATURE:
```

```
<221> NAME/KEY: MOD_RES
<222> LOCATION: (30)..(30)
<223> OTHER INFORMATION: Hyp, fPro, mPro or Pro
<220> FEATURE:
<221> NAME/KEY: MOD_RES
<222> LOCATION: (33)..(33)
<223> OTHER INFORMATION: Hyp, fPro, mPro or Pro
<220> FEATURE:
<221> NAME/KEY: misc_feature
<222> LOCATION: (2)..(34)
<223> OTHER INFORMATION: This region may encompass 4 to 11 "Pro Xaa Gly"
      repeating units
<220> FEATURE:
<221> NAME/KEY: MOD_RES
<222> LOCATION: (36)..(36)
<223> OTHER INFORMATION: Hyp
<220> FEATURE:
<221> NAME/KEY: MOD_RES
<222> LOCATION: (39)..(39)
<223> OTHER INFORMATION: Hyp
<220> FEATURE:
<221> NAME/KEY: MOD_RES
<222> LOCATION: (42)..(42)
<223> OTHER INFORMATION: Hyp
<220> FEATURE:
<221> NAME/KEY: MOD_RES
<222> LOCATION: (45)..(45)
<223> OTHER INFORMATION: Hyp
<220> FEATURE:
<221> NAME/KEY: MOD_RES
<222> LOCATION: (47)..(47)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<223> OTHER INFORMATION: see specification as filed for detailed
      description of substitutions and preferred embodiments

<400> SEQUENCE: 13

Xaa Pro Xaa Gly Pro Xaa Gly Pro Xaa Gly Pro Xaa Gly Pro Xaa Gly
1               5                   10                  15

Pro Xaa Gly Pro Xaa Gly Pro Xaa Gly Pro Xaa Gly Pro Xaa Gly Pro
            20                  25                  30

Xaa Gly Pro Xaa Gly Pro Xaa Gly Pro Xaa Gly Pro Xaa Gly Xaa
        35                  40                  45

<210> SEQ ID NO 14
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<221> NAME/KEY: MOD_RES
<222> LOCATION: (3)..(3)
<223> OTHER INFORMATION: Hyp, fPro, mPro or Pro
<220> FEATURE:
<221> NAME/KEY: MOD_RES
<222> LOCATION: (6)..(6)
<223> OTHER INFORMATION: Hyp, fPro, mPro or Pro
<220> FEATURE:
<221> NAME/KEY: MOD_RES
<222> LOCATION: (9)..(9)
<223> OTHER INFORMATION: Hyp, fPro, mPro or Pro
<220> FEATURE:
<221> NAME/KEY: MOD_RES
<222> LOCATION: (12)..(12)
```

```
<223> OTHER INFORMATION: Hyp, fPro, mPro or Pro
<220> FEATURE:
<221> NAME/KEY: MOD_RES
<222> LOCATION: (15)..(15)
<223> OTHER INFORMATION: Hyp, fPro, mPro or Pro
<220> FEATURE:
<221> NAME/KEY: MOD_RES
<222> LOCATION: (18)..(18)
<223> OTHER INFORMATION: Hyp, fPro, mPro or Pro
<220> FEATURE:
<221> NAME/KEY: MOD_RES
<222> LOCATION: (21)..(21)
<223> OTHER INFORMATION: Hyp, fPro, mPro or Pro
<220> FEATURE:
<221> NAME/KEY: misc_feature
<222> LOCATION: (2)..(22)
<223> OTHER INFORMATION: This region may encompass 0 to 7 "Pro Xaa Gly"
      repeating units
<220> FEATURE:
<221> NAME/KEY: MOD_RES
<222> LOCATION: (24)..(24)
<223> OTHER INFORMATION: Hyp
<220> FEATURE:
<221> NAME/KEY: MOD_RES
<222> LOCATION: (27)..(27)
<223> OTHER INFORMATION: Hyp
<220> FEATURE:
<221> NAME/KEY: MOD_RES
<222> LOCATION: (30)..(30)
<223> OTHER INFORMATION: Hyp
<220> FEATURE:
<221> NAME/KEY: MOD_RES
<222> LOCATION: (33)..(33)
<223> OTHER INFORMATION: Hyp
<220> FEATURE:
<221> NAME/KEY: MOD_RES
<222> LOCATION: (36)..(36)
<223> OTHER INFORMATION: Hyp
<220> FEATURE:
<221> NAME/KEY: MOD_RES
<222> LOCATION: (39)..(39)
<223> OTHER INFORMATION: Hyp
<220> FEATURE:
<221> NAME/KEY: MOD_RES
<222> LOCATION: (42)..(42)
<223> OTHER INFORMATION: Hyp
<220> FEATURE:
<221> NAME/KEY: MOD_RES
<222> LOCATION: (45)..(45)
<223> OTHER INFORMATION: Hyp
<220> FEATURE:
<221> NAME/KEY: MOD_RES
<222> LOCATION: (47)..(47)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<223> OTHER INFORMATION: see specification as filed for detailed
      description of substitutions and preferred embodiments

<400> SEQUENCE: 14

Xaa Pro Xaa Gly Pro Xaa Gly Pro Xaa Gly Pro Xaa Gly Pro Xaa Gly
1               5                   10                  15

Pro Xaa Gly Pro Xaa Gly Pro Xaa Gly Pro Xaa Gly Pro Xaa Gly Pro
            20                  25                  30

Xaa Gly Pro Xaa Gly Pro Xaa Gly Pro Xaa Gly Pro Xaa Gly Xaa
        35                  40                  45

<210> SEQ ID NO 15
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (1)..(1)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<221> NAME/KEY: MOD_RES
<222> LOCATION: (3)..(3)
<223> OTHER INFORMATION: Hyp, fPro, mPro or Pro
<220> FEATURE:
<221> NAME/KEY: MOD_RES
<222> LOCATION: (6)..(6)
<223> OTHER INFORMATION: Hyp, fPro, mPro or Pro
<220> FEATURE:
<221> NAME/KEY: MOD_RES
<222> LOCATION: (9)..(9)
<223> OTHER INFORMATION: Hyp, fPro, mPro or Pro
<220> FEATURE:
<221> NAME/KEY: misc_feature
<222> LOCATION: (2)..(10)
<223> OTHER INFORMATION: This region may encompass 0 to 3 "Pro Xaa Gly"
      repeating units
<220> FEATURE:
<221> NAME/KEY: MOD_RES
<222> LOCATION: (12)..(12)
<223> OTHER INFORMATION: Hyp
<220> FEATURE:
<221> NAME/KEY: MOD_RES
<222> LOCATION: (15)..(15)
<223> OTHER INFORMATION: Hyp
<220> FEATURE:
<221> NAME/KEY: MOD_RES
<222> LOCATION: (18)..(18)
<223> OTHER INFORMATION: Hyp
<220> FEATURE:
<221> NAME/KEY: MOD_RES
<222> LOCATION: (21)..(21)
<223> OTHER INFORMATION: Hyp
<220> FEATURE:
<221> NAME/KEY: MOD_RES
<222> LOCATION: (24)..(24)
<223> OTHER INFORMATION: Hyp
<220> FEATURE:
<221> NAME/KEY: MOD_RES
<222> LOCATION: (27)..(27)
<223> OTHER INFORMATION: Hyp
<220> FEATURE:
<221> NAME/KEY: MOD_RES
<222> LOCATION: (30)..(30)
<223> OTHER INFORMATION: Hyp
<220> FEATURE:
<221> NAME/KEY: MOD_RES
<222> LOCATION: (33)..(33)
<223> OTHER INFORMATION: Hyp
<220> FEATURE:
<221> NAME/KEY: MOD_RES
<222> LOCATION: (36)..(36)
<223> OTHER INFORMATION: Hyp
<220> FEATURE:
<221> NAME/KEY: MOD_RES
<222> LOCATION: (39)..(39)
<223> OTHER INFORMATION: Hyp
<220> FEATURE:
<221> NAME/KEY: MOD_RES
<222> LOCATION: (42)..(42)
<223> OTHER INFORMATION: Hyp
<220> FEATURE:
<221> NAME/KEY: MOD_RES
<222> LOCATION: (45)..(45)
<223> OTHER INFORMATION: Hyp
<220> FEATURE:
<221> NAME/KEY: MOD_RES
<222> LOCATION: (47)..(47)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
```

<223> OTHER INFORMATION: see specification as filed for detailed
      description of substitutions and preferred embodiments

<400> SEQUENCE: 15

Xaa Pro Xaa Gly Pro Xaa Gly Pro Xaa Gly Pro Xaa Gly Pro Xaa Gly
1               5                   10                  15

Pro Xaa Gly Pro Xaa Gly Pro Xaa Gly Pro Xaa Gly Pro Xaa Gly Pro
            20                  25                  30

Xaa Gly Pro Xaa Gly Pro Xaa Gly Pro Xaa Gly Pro Xaa Gly Xaa
        35                  40                  45

<210> SEQ ID NO 16
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<221> NAME/KEY: MOD_RES
<222> LOCATION: (2)..(2)
<223> OTHER INFORMATION: Hyp, fPro, mPro or Pro
<220> FEATURE:
<221> NAME/KEY: MOD_RES
<222> LOCATION: (5)..(5)
<223> OTHER INFORMATION: Hyp, fPro, mPro or Pro
<220> FEATURE:
<221> NAME/KEY: MOD_RES
<222> LOCATION: (8)..(8)
<223> OTHER INFORMATION: Hyp, fPro, mPro or Pro
<220> FEATURE:
<221> NAME/KEY: MOD_RES
<222> LOCATION: (11)..(11)
<223> OTHER INFORMATION: Hyp, fPro, mPro or Pro
<220> FEATURE:
<221> NAME/KEY: MOD_RES
<222> LOCATION: (14)..(14)
<223> OTHER INFORMATION: Hyp, fPro, mPro or Pro
<220> FEATURE:
<221> NAME/KEY: MOD_RES
<222> LOCATION: (17)..(17)
<223> OTHER INFORMATION: Hyp, fPro, mPro or Pro
<220> FEATURE:
<221> NAME/KEY: MOD_RES
<222> LOCATION: (20)..(20)
<223> OTHER INFORMATION: Hyp, fPro, mPro or Pro
<220> FEATURE:
<221> NAME/KEY: MOD_RES
<222> LOCATION: (23)..(23)
<223> OTHER INFORMATION: Hyp, fPro, mPro or Pro
<220> FEATURE:
<221> NAME/KEY: MOD_RES
<222> LOCATION: (26)..(26)
<223> OTHER INFORMATION: Hyp, fPro, mPro or Pro
<220> FEATURE:
<221> NAME/KEY: MOD_RES
<222> LOCATION: (29)..(29)
<223> OTHER INFORMATION: Hyp, fPro, mPro or Pro
<220> FEATURE:
<221> NAME/KEY: MOD_RES
<222> LOCATION: (32)..(32)
<223> OTHER INFORMATION: Hyp, fPro, mPro or Pro
<220> FEATURE:
<221> NAME/KEY: misc_feature
<222> LOCATION: (2)..(34)
<223> OTHER INFORMATION: This region may encompass 4 to 11 "Xaa Gly Pro"
      repeating units
<220> FEATURE:
<221> NAME/KEY: MOD_RES

```
<222> LOCATION: (35)..(35)
<223> OTHER INFORMATION: Hyp
<220> FEATURE:
<221> NAME/KEY: MOD_RES
<222> LOCATION: (38)..(38)
<223> OTHER INFORMATION: Hyp
<220> FEATURE:
<221> NAME/KEY: MOD_RES
<222> LOCATION: (41)..(41)
<223> OTHER INFORMATION: Hyp
<220> FEATURE:
<221> NAME/KEY: MOD_RES
<222> LOCATION: (44)..(44)
<223> OTHER INFORMATION: Hyp
<220> FEATURE:
<221> NAME/KEY: MOD_RES
<222> LOCATION: (47)..(47)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<223> OTHER INFORMATION: see specification as filed for detailed
      description of substitutions and preferred embodiments

<400> SEQUENCE: 16

Xaa Xaa Gly Pro Xaa Gly Pro Xaa Gly Pro Xaa Gly Pro Xaa Gly Pro
1               5                   10                  15

Xaa Gly Pro Xaa Gly Pro Xaa Gly Pro Xaa Gly Pro Xaa Gly Pro Xaa
            20                  25                  30

Gly Pro Xaa Gly Pro Xaa Gly Pro Xaa Gly Pro Xaa Gly Pro Xaa
        35                  40                  45

<210> SEQ ID NO 17
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<221> NAME/KEY: MOD_RES
<222> LOCATION: (2)..(2)
<223> OTHER INFORMATION: Hyp, fPro, mPro or Pro
<220> FEATURE:
<221> NAME/KEY: MOD_RES
<222> LOCATION: (5)..(5)
<223> OTHER INFORMATION: Hyp, fPro, mPro or Pro
<220> FEATURE:
<221> NAME/KEY: MOD_RES
<222> LOCATION: (8)..(8)
<223> OTHER INFORMATION: Hyp, fPro, mPro or Pro
<220> FEATURE:
<221> NAME/KEY: MOD_RES
<222> LOCATION: (11)..(11)
<223> OTHER INFORMATION: Hyp, fPro, mPro or Pro
<220> FEATURE:
<221> NAME/KEY: MOD_RES
<222> LOCATION: (14)..(14)
<223> OTHER INFORMATION: Hyp, fPro, mPro or Pro
<220> FEATURE:
<221> NAME/KEY: MOD_RES
<222> LOCATION: (17)..(17)
<223> OTHER INFORMATION: Hyp, fPro, mPro or Pro
<220> FEATURE:
<221> NAME/KEY: MOD_RES
<222> LOCATION: (20)..(20)
<223> OTHER INFORMATION: Hyp, fPro, mPro or Pro
<220> FEATURE:
```

```
<221> NAME/KEY: misc_feature
<222> LOCATION: (2)..(22)
<223> OTHER INFORMATION: This region may encompass 0 to 7 "Xaa Gly Pro"
      repeating units
<220> FEATURE:
<221> NAME/KEY: MOD_RES
<222> LOCATION: (23)..(23)
<223> OTHER INFORMATION: Hyp
<220> FEATURE:
<221> NAME/KEY: MOD_RES
<222> LOCATION: (26)..(26)
<223> OTHER INFORMATION: Hyp
<220> FEATURE:
<221> NAME/KEY: MOD_RES
<222> LOCATION: (29)..(29)
<223> OTHER INFORMATION: Hyp
<220> FEATURE:
<221> NAME/KEY: MOD_RES
<222> LOCATION: (32)..(32)
<223> OTHER INFORMATION: Hyp
<220> FEATURE:
<221> NAME/KEY: MOD_RES
<222> LOCATION: (35)..(35)
<223> OTHER INFORMATION: Hyp
<220> FEATURE:
<221> NAME/KEY: MOD_RES
<222> LOCATION: (38)..(38)
<223> OTHER INFORMATION: Hyp
<220> FEATURE:
<221> NAME/KEY: MOD_RES
<222> LOCATION: (41)..(41)
<223> OTHER INFORMATION: Hyp
<220> FEATURE:
<221> NAME/KEY: MOD_RES
<222> LOCATION: (44)..(44)
<223> OTHER INFORMATION: Hyp
<220> FEATURE:
<221> NAME/KEY: MOD_RES
<222> LOCATION: (47)..(47)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<223> OTHER INFORMATION: see specification as filed for detailed
      description of substitutions and preferred embodiments

<400> SEQUENCE: 17

Xaa Xaa Gly Pro Xaa Gly Pro Xaa Gly Pro Xaa Gly Pro Xaa Gly Pro
1               5                   10                  15

Xaa Gly Pro Xaa Gly Pro Xaa Gly Pro Xaa Gly Pro Xaa Gly Pro Xaa
            20                  25                  30

Gly Pro Xaa Gly Pro Xaa Gly Pro Xaa Gly Pro Xaa Gly Pro Xaa
        35                  40                  45

<210> SEQ ID NO 18
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<221> NAME/KEY: MOD_RES
<222> LOCATION: (2)..(2)
<223> OTHER INFORMATION: Hyp, fPro, mPro or Pro
<220> FEATURE:
<221> NAME/KEY: MOD_RES
<222> LOCATION: (5)..(5)
```

```
<223> OTHER INFORMATION: Hyp, fPro, mPro or Pro
<220> FEATURE:
<221> NAME/KEY: MOD_RES
<222> LOCATION: (8)..(8)
<223> OTHER INFORMATION: Hyp, fPro, mPro or Pro
<220> FEATURE:
<221> NAME/KEY: misc_feature
<222> LOCATION: (2)..(10)
<223> OTHER INFORMATION: This region may encompass 0 to 3 "Xaa Gly Pro"
      repeating units
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp
<220> FEATURE:
<221> NAME/KEY: MOD_RES
<222> LOCATION: (23)..(23)
<223> OTHER INFORMATION: Hyp
<220> FEATURE:
<221> NAME/KEY: MOD_RES
<222> LOCATION: (26)..(26)
<223> OTHER INFORMATION: Hyp
<220> FEATURE:
<221> NAME/KEY: MOD_RES
<222> LOCATION: (29)..(29)
<223> OTHER INFORMATION: Hyp
<220> FEATURE:
<221> NAME/KEY: MOD_RES
<222> LOCATION: (32)..(32)
<223> OTHER INFORMATION: Hyp
<220> FEATURE:
<221> NAME/KEY: MOD_RES
<222> LOCATION: (35)..(35)
<223> OTHER INFORMATION: Hyp
<220> FEATURE:
<221> NAME/KEY: MOD_RES
<222> LOCATION: (38)..(38)
<223> OTHER INFORMATION: Hyp
<220> FEATURE:
<221> NAME/KEY: MOD_RES
<222> LOCATION: (41)..(41)
<223> OTHER INFORMATION: Hyp
<220> FEATURE:
<221> NAME/KEY: MOD_RES
<222> LOCATION: (44)..(44)
<223> OTHER INFORMATION: Hyp
<220> FEATURE:
<221> NAME/KEY: MOD_RES
<222> LOCATION: (47)..(47)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<223> OTHER INFORMATION: see specification as filed for detailed
      description of substitutions and preferred embodiments

<400> SEQUENCE: 18

Xaa Xaa Gly Pro Xaa Gly Pro Xaa Gly Pro Xaa Gly Pro Xaa Gly Pro
1               5                   10                  15

Xaa Gly Pro Xaa Gly Pro Xaa Gly Pro Xaa Gly Pro Xaa Gly Pro Xaa
            20                  25                  30

Gly Pro Xaa Gly Pro Xaa Gly Pro Xaa Gly Pro Xaa Gly Pro Xaa
        35                  40                  45
```

```
<210> SEQ ID NO 19
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<221> NAME/KEY: MOD_RES
<222> LOCATION: (4)..(4)
<223> OTHER INFORMATION: Hyp, fPro, mPro or Pro
<220> FEATURE:
<221> NAME/KEY: MOD_RES
<222> LOCATION: (7)..(7)
<223> OTHER INFORMATION: Hyp, fPro, mPro or Pro
<220> FEATURE:
<221> NAME/KEY: MOD_RES
<222> LOCATION: (10)..(10)
<223> OTHER INFORMATION: Hyp, fPro, mPro or Pro
<220> FEATURE:
<221> NAME/KEY: MOD_RES
<222> LOCATION: (13)..(13)
<223> OTHER INFORMATION: Hyp, fPro, mPro or Pro
<220> FEATURE:
<221> NAME/KEY: MOD_RES
<222> LOCATION: (16)..(16)
<223> OTHER INFORMATION: Hyp, fPro, mPro or Pro
<220> FEATURE:
<221> NAME/KEY: MOD_RES
<222> LOCATION: (19)..(19)
<223> OTHER INFORMATION: Hyp, fPro, mPro or Pro
<220> FEATURE:
<221> NAME/KEY: MOD_RES
<222> LOCATION: (22)..(22)
<223> OTHER INFORMATION: Hyp, fPro, mPro or Pro
<220> FEATURE:
<221> NAME/KEY: MOD_RES
<222> LOCATION: (25)..(25)
<223> OTHER INFORMATION: Hyp, fPro, mPro or Pro
<220> FEATURE:
<221> NAME/KEY: MOD_RES
<222> LOCATION: (28)..(28)
<223> OTHER INFORMATION: Hyp, fPro, mPro or Pro
<220> FEATURE:
<221> NAME/KEY: MOD_RES
<222> LOCATION: (31)..(31)
<223> OTHER INFORMATION: Hyp, fPro, mPro or Pro
<220> FEATURE:
<221> NAME/KEY: misc_feature
<222> LOCATION: (2)..(31)
<223> OTHER INFORMATION: This region may encompass 1 to 10 "Gly Pro Xaa"
      repeating units
<220> FEATURE:
<221> NAME/KEY: MOD_RES
<222> LOCATION: (34)..(34)
<223> OTHER INFORMATION: Hyp
<220> FEATURE:
<221> NAME/KEY: MOD_RES
<222> LOCATION: (37)..(37)
<223> OTHER INFORMATION: Hyp
<220> FEATURE:
<221> NAME/KEY: MOD_RES
<222> LOCATION: (40)..(40)
<223> OTHER INFORMATION: Hyp
<220> FEATURE:
<221> NAME/KEY: MOD_RES
<222> LOCATION: (43)..(43)
<223> OTHER INFORMATION: Hyp
<220> FEATURE:
<221> NAME/KEY: MOD_RES
<222> LOCATION: (46)..(46)
<223> OTHER INFORMATION: Hyp, fPro, mPro or Pro
```

```
<220> FEATURE:
<221> NAME/KEY: MOD_RES
<222> LOCATION: (49)..(49)
<223> OTHER INFORMATION: Hyp, fPro, mPro or Pro
<220> FEATURE:
<221> NAME/KEY: MOD_RES
<222> LOCATION: (52)..(52)
<223> OTHER INFORMATION: Hyp, fPro, mPro or Pro
<220> FEATURE:
<221> NAME/KEY: MOD_RES
<222> LOCATION: (55)..(55)
<223> OTHER INFORMATION: Hyp, fPro, mPro or Pro
<220> FEATURE:
<221> NAME/KEY: MOD_RES
<222> LOCATION: (58)..(58)
<223> OTHER INFORMATION: Hyp, fPro, mPro or Pro
<220> FEATURE:
<221> NAME/KEY: MOD_RES
<222> LOCATION: (61)..(61)
<223> OTHER INFORMATION: Hyp, fPro, mPro or Pro
<220> FEATURE:
<221> NAME/KEY: MOD_RES
<222> LOCATION: (64)..(64)
<223> OTHER INFORMATION: Hyp, fPro, mPro or Pro
<220> FEATURE:
<221> NAME/KEY: MOD_RES
<222> LOCATION: (67)..(67)
<223> OTHER INFORMATION: Hyp, fPro, mPro or Pro
<220> FEATURE:
<221> NAME/KEY: MOD_RES
<222> LOCATION: (70)..(70)
<223> OTHER INFORMATION: Hyp, fPro, mPro or Pro
<220> FEATURE:
<221> NAME/KEY: MOD_RES
<222> LOCATION: (73)..(73)
<223> OTHER INFORMATION: Hyp, fPro, mPro or Pro
<220> FEATURE:
<221> NAME/KEY: misc_feature
<222> LOCATION: (44)..(73)
<223> OTHER INFORMATION: This region may encompass 1 to 10 "Gly Pro Xaa"
      repeating units
<220> FEATURE:
<221> NAME/KEY: MOD_RES
<222> LOCATION: (74)..(74)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<223> OTHER INFORMATION: see specification as filed for detailed
      description of substitutions and preferred embodiments

<400> SEQUENCE: 19

Xaa Gly Pro Xaa Gly Pro Xaa Gly Pro Xaa Gly Pro Xaa Gly Pro Xaa
1               5                   10                  15

Gly Pro Xaa Gly Pro Xaa Gly Pro Xaa Gly Pro Xaa Gly Pro Xaa Gly
            20                  25                  30

Pro Xaa Gly Pro Xaa Gly Pro Xaa Gly Pro Xaa Gly Pro Xaa Gly Pro
        35                  40                  45

Xaa Gly Pro Xaa Gly Pro Xaa Gly Pro Xaa Gly Pro Xaa Gly Pro Xaa
    50                  55                  60

Gly Pro Xaa Gly Pro Xaa Gly Pro Xaa Xaa
65                  70

<210> SEQ ID NO 20
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
```

```
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<221> NAME/KEY: MOD_RES
<222> LOCATION: (4)..(4)
<223> OTHER INFORMATION: Hyp, fPro, mPro or Pro
<220> FEATURE:
<221> NAME/KEY: MOD_RES
<222> LOCATION: (7)..(7)
<223> OTHER INFORMATION: Hyp, fPro, mPro or Pro
<220> FEATURE:
<221> NAME/KEY: MOD_RES
<222> LOCATION: (10)..(10)
<223> OTHER INFORMATION: Hyp, fPro, mPro or Pro
<220> FEATURE:
<221> NAME/KEY: MOD_RES
<222> LOCATION: (13)..(13)
<223> OTHER INFORMATION: Hyp, fPro, mPro or Pro
<220> FEATURE:
<221> NAME/KEY: MOD_RES
<222> LOCATION: (16)..(16)
<223> OTHER INFORMATION: Hyp, fPro, mPro or Pro
<220> FEATURE:
<221> NAME/KEY: MOD_RES
<222> LOCATION: (19)..(19)
<223> OTHER INFORMATION: Hyp, fPro, mPro or Pro
<220> FEATURE:
<221> NAME/KEY: misc_feature
<222> LOCATION: (2)..(19)
<223> OTHER INFORMATION: This region may encompass 1 to 6 "Gly Pro Xaa"
      repeating units
<220> FEATURE:
<221> NAME/KEY: MOD_RES
<222> LOCATION: (22)..(22)
<223> OTHER INFORMATION: Hyp
<220> FEATURE:
<221> NAME/KEY: MOD_RES
<222> LOCATION: (25)..(25)
<223> OTHER INFORMATION: Hyp
<220> FEATURE:
<221> NAME/KEY: MOD_RES
<222> LOCATION: (28)..(28)
<223> OTHER INFORMATION: Hyp
<220> FEATURE:
<221> NAME/KEY: MOD_RES
<222> LOCATION: (31)..(31)
<223> OTHER INFORMATION: Hyp
<220> FEATURE:
<221> NAME/KEY: MOD_RES
<222> LOCATION: (34)..(34)
<223> OTHER INFORMATION: Hyp
<220> FEATURE:
<221> NAME/KEY: MOD_RES
<222> LOCATION: (37)..(37)
<223> OTHER INFORMATION: Hyp
<220> FEATURE:
<221> NAME/KEY: MOD_RES
<222> LOCATION: (40)..(40)
<223> OTHER INFORMATION: Hyp
<220> FEATURE:
<221> NAME/KEY: MOD_RES
<222> LOCATION: (43)..(43)
<223> OTHER INFORMATION: Hyp
<220> FEATURE:
<221> NAME/KEY: MOD_RES
<222> LOCATION: (46)..(46)
<223> OTHER INFORMATION: Hyp, fPro, mPro or Pro
<220> FEATURE:
<221> NAME/KEY: MOD_RES
<222> LOCATION: (49)..(49)
<223> OTHER INFORMATION: Hyp, fPro, mPro or Pro
<220> FEATURE:
<221> NAME/KEY: MOD_RES
<222> LOCATION: (52)..(52)
<223> OTHER INFORMATION: Hyp, fPro, mPro or Pro
<220> FEATURE:
<221> NAME/KEY: MOD_RES
<222> LOCATION: (55)..(55)
```

```
<223> OTHER INFORMATION: Hyp, fPro, mPro or Pro
<220> FEATURE:
<221> NAME/KEY: MOD_RES
<222> LOCATION: (58)..(58)
<223> OTHER INFORMATION: Hyp, fPro, mPro or Pro
<220> FEATURE:
<221> NAME/KEY: MOD_RES
<222> LOCATION: (61)..(61)
<223> OTHER INFORMATION: Hyp, fPro, mPro or Pro
<220> FEATURE:
<221> NAME/KEY: misc_feature
<222> LOCATION: (44)..(61)
<223> OTHER INFORMATION: This region may encompass 1 to 6 "Gly Pro Xaa"
      repeating units
<220> FEATURE:
<221> NAME/KEY: MOD_RES
<222> LOCATION: (62)..(62)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<223> OTHER INFORMATION: see specification as filed for detailed
      description of substitutions and preferred embodiments

<400> SEQUENCE: 20

Xaa Gly Pro Xaa Gly Pro Xaa Gly Pro Xaa Gly Pro Xaa Gly Pro Xaa
1               5                   10                  15

Gly Pro Xaa Gly Pro Xaa Gly Pro Xaa Gly Pro Xaa Gly Pro Xaa Gly
            20                  25                  30

Pro Xaa Gly Pro Xaa Gly Pro Xaa Gly Pro Xaa Gly Pro Xaa Gly Pro
        35                  40                  45

Xaa Gly Pro Xaa Gly Pro Xaa Gly Pro Xaa Gly Pro Xaa Xaa
    50                  55                  60

<210> SEQ ID NO 21
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<221> NAME/KEY: MOD_RES
<222> LOCATION: (3)..(3)
<223> OTHER INFORMATION: Hyp, fPro, mPro or Pro
<220> FEATURE:
<221> NAME/KEY: MOD_RES
<222> LOCATION: (6)..(6)
<223> OTHER INFORMATION: Hyp, fPro, mPro or Pro
<220> FEATURE:
<221> NAME/KEY: MOD_RES
<222> LOCATION: (9)..(9)
<223> OTHER INFORMATION: Hyp, fPro, mPro or Pro
<220> FEATURE:
<221> NAME/KEY: MOD_RES
<222> LOCATION: (12)..(12)
<223> OTHER INFORMATION: Hyp, fPro, mPro or Pro
<220> FEATURE:
<221> NAME/KEY: MOD_RES
<222> LOCATION: (15)..(15)
<223> OTHER INFORMATION: Hyp, fPro, mPro or Pro
<220> FEATURE:
<221> NAME/KEY: MOD_RES
<222> LOCATION: (18)..(18)
<223> OTHER INFORMATION: Hyp, fPro, mPro or Pro
<220> FEATURE:
<221> NAME/KEY: MOD_RES
```

```
<222> LOCATION: (21)..(21)
<223> OTHER INFORMATION: Hyp, fPro, mPro or Pro
<220> FEATURE:
<221> NAME/KEY: MOD_RES
<222> LOCATION: (24)..(24)
<223> OTHER INFORMATION: Hyp, fPro, mPro or Pro
<220> FEATURE:
<221> NAME/KEY: MOD_RES
<222> LOCATION: (27)..(27)
<223> OTHER INFORMATION: Hyp, fPro, mPro or Pro
<220> FEATURE:
<221> NAME/KEY: MOD_RES
<222> LOCATION: (30)..(30)
<223> OTHER INFORMATION: Hyp, fPro, mPro or Pro
<220> FEATURE:
<221> NAME/KEY: misc_feature
<222> LOCATION: (2)..(31)
<223> OTHER INFORMATION: This region may encompass 1 to 10 "Pro Xaa Gly"
      repeating units
<220> FEATURE:
<221> NAME/KEY: MOD_RES
<222> LOCATION: (33)..(33)
<223> OTHER INFORMATION: Hyp
<220> FEATURE:
<221> NAME/KEY: MOD_RES
<222> LOCATION: (36)..(36)
<223> OTHER INFORMATION: Hyp
<220> FEATURE:
<221> NAME/KEY: MOD_RES
<222> LOCATION: (39)..(39)
<223> OTHER INFORMATION: Hyp
<220> FEATURE:
<221> NAME/KEY: MOD_RES
<222> LOCATION: (42)..(42)
<223> OTHER INFORMATION: Hyp
<220> FEATURE:
<221> NAME/KEY: MOD_RES
<222> LOCATION: (45)..(45)
<223> OTHER INFORMATION: Hyp, fPro, mPro or Pro
<220> FEATURE:
<221> NAME/KEY: MOD_RES
<222> LOCATION: (48)..(48)
<223> OTHER INFORMATION: Hyp, fPro, mPro or Pro
<220> FEATURE:
<221> NAME/KEY: MOD_RES
<222> LOCATION: (51)..(51)
<223> OTHER INFORMATION: Hyp, fPro, mPro or Pro
<220> FEATURE:
<221> NAME/KEY: MOD_RES
<222> LOCATION: (54)..(54)
<223> OTHER INFORMATION: Hyp, fPro, mPro or Pro
<220> FEATURE:
<221> NAME/KEY: MOD_RES
<222> LOCATION: (57)..(57)
<223> OTHER INFORMATION: Hyp, fPro, mPro or Pro
<220> FEATURE:
<221> NAME/KEY: MOD_RES
<222> LOCATION: (60)..(60)
<223> OTHER INFORMATION: Hyp, fPro, mPro or Pro
<220> FEATURE:
<221> NAME/KEY: MOD_RES
<222> LOCATION: (63)..(63)
<223> OTHER INFORMATION: Hyp, fPro, mPro or Pro
<220> FEATURE:
<221> NAME/KEY: MOD_RES
<222> LOCATION: (66)..(66)
<223> OTHER INFORMATION: Hyp, fPro, mPro or Pro
<220> FEATURE:
<221> NAME/KEY: MOD_RES
<222> LOCATION: (69)..(69)
<223> OTHER INFORMATION: Hyp, fPro, mPro or Pro
<220> FEATURE:
<221> NAME/KEY: MOD_RES
<222> LOCATION: (72)..(72)
<223> OTHER INFORMATION: Hyp, fPro, mPro or Pro
<220> FEATURE:
<221> NAME/KEY: misc_feature
<222> LOCATION: (44)..(73)
<223> OTHER INFORMATION: This region may encompass 1 to 10 "Pro Xaa Gly"
      repeating units
```

```
<220> FEATURE:
<221> NAME/KEY: MOD_RES
<222> LOCATION: (74)..(74)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<223> OTHER INFORMATION: see specification as filed for detailed
      description of substitutions and preferred embodiments

<400> SEQUENCE: 21

Xaa Pro Xaa Gly Pro Xaa Gly Pro Xaa Gly Pro Xaa Gly Pro Xaa Gly
1               5                   10                  15

Pro Xaa Gly Pro Xaa Gly Pro Xaa Gly Pro Xaa Gly Pro Xaa Gly Pro
            20                  25                  30

Xaa Gly Pro Xaa Gly Pro Xaa Gly Pro Xaa Gly Pro Xaa Gly Pro Xaa
        35                  40                  45

Gly Pro Xaa Gly Pro Xaa Gly Pro Xaa Gly Pro Xaa Gly Pro Xaa Gly
    50                  55                  60

Pro Xaa Gly Pro Xaa Gly Pro Xaa Gly Xaa
65                  70

<210> SEQ ID NO 22
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<221> NAME/KEY: MOD_RES
<222> LOCATION: (3)..(3)
<223> OTHER INFORMATION: Hyp, fPro, mPro or Pro
<220> FEATURE:
<221> NAME/KEY: MOD_RES
<222> LOCATION: (6)..(6)
<223> OTHER INFORMATION: Hyp, fPro, mPro or Pro
<220> FEATURE:
<221> NAME/KEY: MOD_RES
<222> LOCATION: (9)..(9)
<223> OTHER INFORMATION: Hyp, fPro, mPro or Pro
<220> FEATURE:
<221> NAME/KEY: MOD_RES
<222> LOCATION: (12)..(12)
<223> OTHER INFORMATION: Hyp, fPro, mPro or Pro
<220> FEATURE:
<221> NAME/KEY: MOD_RES
<222> LOCATION: (15)..(15)
<223> OTHER INFORMATION: Hyp, fPro, mPro or Pro
<220> FEATURE:
<221> NAME/KEY: MOD_RES
<222> LOCATION: (18)..(18)
<223> OTHER INFORMATION: Hyp, fPro, mPro or Pro
<220> FEATURE:
<221> NAME/KEY: misc_feature
<222> LOCATION: (2)..(19)
<223> OTHER INFORMATION: This region may encompass 1 to 6 "Pro Xaa Gly"
      repeating units
<220> FEATURE:
<221> NAME/KEY: MOD_RES
<222> LOCATION: (21)..(21)
<223> OTHER INFORMATION: Hyp
<220> FEATURE:
<221> NAME/KEY: MOD_RES
<222> LOCATION: (24)..(24)
<223> OTHER INFORMATION: Hyp
```

```
<220> FEATURE:
<221> NAME/KEY: MOD_RES
<222> LOCATION: (27)..(27)
<223> OTHER INFORMATION: Hyp
<220> FEATURE:
<221> NAME/KEY: MOD_RES
<222> LOCATION: (30)..(30)
<223> OTHER INFORMATION: Hyp
<220> FEATURE:
<221> NAME/KEY: MOD_RES
<222> LOCATION: (33)..(33)
<223> OTHER INFORMATION: Hyp
<220> FEATURE:
<221> NAME/KEY: MOD_RES
<222> LOCATION: (36)..(36)
<223> OTHER INFORMATION: Hyp
<220> FEATURE:
<221> NAME/KEY: MOD_RES
<222> LOCATION: (39)..(39)
<223> OTHER INFORMATION: Hyp
<220> FEATURE:
<221> NAME/KEY: MOD_RES
<222> LOCATION: (42)..(42)
<223> OTHER INFORMATION: Hyp
<220> FEATURE:
<221> NAME/KEY: MOD_RES
<222> LOCATION: (45)..(45)
<223> OTHER INFORMATION: Hyp, fPro, mPro or Pro
<220> FEATURE:
<221> NAME/KEY: MOD_RES
<222> LOCATION: (48)..(48)
<223> OTHER INFORMATION: Hyp, fPro, mPro or Pro
<220> FEATURE:
<221> NAME/KEY: MOD_RES
<222> LOCATION: (51)..(51)
<223> OTHER INFORMATION: Hyp, fPro, mPro or Pro
<220> FEATURE:
<221> NAME/KEY: MOD_RES
<222> LOCATION: (54)..(54)
<223> OTHER INFORMATION: Hyp, fPro, mPro or Pro
<220> FEATURE:
<221> NAME/KEY: MOD_RES
<222> LOCATION: (57)..(57)
<223> OTHER INFORMATION: Hyp, fPro, mPro or Pro
<220> FEATURE:
<221> NAME/KEY: MOD_RES
<222> LOCATION: (60)..(60)
<223> OTHER INFORMATION: Hyp, fPro, mPro or Pro
<220> FEATURE:
<221> NAME/KEY: misc_feature
<222> LOCATION: (44)..(61)
<223> OTHER INFORMATION: This region may encompass 1 to 6 "Pro Xaa Gly"
      repeating units
<220> FEATURE:
<221> NAME/KEY: MOD_RES
<222> LOCATION: (62)..(62)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<223> OTHER INFORMATION: see specification as filed for detailed
      description of substitutions and preferred embodiments

<400> SEQUENCE: 22

Xaa Pro Xaa Gly Pro Xaa Gly Pro Xaa Gly Pro Xaa Gly Pro Xaa Gly
1               5                   10                  15

Pro Xaa Gly Pro Xaa Gly Pro Xaa Gly Pro Xaa Gly Pro Xaa Gly Pro
            20                  25                  30

Xaa Gly Pro Xaa Gly Pro Xaa Gly Pro Xaa Gly Pro Xaa Gly Pro Xaa
        35                  40                  45

Gly Pro Xaa Gly Pro Xaa Gly Pro Xaa Gly Pro Xaa Gly Xaa
    50                  55                  60

<210> SEQ ID NO 23
```

```
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<221> NAME/KEY: MOD_RES
<222> LOCATION: (2)..(2)
<223> OTHER INFORMATION: Hyp, fPro, mPro or Pro
<220> FEATURE:
<221> NAME/KEY: MOD_RES
<222> LOCATION: (5)..(5)
<223> OTHER INFORMATION: Hyp, fPro, mPro or Pro
<220> FEATURE:
<221> NAME/KEY: MOD_RES
<222> LOCATION: (8)..(8)
<223> OTHER INFORMATION: Hyp, fPro, mPro or Pro
<220> FEATURE:
<221> NAME/KEY: MOD_RES
<222> LOCATION: (11)..(11)
<223> OTHER INFORMATION: Hyp, fPro, mPro or Pro
<220> FEATURE:
<221> NAME/KEY: MOD_RES
<222> LOCATION: (14)..(14)
<223> OTHER INFORMATION: Hyp, fPro, mPro or Pro
<220> FEATURE:
<221> NAME/KEY: MOD_RES
<222> LOCATION: (17)..(17)
<223> OTHER INFORMATION: Hyp, fPro, mPro or Pro
<220> FEATURE:
<221> NAME/KEY: MOD_RES
<222> LOCATION: (20)..(20)
<223> OTHER INFORMATION: Hyp, fPro, mPro or Pro
<220> FEATURE:
<221> NAME/KEY: MOD_RES
<222> LOCATION: (23)..(23)
<223> OTHER INFORMATION: Hyp, fPro, mPro or Pro
<220> FEATURE:
<221> NAME/KEY: MOD_RES
<222> LOCATION: (26)..(26)
<223> OTHER INFORMATION: Hyp, fPro, mPro or Pro
<220> FEATURE:
<221> NAME/KEY: MOD_RES
<222> LOCATION: (29)..(29)
<223> OTHER INFORMATION: Hyp, fPro, mPro or Pro
<220> FEATURE:
<221> NAME/KEY: misc_feature
<222> LOCATION: (2)..(31)
<223> OTHER INFORMATION: This region may encompass 1 to 10 "Xaa Gly Pro"
      repeating units
<220> FEATURE:
<221> NAME/KEY: MOD_RES
<222> LOCATION: (32)..(32)
<223> OTHER INFORMATION: Hyp
<220> FEATURE:
<221> NAME/KEY: MOD_RES
<222> LOCATION: (35)..(35)
<223> OTHER INFORMATION: Hyp
<220> FEATURE:
<221> NAME/KEY: MOD_RES
<222> LOCATION: (38)..(38)
<223> OTHER INFORMATION: Hyp
<220> FEATURE:
<221> NAME/KEY: MOD_RES
<222> LOCATION: (41)..(41)
<223> OTHER INFORMATION: Hyp
<220> FEATURE:
<221> NAME/KEY: MOD_RES
<222> LOCATION: (44)..(44)
<223> OTHER INFORMATION: Hyp, fPro, mPro or Pro
<220> FEATURE:
<221> NAME/KEY: MOD_RES
```

```
<222> LOCATION: (47)..(47)
<223> OTHER INFORMATION: Hyp, fPro, mPro or Pro
<220> FEATURE:
<221> NAME/KEY: MOD_RES
<222> LOCATION: (50)..(50)
<223> OTHER INFORMATION: Hyp, fPro, mPro or Pro
<220> FEATURE:
<221> NAME/KEY: MOD_RES
<222> LOCATION: (53)..(53)
<223> OTHER INFORMATION: Hyp, fPro, mPro or Pro
<220> FEATURE:
<221> NAME/KEY: MOD_RES
<222> LOCATION: (56)..(56)
<223> OTHER INFORMATION: Hyp, fPro, mPro or Pro
<220> FEATURE:
<221> NAME/KEY: MOD_RES
<222> LOCATION: (59)..(59)
<223> OTHER INFORMATION: Hyp, fPro, mPro or Pro
<220> FEATURE:
<221> NAME/KEY: MOD_RES
<222> LOCATION: (62)..(62)
<223> OTHER INFORMATION: Hyp, fPro, mPro or Pro
<220> FEATURE:
<221> NAME/KEY: MOD_RES
<222> LOCATION: (65)..(65)
<223> OTHER INFORMATION: Hyp, fPro, mPro or Pro
<220> FEATURE:
<221> NAME/KEY: MOD_RES
<222> LOCATION: (68)..(68)
<223> OTHER INFORMATION: Hyp, fPro, mPro or Pro
<220> FEATURE:
<221> NAME/KEY: MOD_RES
<222> LOCATION: (71)..(71)
<223> OTHER INFORMATION: Hyp, fPro, mPro or Pro
<220> FEATURE:
<221> NAME/KEY: misc_feature
<222> LOCATION: (44)..(73)
<223> OTHER INFORMATION: This region may encompass 1 to 10 "Xaa Gly Pro"
      repeating units
<220> FEATURE:
<221> NAME/KEY: MOD_RES
<222> LOCATION: (74)..(74)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<223> OTHER INFORMATION: see specification as filed for detailed
      description of substitutions and preferred embodiments

<400> SEQUENCE: 23

Xaa Xaa Gly Pro Xaa Gly Pro Xaa Gly Pro Xaa Gly Pro Xaa Gly Pro
1               5                   10                  15

Xaa Gly Pro Xaa Gly Pro Xaa Gly Pro Xaa Gly Pro Xaa Gly Pro Xaa
            20                  25                  30

Gly Pro Xaa Gly Pro Xaa Gly Pro Xaa Gly Pro Xaa Gly Pro Xaa Gly
        35                  40                  45

Pro Xaa Gly Pro Xaa Gly Pro Xaa Gly Pro Xaa Gly Pro Xaa Gly Pro
    50                  55                  60

Xaa Gly Pro Xaa Gly Pro Xaa Gly Pro Xaa
65                  70

<210> SEQ ID NO 24
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: F5-Phe, Phe (optionally mono or disubstituted
      on phenyl with fluoro, chloro, bromo, hydroxy, methyl or CF3),
```

```
        Tyr, 3,4(OH)2-Phe, MeO-Tyr, phenylglycine, 2-naphthyl-Ala,
        1-naphthyl-Ala, Trp, Cha, Chg, Met, Leu, Ile or Val
<220> FEATURE:
<221> NAME/KEY: MOD_RES
<222> LOCATION: (2)..(2)
<223> OTHER INFORMATION: Hyp, fPro, mPro or Pro
<220> FEATURE:
<221> NAME/KEY: MOD_RES
<222> LOCATION: (5)..(5)
<223> OTHER INFORMATION: Hyp, fPro, mPro or Pro
<220> FEATURE:
<221> NAME/KEY: MOD_RES
<222> LOCATION: (8)..(8)
<223> OTHER INFORMATION: Hyp, fPro, mPro or Pro
<220> FEATURE:
<221> NAME/KEY: MOD_RES
<222> LOCATION: (11)..(11)
<223> OTHER INFORMATION: Hyp, fPro, mPro or Pro
<220> FEATURE:
<221> NAME/KEY: MOD_RES
<222> LOCATION: (14)..(14)
<223> OTHER INFORMATION: Hyp, fPro, mPro or Pro
<220> FEATURE:
<221> NAME/KEY: MOD_RES
<222> LOCATION: (17)..(17)
<223> OTHER INFORMATION: Hyp, fPro, mPro or Pro
<220> FEATURE:
<221> NAME/KEY: misc_feature
<222> LOCATION: (2)..(19)
<223> OTHER INFORMATION: This region may encompass 1 to 6 "Xaa Gly Pro"
        repeating units
<220> FEATURE:
<221> NAME/KEY: MOD_RES
<222> LOCATION: (20)..(20)
<223> OTHER INFORMATION: Hyp
<220> FEATURE:
<221> NAME/KEY: MOD_RES
<222> LOCATION: (23)..(23)
<223> OTHER INFORMATION: Hyp
<220> FEATURE:
<221> NAME/KEY: MOD_RES
<222> LOCATION: (26)..(26)
<223> OTHER INFORMATION: Hyp
<220> FEATURE:
<221> NAME/KEY: MOD_RES
<222> LOCATION: (29)..(29)
<223> OTHER INFORMATION: Hyp
<220> FEATURE:
<221> NAME/KEY: MOD_RES
<222> LOCATION: (32)..(32)
<223> OTHER INFORMATION: Hyp
<220> FEATURE:
<221> NAME/KEY: MOD_RES
<222> LOCATION: (35)..(35)
<223> OTHER INFORMATION: Hyp
<220> FEATURE:
<221> NAME/KEY: MOD_RES
<222> LOCATION: (38)..(38)
<223> OTHER INFORMATION: Hyp
<220> FEATURE:
<221> NAME/KEY: MOD_RES
<222> LOCATION: (41)..(41)
<223> OTHER INFORMATION: Hyp
<220> FEATURE:
<221> NAME/KEY: MOD_RES
<222> LOCATION: (44)..(44)
<223> OTHER INFORMATION: Hyp, fPro, mPro or Pro
<220> FEATURE:
<221> NAME/KEY: MOD_RES
<222> LOCATION: (47)..(47)
<223> OTHER INFORMATION: Hyp, fPro, mPro or Pro
<220> FEATURE:
<221> NAME/KEY: MOD_RES
<222> LOCATION: (50)..(50)
<223> OTHER INFORMATION: Hyp, fPro, mPro or Pro
<220> FEATURE:
<221> NAME/KEY: MOD_RES
<222> LOCATION: (53)..(53)
<223> OTHER INFORMATION: Hyp, fPro, mPro or Pro
<220> FEATURE:
```

```
<221> NAME/KEY: MOD_RES
<222> LOCATION: (56)..(56)
<223> OTHER INFORMATION: Hyp, fPro, mPro or Pro
<220> FEATURE:
<221> NAME/KEY: MOD_RES
<222> LOCATION: (59)..(59)
<223> OTHER INFORMATION: Hyp, fPro, mPro or Pro
<220> FEATURE:
<221> NAME/KEY: misc_feature
<222> LOCATION: (44)..(61)
<223> OTHER INFORMATION: This region may encompass 1 to 6 "Xaa Gly Pro"
      repeating units
<220> FEATURE:
<221> NAME/KEY: MOD_RES
<222> LOCATION: (62)..(62)
<223> OTHER INFORMATION: F5-Phe, Phe (optionally mono or disubstituted
      on phenyl with fluoro, chloro, bromo, hydroxy, methyl or CF3),
      Tyr, 3,4(OH)2-Phe, MeO-Tyr, phenylglycine, 2-naphthyl-Ala,
      1-naphthyl-Ala, Trp, Cha, Chg, Met, Leu, Ile or Val
<220> FEATURE:
<223> OTHER INFORMATION: see specification as filed for detailed
      description of substitutions and preferred embodiments

<400> SEQUENCE: 24

Xaa Xaa Gly Pro Xaa Gly Pro Xaa Gly Pro Xaa Gly Pro Xaa Gly Pro
1               5                   10                  15

Xaa Gly Pro Xaa Gly Pro Xaa Gly Pro Xaa Gly Pro Xaa Gly Pro Xaa
            20                  25                  30

Gly Pro Xaa Gly Pro Xaa Gly Pro Xaa Gly Pro Xaa Gly Pro Xaa Gly
        35                  40                  45

Pro Xaa Gly Pro Xaa Gly Pro Xaa Gly Pro Xaa Gly Pro Xaa
    50                  55                  60

<210> SEQ ID NO 25
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: F5Phe
<220> FEATURE:
<221> NAME/KEY: MOD_RES
<222> LOCATION: (4)..(4)
<223> OTHER INFORMATION: Hyp
<220> FEATURE:
<221> NAME/KEY: MOD_RES
<222> LOCATION: (7)..(7)
<223> OTHER INFORMATION: Hyp
<220> FEATURE:
<221> NAME/KEY: MOD_RES
<222> LOCATION: (10)..(10)
<223> OTHER INFORMATION: Hyp
<220> FEATURE:
<221> NAME/KEY: MOD_RES
<222> LOCATION: (13)..(13)
<223> OTHER INFORMATION: Hyp
<220> FEATURE:
<221> NAME/KEY: MOD_RES
<222> LOCATION: (16)..(16)
<223> OTHER INFORMATION: Hyp
<220> FEATURE:
<221> NAME/KEY: MOD_RES
<222> LOCATION: (19)..(19)
<223> OTHER INFORMATION: Hyp
<220> FEATURE:
<221> NAME/KEY: MOD_RES
<222> LOCATION: (22)..(22)
<223> OTHER INFORMATION: Hyp
<220> FEATURE:
<221> NAME/KEY: MOD_RES
<222> LOCATION: (25)..(25)
```

```
<223> OTHER INFORMATION: Hyp
<220> FEATURE:
<221> NAME/KEY: MOD_RES
<222> LOCATION: (28)..(28)
<223> OTHER INFORMATION: Hyp
<220> FEATURE:
<221> NAME/KEY: MOD_RES
<222> LOCATION: (31)..(31)
<223> OTHER INFORMATION: Hyp

<400> SEQUENCE: 25

Xaa Gly Pro Xaa Gly Pro Xaa Gly Pro Xaa Gly Pro Xaa Gly Pro Xaa
1               5                   10                  15

Gly Pro Xaa Gly Pro Xaa Gly Pro Xaa Gly Pro Xaa Gly Pro Xaa Phe
            20                  25                  30

<210> SEQ ID NO 26
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Hyp
<220> FEATURE:
<221> NAME/KEY: MOD_RES
<222> LOCATION: (7)..(7)
<223> OTHER INFORMATION: Hyp
<220> FEATURE:
<221> NAME/KEY: MOD_RES
<222> LOCATION: (10)..(10)
<223> OTHER INFORMATION: Hyp
<220> FEATURE:
<221> NAME/KEY: MOD_RES
<222> LOCATION: (13)..(13)
<223> OTHER INFORMATION: Hyp
<220> FEATURE:
<221> NAME/KEY: MOD_RES
<222> LOCATION: (16)..(16)
<223> OTHER INFORMATION: Hyp
<220> FEATURE:
<221> NAME/KEY: MOD_RES
<222> LOCATION: (19)..(19)
<223> OTHER INFORMATION: Hyp
<220> FEATURE:
<221> NAME/KEY: MOD_RES
<222> LOCATION: (22)..(22)
<223> OTHER INFORMATION: Hyp
<220> FEATURE:
<221> NAME/KEY: MOD_RES
<222> LOCATION: (25)..(25)
<223> OTHER INFORMATION: Hyp
<220> FEATURE:
<221> NAME/KEY: MOD_RES
<222> LOCATION: (28)..(28)
<223> OTHER INFORMATION: Hyp
<220> FEATURE:
<221> NAME/KEY: MOD_RES
<222> LOCATION: (31)..(31)
<223> OTHER INFORMATION: Hyp

<400> SEQUENCE: 26

Phe Gly Pro Xaa Gly Pro Xaa Gly Pro Xaa Gly Pro Xaa Gly Pro Xaa
1               5                   10                  15

Gly Pro Xaa Gly Pro Xaa Gly Pro Xaa Gly Pro Xaa Gly Pro Xaa Phe
            20                  25                  30

<210> SEQ ID NO 27
<211> LENGTH: 32
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Hyp
<220> FEATURE:
<221> NAME/KEY: MOD_RES
<222> LOCATION: (7)..(7)
<223> OTHER INFORMATION: Hyp
<220> FEATURE:
<221> NAME/KEY: MOD_RES
<222> LOCATION: (10)..(10)
<223> OTHER INFORMATION: Hyp
<220> FEATURE:
<221> NAME/KEY: MOD_RES
<222> LOCATION: (13)..(13)
<223> OTHER INFORMATION: Hyp
<220> FEATURE:
<221> NAME/KEY: MOD_RES
<222> LOCATION: (16)..(16)
<223> OTHER INFORMATION: Hyp
<220> FEATURE:
<221> NAME/KEY: MOD_RES
<222> LOCATION: (19)..(19)
<223> OTHER INFORMATION: Hyp
<220> FEATURE:
<221> NAME/KEY: MOD_RES
<222> LOCATION: (22)..(22)
<223> OTHER INFORMATION: Hyp
<220> FEATURE:
<221> NAME/KEY: MOD_RES
<222> LOCATION: (25)..(25)
<223> OTHER INFORMATION: Hyp
<220> FEATURE:
<221> NAME/KEY: MOD_RES
<222> LOCATION: (28)..(28)
<223> OTHER INFORMATION: Hyp
<220> FEATURE:
<221> NAME/KEY: MOD_RES
<222> LOCATION: (31)..(31)
<223> OTHER INFORMATION: Hyp

<400> SEQUENCE: 27

Leu Gly Pro Xaa Gly Pro Xaa Gly Pro Xaa Gly Pro Xaa Gly Pro Xaa
1               5                   10                  15

Gly Pro Xaa Gly Pro Xaa Gly Pro Xaa Gly Pro Xaa Gly Pro Xaa Phe
            20                  25                  30

<210> SEQ ID NO 28
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Hyp
<220> FEATURE:
<221> NAME/KEY: MOD_RES
<222> LOCATION: (7)..(7)
<223> OTHER INFORMATION: Hyp
<220> FEATURE:
<221> NAME/KEY: MOD_RES
<222> LOCATION: (10)..(10)
<223> OTHER INFORMATION: Hyp
<220> FEATURE:
<221> NAME/KEY: MOD_RES
<222> LOCATION: (13)..(13)
<223> OTHER INFORMATION: Hyp
<220> FEATURE:
<221> NAME/KEY: MOD_RES
<222> LOCATION: (16)..(16)
<223> OTHER INFORMATION: Hyp
```

```
<220> FEATURE:
<221> NAME/KEY: MOD_RES
<222> LOCATION: (19)..(19)
<223> OTHER INFORMATION: Hyp
<220> FEATURE:
<221> NAME/KEY: MOD_RES
<222> LOCATION: (22)..(22)
<223> OTHER INFORMATION: Hyp
<220> FEATURE:
<221> NAME/KEY: MOD_RES
<222> LOCATION: (25)..(25)
<223> OTHER INFORMATION: Hyp
<220> FEATURE:
<221> NAME/KEY: MOD_RES
<222> LOCATION: (28)..(28)
<223> OTHER INFORMATION: Hyp
<220> FEATURE:
<221> NAME/KEY: MOD_RES
<222> LOCATION: (31)..(31)
<223> OTHER INFORMATION: Hyp

<400> SEQUENCE: 28

Gly Gly Pro Xaa Gly Pro Xaa Gly Pro Xaa Gly Pro Xaa Gly Pro Xaa
1               5                   10                  15

Gly Pro Xaa Gly Pro Xaa Gly Pro Xaa Gly Pro Xaa Gly Pro Xaa Gly
            20                  25                  30

<210> SEQ ID NO 29
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Acetylated
<220> FEATURE:
<221> NAME/KEY: MOD_RES
<222> LOCATION: (3)..(3)
<223> OTHER INFORMATION: Hyp
<220> FEATURE:
<221> NAME/KEY: MOD_RES
<222> LOCATION: (6)..(6)
<223> OTHER INFORMATION: Hyp
<220> FEATURE:
<221> NAME/KEY: MOD_RES
<222> LOCATION: (9)..(9)
<223> OTHER INFORMATION: Hyp
<220> FEATURE:
<221> NAME/KEY: MOD_RES
<222> LOCATION: (12)..(12)
<223> OTHER INFORMATION: Hyp
<220> FEATURE:
<221> NAME/KEY: MOD_RES
<222> LOCATION: (15)..(15)
<223> OTHER INFORMATION: Hyp
<220> FEATURE:
<221> NAME/KEY: MOD_RES
<222> LOCATION: (18)..(18)
<223> OTHER INFORMATION: Hyp
<220> FEATURE:
<221> NAME/KEY: MOD_RES
<222> LOCATION: (21)..(21)
<223> OTHER INFORMATION: Hyp
<220> FEATURE:
<221> NAME/KEY: MOD_RES
<222> LOCATION: (24)..(24)
<223> OTHER INFORMATION: Hyp
<220> FEATURE:
<221> NAME/KEY: MOD_RES
<222> LOCATION: (27)..(27)
<223> OTHER INFORMATION: Hyp
<220> FEATURE:
<221> NAME/KEY: MOD_RES
<222> LOCATION: (30)..(30)
<223> OTHER INFORMATION: Hyp
```

-continued

```
<400> SEQUENCE: 29

Gly Pro Xaa Gly Pro Xaa Gly Pro Xaa Gly Pro Xaa Gly Pro Xaa Gly
1               5                   10                  15

Pro Xaa Gly Pro Xaa Gly Pro Xaa Gly Pro Xaa Gly Pro Xaa Gly
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Hyp
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp
<220> FEATURE:
<221> NAME/KEY: MOD_RES
<222> LOCATION: (23)..(23)
<223> OTHER INFORMATION: Hyp
<220> FEATURE:
<221> NAME/KEY: MOD_RES
<222> LOCATION: (26)..(26)
<223> OTHER INFORMATION: Hyp
<220> FEATURE:
<221> NAME/KEY: MOD_RES
<222> LOCATION: (29)..(29)
<223> OTHER INFORMATION: Hyp

<400> SEQUENCE: 30

Pro Xaa Gly Pro Xaa Gly Pro Xaa Gly Pro Xaa Gly Pro Xaa Ala Pro
1               5                   10                  15

Xaa Gly Pro Xaa Gly Pro Xaa Gly Pro Xaa Gly Pro Xaa Gly
            20                  25                  30

<210> SEQ ID NO 31
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: F5Phe
<220> FEATURE:
<221> NAME/KEY: MOD_RES
<222> LOCATION: (4)..(4)
```

```
<223> OTHER INFORMATION: Hyp
<220> FEATURE:
<221> NAME/KEY: MOD_RES
<222> LOCATION: (7)..(7)
<223> OTHER INFORMATION: Hyp
<220> FEATURE:
<221> NAME/KEY: MOD_RES
<222> LOCATION: (10)..(10)
<223> OTHER INFORMATION: Hyp
<220> FEATURE:
<221> NAME/KEY: MOD_RES
<222> LOCATION: (13)..(13)
<223> OTHER INFORMATION: Hyp
<220> FEATURE:
<221> NAME/KEY: MOD_RES
<222> LOCATION: (16)..(16)
<223> OTHER INFORMATION: Hyp
<220> FEATURE:
<221> NAME/KEY: MOD_RES
<222> LOCATION: (19)..(19)
<223> OTHER INFORMATION: Hyp
<220> FEATURE:
<221> NAME/KEY: MOD_RES
<222> LOCATION: (22)..(22)
<223> OTHER INFORMATION: Hyp
<220> FEATURE:
<221> NAME/KEY: MOD_RES
<222> LOCATION: (25)..(25)
<223> OTHER INFORMATION: Hyp
<220> FEATURE:
<221> NAME/KEY: MOD_RES
<222> LOCATION: (28)..(28)
<223> OTHER INFORMATION: Hyp

<400> SEQUENCE: 31

Xaa Gly Pro Xaa Gly Pro Xaa Gly Pro Xaa Gly Pro Xaa Gly Pro Xaa
1               5                   10                  15

Gly Pro Xaa Gly Pro Xaa Gly Pro Xaa Gly Pro Xaa Phe
            20                  25

<210> SEQ ID NO 32
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Hyp
<220> FEATURE:
<221> NAME/KEY: MOD_RES
<222> LOCATION: (7)..(7)
<223> OTHER INFORMATION: Hyp
<220> FEATURE:
<221> NAME/KEY: MOD_RES
<222> LOCATION: (10)..(10)
<223> OTHER INFORMATION: Hyp
<220> FEATURE:
<221> NAME/KEY: MOD_RES
<222> LOCATION: (13)..(13)
<223> OTHER INFORMATION: Hyp
<220> FEATURE:
<221> NAME/KEY: MOD_RES
<222> LOCATION: (16)..(16)
<223> OTHER INFORMATION: Hyp
<220> FEATURE:
<221> NAME/KEY: MOD_RES
<222> LOCATION: (19)..(19)
<223> OTHER INFORMATION: Hyp
<220> FEATURE:
<221> NAME/KEY: MOD_RES
<222> LOCATION: (22)..(22)
<223> OTHER INFORMATION: Hyp
<220> FEATURE:
<221> NAME/KEY: MOD_RES
```

```
<222> LOCATION: (25)..(25)
<223> OTHER INFORMATION: Hyp
<220> FEATURE:
<221> NAME/KEY: MOD_RES
<222> LOCATION: (28)..(28)
<223> OTHER INFORMATION: Hyp

<400> SEQUENCE: 32

Phe Gly Pro Xaa Gly Pro Xaa Gly Pro Xaa Gly Pro Xaa Gly Pro Xaa
1               5                   10                  15

Gly Pro Xaa Gly Pro Xaa Gly Pro Xaa Gly Pro Xaa Phe
            20                  25

<210> SEQ ID NO 33
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Hyp
<220> FEATURE:
<221> NAME/KEY: MOD_RES
<222> LOCATION: (7)..(7)
<223> OTHER INFORMATION: Hyp
<220> FEATURE:
<221> NAME/KEY: MOD_RES
<222> LOCATION: (10)..(10)
<223> OTHER INFORMATION: Hyp
<220> FEATURE:
<221> NAME/KEY: MOD_RES
<222> LOCATION: (13)..(13)
<223> OTHER INFORMATION: Hyp
<220> FEATURE:
<221> NAME/KEY: MOD_RES
<222> LOCATION: (16)..(16)
<223> OTHER INFORMATION: Hyp
<220> FEATURE:
<221> NAME/KEY: MOD_RES
<222> LOCATION: (19)..(19)
<223> OTHER INFORMATION: Hyp
<220> FEATURE:
<221> NAME/KEY: MOD_RES
<222> LOCATION: (22)..(22)
<223> OTHER INFORMATION: Hyp
<220> FEATURE:
<221> NAME/KEY: MOD_RES
<222> LOCATION: (25)..(25)
<223> OTHER INFORMATION: Hyp
<220> FEATURE:
<221> NAME/KEY: MOD_RES
<222> LOCATION: (28)..(28)
<223> OTHER INFORMATION: Hyp

<400> SEQUENCE: 33

Leu Gly Pro Xaa Gly Pro Xaa Gly Pro Xaa Gly Pro Xaa Gly Pro Xaa
1               5                   10                  15

Gly Pro Xaa Gly Pro Xaa Gly Pro Xaa Gly Pro Xaa Phe
            20                  25

<210> SEQ ID NO 34
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Hyp
```

```
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp
<220> FEATURE:
<221> NAME/KEY: MOD_RES
<222> LOCATION: (23)..(23)
<223> OTHER INFORMATION: Hyp
<220> FEATURE:
<221> NAME/KEY: MOD_RES
<222> LOCATION: (26)..(26)
<223> OTHER INFORMATION: Hyp
<220> FEATURE:
<221> NAME/KEY: MOD_RES
<222> LOCATION: (29)..(29)
<223> OTHER INFORMATION: Hyp

<400> SEQUENCE: 34

Pro Xaa Gly Pro Xaa Gly Pro Xaa Gly Pro Xaa Gly Pro Xaa Gly Pro
1               5                   10                  15

Xaa Gly Pro Xaa Gly Pro Xaa Gly Pro Xaa Gly Pro Xaa Gly
            20                  25                  30

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: F5Phe
<220> FEATURE:
<221> NAME/KEY: MOD_RES
<222> LOCATION: (4)..(4)
<223> OTHER INFORMATION: Hyp
<220> FEATURE:
<221> NAME/KEY: MOD_RES
<222> LOCATION: (7)..(7)
<223> OTHER INFORMATION: Hyp
<220> FEATURE:
<221> NAME/KEY: MOD_RES
<222> LOCATION: (10)..(10)
<223> OTHER INFORMATION: Hyp
<220> FEATURE:
<221> NAME/KEY: MOD_RES
<222> LOCATION: (13)..(13)
<223> OTHER INFORMATION: Hyp
<220> FEATURE:
<221> NAME/KEY: MOD_RES
<222> LOCATION: (16)..(16)
<223> OTHER INFORMATION: Hyp

<400> SEQUENCE: 35
```

```
Xaa Gly Pro Xaa Gly Pro Xaa Gly Pro Xaa Gly Pro Xaa Gly Pro Xaa
1               5                   10                  15

Phe

<210> SEQ ID NO 36
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Hyp
<220> FEATURE:
<221> NAME/KEY: MOD_RES
<222> LOCATION: (6)..(6)
<223> OTHER INFORMATION: Hyp
<220> FEATURE:
<221> NAME/KEY: MOD_RES
<222> LOCATION: (9)..(9)
<223> OTHER INFORMATION: Hyp
<220> FEATURE:
<221> NAME/KEY: MOD_RES
<222> LOCATION: (12)..(12)
<223> OTHER INFORMATION: Hyp
<220> FEATURE:
<221> NAME/KEY: MOD_RES
<222> LOCATION: (15)..(15)
<223> OTHER INFORMATION: Hyp
<220> FEATURE:
<221> NAME/KEY: MOD_RES
<222> LOCATION: (18)..(18)
<223> OTHER INFORMATION: Hyp
<220> FEATURE:
<221> NAME/KEY: MOD_RES
<222> LOCATION: (21)..(21)
<223> OTHER INFORMATION: Hyp
<220> FEATURE:
<221> NAME/KEY: MOD_RES
<222> LOCATION: (24)..(24)
<223> OTHER INFORMATION: Hyp
<220> FEATURE:
<221> NAME/KEY: MOD_RES
<222> LOCATION: (27)..(27)
<223> OTHER INFORMATION: Hyp
<220> FEATURE:
<221> NAME/KEY: MOD_RES
<222> LOCATION: (30)..(30)
<223> OTHER INFORMATION: Hyp

<400> SEQUENCE: 36

Gly Pro Xaa Gly Pro Xaa Gly Pro Xaa Gly Pro Xaa Gly Pro Xaa Gly
1               5                   10                  15

Pro Xaa Gly Pro Xaa Gly Pro Xaa Gly Pro Xaa Gly Pro Xaa
            20                  25                  30

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gln, Asn, Leu, Ile, Val or Ala
<220> FEATURE:
<221> NAME/KEY: MOD_RES
<222> LOCATION: (4)..(4)
<223> OTHER INFORMATION: Ile or Leu

<400> SEQUENCE: 37
```

```
Pro Xaa Gly Xaa Ala Gly
1               5

<210> SEQ ID NO 38
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Flp
<220> FEATURE:
<221> NAME/KEY: MOD_RES
<222> LOCATION: (5)..(5)
<223> OTHER INFORMATION: Flp
<220> FEATURE:
<221> NAME/KEY: MOD_RES
<222> LOCATION: (8)..(8)
<223> OTHER INFORMATION: Flp
<220> FEATURE:
<221> NAME/KEY: MOD_RES
<222> LOCATION: (11)..(11)
<223> OTHER INFORMATION: Flp
<220> FEATURE:
<221> NAME/KEY: MOD_RES
<222> LOCATION: (14)..(14)
<223> OTHER INFORMATION: Flp
<220> FEATURE:
<221> NAME/KEY: MOD_RES
<222> LOCATION: (17)..(17)
<223> OTHER INFORMATION: Flp
<220> FEATURE:
<221> NAME/KEY: MOD_RES
<222> LOCATION: (20)..(20)
<223> OTHER INFORMATION: Flp
<220> FEATURE:
<221> NAME/KEY: MOD_RES
<222> LOCATION: (23)..(23)
<223> OTHER INFORMATION: Flp
<220> FEATURE:
<221> NAME/KEY: MOD_RES
<222> LOCATION: (26)..(26)
<223> OTHER INFORMATION: Flp
<220> FEATURE:
<221> NAME/KEY: MOD_RES
<222> LOCATION: (29)..(29)
<223> OTHER INFORMATION: Flp

<400> SEQUENCE: 38

Pro Xaa Gly Pro Xaa Gly Pro Xaa Gly Pro Xaa Gly Pro Xaa Gly Pro
1               5                   10                  15

Xaa Gly Pro Xaa Gly Pro Xaa Gly Pro Xaa Gly Pro Xaa Gly
            20                  25                  30

<210> SEQ ID NO 39
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Hyp, fPro, mPro or Pro
<220> FEATURE:
<221> NAME/KEY: MOD_RES
<222> LOCATION: (6)..(6)
<223> OTHER INFORMATION: Hyp, fPro, mPro or Pro
<220> FEATURE:
<221> NAME/KEY: MOD_RES
<222> LOCATION: (9)..(9)
```

```
<223> OTHER INFORMATION: Hyp, fPro, mPro or Pro
<220> FEATURE:
<221> NAME/KEY: MOD_RES
<222> LOCATION: (12)..(12)
<223> OTHER INFORMATION: Hyp, fPro, mPro or Pro
<220> FEATURE:
<221> NAME/KEY: MOD_RES
<222> LOCATION: (15)..(15)
<223> OTHER INFORMATION: Hyp, fPro, mPro or Pro
<220> FEATURE:
<221> NAME/KEY: MOD_RES
<222> LOCATION: (18)..(18)
<223> OTHER INFORMATION: Hyp, fPro, mPro or Pro
<220> FEATURE:
<221> NAME/KEY: MOD_RES
<222> LOCATION: (21)..(21)
<223> OTHER INFORMATION: Hyp, fPro, mPro or Pro
<220> FEATURE:
<221> NAME/KEY: MOD_RES
<222> LOCATION: (24)..(24)
<223> OTHER INFORMATION: Hyp, fPro, mPro or Pro
<220> FEATURE:
<221> NAME/KEY: MOD_RES
<222> LOCATION: (27)..(27)
<223> OTHER INFORMATION: Hyp, fPro, mPro or Pro
<220> FEATURE:
<221> NAME/KEY: MOD_RES
<222> LOCATION: (30)..(30)
<223> OTHER INFORMATION: Hyp, fPro, mPro or Pro
<220> FEATURE:
<221> NAME/KEY: misc_feature
<222> LOCATION: (1)..(30)
<223> OTHER INFORMATION: This sequence may encompass 1 to 10
      "Gly Pro Xaa" repeating units
<220> FEATURE:
<223> OTHER INFORMATION: see specification as filed for detailed
      description of substitutions and preferred embodiments

<400> SEQUENCE: 39

Gly Pro Xaa Gly Pro Xaa Gly Pro Xaa Gly Pro Xaa Gly Pro Xaa Gly
1               5                   10                  15

Pro Xaa Gly Pro Xaa Gly Pro Xaa Gly Pro Xaa Gly Pro Xaa
            20                  25                  30

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Hyp
<220> FEATURE:
<221> NAME/KEY: MOD_RES
<222> LOCATION: (6)..(6)
<223> OTHER INFORMATION: Hyp
<220> FEATURE:
<221> NAME/KEY: MOD_RES
<222> LOCATION: (9)..(9)
<223> OTHER INFORMATION: Hyp
<220> FEATURE:
<221> NAME/KEY: MOD_RES
<222> LOCATION: (12)..(12)
<223> OTHER INFORMATION: Hyp

<400> SEQUENCE: 40

Gly Pro Xaa Gly Pro Xaa Gly Pro Xaa Gly Pro Xaa
1               5                   10

<210> SEQ ID NO 41
<211> LENGTH: 18
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Hyp, fPro, mPro or Pro
<220> FEATURE:
<221> NAME/KEY: MOD_RES
<222> LOCATION: (6)..(6)
<223> OTHER INFORMATION: Hyp, fPro, mPro or Pro
<220> FEATURE:
<221> NAME/KEY: MOD_RES
<222> LOCATION: (9)..(9)
<223> OTHER INFORMATION: Hyp, fPro, mPro or Pro
<220> FEATURE:
<221> NAME/KEY: MOD_RES
<222> LOCATION: (12)..(12)
<223> OTHER INFORMATION: Hyp, fPro, mPro or Pro
<220> FEATURE:
<221> NAME/KEY: MOD_RES
<222> LOCATION: (15)..(15)
<223> OTHER INFORMATION: Hyp, fPro, mPro or Pro
<220> FEATURE:
<221> NAME/KEY: MOD_RES
<222> LOCATION: (18)..(18)
<223> OTHER INFORMATION: Hyp, fPro, mPro or Pro
<220> FEATURE:
<221> NAME/KEY: misc_feature
<222> LOCATION: (1)..(18)
<223> OTHER INFORMATION: This sequence may encompass 1 to 6
      "Gly Pro Xaa" repeating units
<220> FEATURE:
<223> OTHER INFORMATION: see specification as filed for detailed
      description of substitutions and preferred embodiments

<400> SEQUENCE: 41

Gly Pro Xaa Gly Pro Xaa Gly Pro Xaa Gly Pro Xaa Gly Pro Xaa Gly
1               5                   10                  15

Pro Xaa

<210> SEQ ID NO 42
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Hyp
<220> FEATURE:
<221> NAME/KEY: MOD_RES
<222> LOCATION: (6)..(6)
<223> OTHER INFORMATION: Hyp
<220> FEATURE:
<221> NAME/KEY: MOD_RES
<222> LOCATION: (9)..(9)
<223> OTHER INFORMATION: Hyp
<220> FEATURE:
<221> NAME/KEY: MOD_RES
<222> LOCATION: (12)..(12)
<223> OTHER INFORMATION: Hyp
<220> FEATURE:
<221> NAME/KEY: MOD_RES
<222> LOCATION: (15)..(15)
<223> OTHER INFORMATION: Hyp
<220> FEATURE:
<221> NAME/KEY: MOD_RES
<222> LOCATION: (18)..(18)
<223> OTHER INFORMATION: Hyp
<220> FEATURE:
<221> NAME/KEY: MOD_RES
<222> LOCATION: (21)..(21)
<223> OTHER INFORMATION: Hyp
```

```
<220> FEATURE:
<221> NAME/KEY: MOD_RES
<222> LOCATION: (24)..(24)
<223> OTHER INFORMATION: Hyp

<400> SEQUENCE: 42

Gly Pro Xaa Gly Pro Xaa Gly Pro Xaa Gly Pro Xaa Gly Pro Xaa Gly
1               5                   10                  15

Pro Xaa Gly Pro Xaa Gly Pro Xaa
            20

<210> SEQ ID NO 43
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Hyp, fPro, mPro or Pro
<220> FEATURE:
<221> NAME/KEY: MOD_RES
<222> LOCATION: (5)..(5)
<223> OTHER INFORMATION: Hyp, fPro, mPro or Pro
<220> FEATURE:
<221> NAME/KEY: MOD_RES
<222> LOCATION: (8)..(8)
<223> OTHER INFORMATION: Hyp, fPro, mPro or Pro
<220> FEATURE:
<221> NAME/KEY: MOD_RES
<222> LOCATION: (11)..(11)
<223> OTHER INFORMATION: Hyp, fPro, mPro or Pro
<220> FEATURE:
<221> NAME/KEY: MOD_RES
<222> LOCATION: (14)..(14)
<223> OTHER INFORMATION: Hyp, fPro, mPro or Pro
<220> FEATURE:
<221> NAME/KEY: MOD_RES
<222> LOCATION: (17)..(17)
<223> OTHER INFORMATION: Hyp, fPro, mPro or Pro
<220> FEATURE:
<221> NAME/KEY: MOD_RES
<222> LOCATION: (20)..(20)
<223> OTHER INFORMATION: Hyp, fPro, mPro or Pro
<220> FEATURE:
<221> NAME/KEY: MOD_RES
<222> LOCATION: (23)..(23)
<223> OTHER INFORMATION: Hyp, fPro, mPro or Pro
<220> FEATURE:
<221> NAME/KEY: MOD_RES
<222> LOCATION: (26)..(26)
<223> OTHER INFORMATION: Hyp, fPro, mPro or Pro
<220> FEATURE:
<221> NAME/KEY: MOD_RES
<222> LOCATION: (29)..(29)
<223> OTHER INFORMATION: Hyp, fPro, mPro or Pro
<220> FEATURE:
<221> NAME/KEY: misc_feature
<222> LOCATION: (1)..(30)
<223> OTHER INFORMATION: This sequence may encompass 1 to 10
      "Pro Xaa Gly" repeating units
<220> FEATURE:
<223> OTHER INFORMATION: see specification as filed for detailed
      description of substitutions and preferred embodiments

<400> SEQUENCE: 43

Pro Xaa Gly Pro Xaa Gly Pro Xaa Gly Pro Xaa Gly Pro Xaa Gly Pro
1               5                   10                  15

Xaa Gly Pro Xaa Gly Pro Xaa Gly Pro Xaa Gly Pro Xaa Gly
            20                  25                  30

<210> SEQ ID NO 44
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hyp, fPro, mPro or Pro
<220> FEATURE:
<221> NAME/KEY: MOD_RES
<222> LOCATION: (5)..(5)
<223> OTHER INFORMATION: Hyp, fPro, mPro or Pro
<220> FEATURE:
<221> NAME/KEY: MOD_RES
<222> LOCATION: (8)..(8)
<223> OTHER INFORMATION: Hyp, fPro, mPro or Pro
<220> FEATURE:
<221> NAME/KEY: MOD_RES
<222> LOCATION: (11)..(11)
<223> OTHER INFORMATION: Hyp, fPro, mPro or Pro
<220> FEATURE:
<221> NAME/KEY: MOD_RES
<222> LOCATION: (14)..(14)
<223> OTHER INFORMATION: Hyp, fPro, mPro or Pro
<220> FEATURE:
<221> NAME/KEY: MOD_RES
<222> LOCATION: (17)..(17)
<223> OTHER INFORMATION: Hyp, fPro, mPro or Pro
<220> FEATURE:
<221> NAME/KEY: misc_feature
<222> LOCATION: (1)..(18)
<223> OTHER INFORMATION: This sequence may encompass 1 to 6
      "Pro Xaa Gly" repeating units
<220> FEATURE:
<223> OTHER INFORMATION: see specification as filed for detailed
      description of substitutions and preferred embodiments

<400> SEQUENCE: 44

Pro Xaa Gly Pro Xaa Gly Pro Xaa Gly Pro Xaa Gly Pro Xaa Gly Pro
1               5                   10                  15

Xaa Gly

<210> SEQ ID NO 45
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Hyp, fPro, mPro or Pro
<220> FEATURE:
<221> NAME/KEY: MOD_RES
<222> LOCATION: (4)..(4)
<223> OTHER INFORMATION: Hyp, fPro, mPro or Pro
<220> FEATURE:
<221> NAME/KEY: MOD_RES
<222> LOCATION: (7)..(7)
<223> OTHER INFORMATION: Hyp, fPro, mPro or Pro
<220> FEATURE:
<221> NAME/KEY: MOD_RES
<222> LOCATION: (10)..(10)
<223> OTHER INFORMATION: Hyp, fPro, mPro or Pro
<220> FEATURE:
<221> NAME/KEY: MOD_RES
<222> LOCATION: (13)..(13)
<223> OTHER INFORMATION: Hyp, fPro, mPro or Pro
<220> FEATURE:
<221> NAME/KEY: MOD_RES
<222> LOCATION: (16)..(16)
<223> OTHER INFORMATION: Hyp, fPro, mPro or Pro
<220> FEATURE:
<221> NAME/KEY: MOD_RES
```

```
<222> LOCATION: (19)..(19)
<223> OTHER INFORMATION: Hyp, fPro, mPro or Pro
<220> FEATURE:
<221> NAME/KEY: MOD_RES
<222> LOCATION: (22)..(22)
<223> OTHER INFORMATION: Hyp, fPro, mPro or Pro
<220> FEATURE:
<221> NAME/KEY: MOD_RES
<222> LOCATION: (25)..(25)
<223> OTHER INFORMATION: Hyp, fPro, mPro or Pro
<220> FEATURE:
<221> NAME/KEY: MOD_RES
<222> LOCATION: (28)..(28)
<223> OTHER INFORMATION: Hyp, fPro, mPro or Pro
<220> FEATURE:
<221> NAME/KEY: misc_feature
<222> LOCATION: (1)..(30)
<223> OTHER INFORMATION: This sequence may encompass 1 to 10
      "Xaa Gly Pro" repeating units
<220> FEATURE:
<223> OTHER INFORMATION: see specification as filed for detailed
      description of substitutions and preferred embodiments

<400> SEQUENCE: 45

Xaa Gly Pro Xaa Gly Pro Xaa Gly Pro Xaa Gly Pro Xaa Gly Pro Xaa
1               5                   10                  15

Gly Pro Xaa Gly Pro Xaa Gly Pro Xaa Gly Pro Xaa Gly Pro
            20                  25                  30

<210> SEQ ID NO 46
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hyp, fPro, mPro or Pro
<220> FEATURE:
<221> NAME/KEY: MOD_RES
<222> LOCATION: (4)..(4)
<223> OTHER INFORMATION: Hyp, fPro, mPro or Pro
<220> FEATURE:
<221> NAME/KEY: MOD_RES
<222> LOCATION: (7)..(7)
<223> OTHER INFORMATION: Hyp, fPro, mPro or Pro
<220> FEATURE:
<221> NAME/KEY: MOD_RES
<222> LOCATION: (10)..(10)
<223> OTHER INFORMATION: Hyp, fPro, mPro or Pro
<220> FEATURE:
<221> NAME/KEY: MOD_RES
<222> LOCATION: (13)..(13)
<223> OTHER INFORMATION: Hyp, fPro, mPro or Pro
<220> FEATURE:
<221> NAME/KEY: MOD_RES
<222> LOCATION: (16)..(16)
<223> OTHER INFORMATION: Hyp, fPro, mPro or Pro
<220> FEATURE:
<221> NAME/KEY: misc_feature
<222> LOCATION: (1)..(18)
<223> OTHER INFORMATION: This sequence may encompass 1 to 6
      "Xaa Gly Pro" repeating units
<220> FEATURE:
<223> OTHER INFORMATION: see specification as filed for detailed
      description of substitutions and preferred embodiments

<400> SEQUENCE: 46

Xaa Gly Pro Xaa Gly Pro Xaa Gly Pro Xaa Gly Pro Xaa Gly Pro Xaa
1               5                   10                  15

Gly Pro
```

```
<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Hyp
<220> FEATURE:
<221> NAME/KEY: MOD_RES
<222> LOCATION: (6)..(6)
<223> OTHER INFORMATION: Hyp
<220> FEATURE:
<221> NAME/KEY: MOD_RES
<222> LOCATION: (9)..(9)
<223> OTHER INFORMATION: Hyp
<220> FEATURE:
<221> NAME/KEY: MOD_RES
<222> LOCATION: (12)..(12)
<223> OTHER INFORMATION: Hyp
<220> FEATURE:
<221> NAME/KEY: misc_feature
<222> LOCATION: (1)..(12)
<223> OTHER INFORMATION: This sequence may encompass 0 to 4
      "Gly Pro Xaa" repeating units
<220> FEATURE:
<223> OTHER INFORMATION: see specification as filed for detailed
      description of substitutions and preferred embodiments

<400> SEQUENCE: 47

Gly Pro Xaa Gly Pro Xaa Gly Pro Xaa Gly Pro Xaa
1               5                   10
```